United States Patent
Chu et al.

(10) Patent No.: US 8,426,413 B2
(45) Date of Patent: Apr. 23, 2013

(54) DIARYL SUBSTITUTED ALKANES

(75) Inventors: Lin Chu, Scotch Plains, NJ (US); Bing Li, Towaco, NJ (US); Anthony K. Ogawa, Mountainside, NJ (US); Hyun O. Ok, Colonia, NJ (US); Debra L. Ondeyka, Fanwood, NJ (US); Minal Patel, Galloway, NJ (US); Rosemary Sisco, Old Bridge, NJ (US); Feroze Ujjainwalla, Scotch Plains, NJ (US); Jinyou Xu, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/403,643

(22) Filed: Feb. 23, 2012

(65) Prior Publication Data

US 2012/0149674 A1    Jun. 14, 2012

Related U.S. Application Data

(62) Division of application No. 12/296,117, filed as application No. PCT/US2007/008583 on Apr. 6, 2007, now Pat. No. 8,124,628.

(60) Provisional application No. 60/790,958, filed on Apr. 11, 2006.

(51) Int. Cl.
  *A61K 31/506* (2006.01)
  *A61K 31/501* (2006.01)
  *A61K 31/444* (2006.01)
  *C07D 401/14* (2006.01)
  *C07D 401/04* (2006.01)

(52) U.S. Cl.
  USPC ........... 514/252.03; 514/275; 514/252.02; 514/334; 544/238; 544/331; 546/257

(58) Field of Classification Search ............ 514/252.03, 514/275, 252.02, 334; 544/238, 331; 546/257
  See application file for complete search history.

(56) References Cited

U.S. PATENT DOCUMENTS

| 5,668,146 A | 9/1997 | Brooks et al. |
| 6,051,573 A | 4/2000 | Clark |
| 2007/0287736 A1 | 12/2007 | Chu et al. |
| 2010/0210617 A1* | 8/2010 | Woodhead et al. ........ 514/210.2 |

FOREIGN PATENT DOCUMENTS

| WO | WO00/50402 A1 | 8/2000 |
| WO | WO2005/009951 A2 | 2/2005 |
| WO | WO2006/044602 A2 | 4/2006 |
| WO | WO2006/098912 A1 | 9/2006 |
| WO | WO2007/056210 A2 | 5/2007 |
| WO | WO2008/030369 A1 | 3/2008 |

OTHER PUBLICATIONS

Wermuth, C. G., "Molecular Variations Based on Isosteric Replacements", The Practice of Medicinal Chemistry, 1996, pp. 203-237.

* cited by examiner

*Primary Examiner* — Joseph Kosack
*Assistant Examiner* — Matthew Coughlin
(74) *Attorney, Agent, or Firm* — Maria V. Marucci

(57) ABSTRACT

The instant invention provides compounds of Formula II which are 5-lipoxygenase activating protein inhibitors.

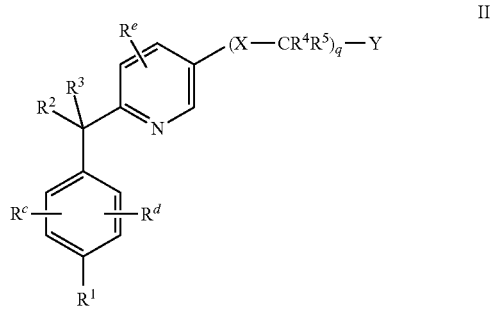

Compounds of Formula II are useful as anti-atherosclerotic, anti-asthmatic, anti-allergic, anti-inflammatory and cytoprotective agents.

17 Claims, No Drawings

DIARYL SUBSTITUTED ALKANES

CROSS REFERENCE TO RELATED APPLICATIONS

This application is a divisional application of U.S. Ser. No. 12/296,117, filed Oct. 6, 2008, which is a U.S. National Phase application under 35 U.S.C. §371 of PCT International Application No. PCT/US2007/008583, filed Apr. 6, 2007, which claims benefit of U.S. Provisional Application No. 60/790,958, filed Apr. 11, 2006.

FIELD OF THE INVENTION

The instant invention involves compounds that inhibit 5-lipoxygenase activating protein (FLAP), compositions containing such compounds and methods of treatment using such compounds for the treatment and prevention of atherosclerosis and related diseases and conditions.

BACKGROUND OF THE INVENTION

Inhibition of leukotriene biosynthesis has been an active area of pharmaceutical research for many years. Leukotrienes are potent contractile and inflammatory mediators derived through the oxygenation of arachidonic acid by 5-lipoxygenase.

One class of leukotriene biosynthesis inhibitors are those known to act through inhibition of 5-lipoxygenase (5-LO). In general, 5-LO inhibitors have been sought for the treatment of allergic rhinitis, asthma and inflammatory-conditions including arthritis. One example of a 5-LO inhibitor is the marketed drug zileuton, which is indicated for the treatment of asthma. More recently, it has been reported that 5-LO may be an important contributor to the atherogenic process; see Mehrabian, M. et al., Circulation Research, 2002 Jul. 26, 91(2):120-126.

A new class of leukotriene biosynthesis inhibitors (now known as FLAP inhibitors) distinct from 5-LO inhibitors is described in Miller, D. K. et al., "Identification and isolation of a membrane protein necessary for leukotriene production," Nature, vol. 343, No. 6255, pp. 278-281 (18 Jan. 1990). See also Dixon, R. A. et al, "Requirement of a 5-lipoxygenase-activating protein for leukotriene synthesis," Nature, vol 343, no. 6255, pp. 282-4 (18 Jan. 1990). 5-LO inhibitor compounds were used to identify and isolate the inner nuclear membrane 18,000 dalton protein 5-lipoxygenase-activating protein (FLAP). These compounds inhibit the formation of cellular leukotrienes but have no direct effect on soluble 5-LO activity. In cells, arachidonic acid is released from membrane phospholipids by the action of cytosolic phospholipase 2. This arachidonic acid is transferred to nuclear membrane bound 5-lipoxygenase by FLAP. The presence of FLAP in cells is essential for the synthesis of leukotrienes. Additionally, based on studies described in Helgadottir, A., et al., Nature Genetics, vol 36, no. 3 (March 2004) pp. 233-239, it is believed that the gene encoding 5-lipoxygenase activating protein confers risk for myocardial infarction and stroke in humans.

Despite significant therapeutic advances in the treatment and prevention of atherosclerosis and ensuing atherosclerotic disease events, such as the improvements that have been achieved with HMG-CoA reductase inhibitors, further treatment options are clearly needed. The instant invention addresses that need by providing compounds, compositions and methods for the treatment or prevention of atherosclerosis as well as related conditions.

SUMMARY OF THE INVENTION

The instant invention relates to compounds of structural Formula II, including for example those of structural Formula I, which are FLAP inhibitors, methods for their preparation, and methods and pharmaceutical formulations for using these compounds in mammals, especially humans.

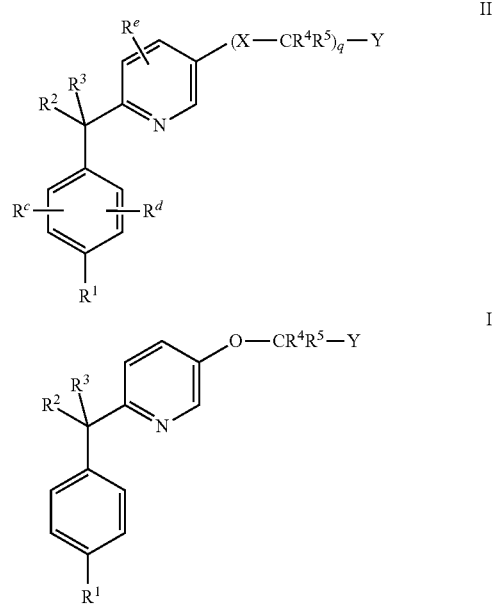

Therefore, this invention provides compounds of structural Formula II and the pharmaceutically acceptable salts thereof. Pharmaceutically acceptable esters and solvates of compounds encompassed by Formula II are also included within the scope of this invention. This invention also involves the use of compounds described herein to slow or halt atherogenesis. Therefore, one object of the instant invention is to provide a method for treating atherosclerosis, which includes halting or slowing the progression of atherosclerotic disease once it has become clinically evident, comprising administering a therapeutically effective amount of a compound of Formula II to a patient in need of such treatment. Another object is to provide methods for preventing or reducing the risk of developing atherosclerosis and atherosclerotic disease events, comprising administering a prophylactically effective amount of a compound of Formula II to a patient who is at risk of developing atherosclerosis or having an atherosclerotic disease event.

The compounds of Formula II are also useful as anti-asthmatic, anti-allergic, anti-inflammatory and cytoprotective agents. They are also useful in treating angina, cerebral spasm, glomerular nephritis, hepatitis, endotoxemia, uveitis, and allograft rejection. The instant invention provides methods of treatment comprising administering a therapeutically effective amount of a compound of Formula II to a patient in need of the above-described treatments.

A further object is to provide the use of FLAP inhibitors of Formula II in combination with other therapeutically effective agents, including other anti-atherosclerotic drugs. These and other objects will be evident from the description contained herein.

DETAILED DESCRIPTION OF THE INVENTION

The instant invention provides a compound represented by structural Formula II

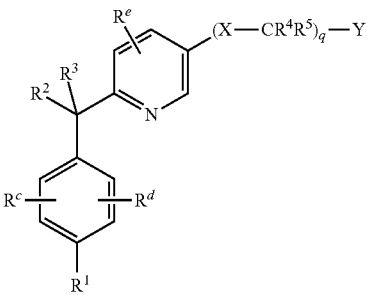

and the pharmaceutically acceptable salts thereof wherein:

q is an integer selected from 0 (zero) and 1 (one);

$R^1$ is selected from the group consisting of (a) a 5-membered aromatic or partially unsaturated heterocyclic ring containing 2 to 4 heteroatoms selected from N, S and O, wherein the heterocyclic ring is optionally substituted with $R^6$, (b) a 6-membered aromatic or partially unsaturated heterocyclic ring containing 1 to 2 heteroatoms selected from N and O, wherein the heterocyclic ring is optionally substituted with $R^6$;

(c) an 8-membered aromatic or partially unsaturated ortho-fused bicyclic ring system containing 3-5 heteroatoms selected from one sulfur and 2-4 of nitrogen wherein one carbon in the ring is optionally substituted with a group selected from =O, =S, —SMe, —$NH_2$, —$CF_3$, —Cl, —$C_{1-4}$alkyl and $C_{1-4}$alkyl substituted with a group selected from —$NH_2$, —OH, —$OC_{1-4}$alkyl, —CN and 1-3 of fluoro, and (d) a 9-membered aromatic or partially unsaturated ortho-fused bicyclic ring system containing 3-4 nitrogen atoms, wherein one carbon in the ring is optionally substituted with a group selected from =O, =S, —SMe, —$NH_2$, —$CF_3$, —Cl, —$C_{1-4}$alkyl and $C_{1-4}$alkyl substituted with a group selected from —$NH_2$, —OH, —$OC_{1-4}$ alkyl, —CN and 1-3 of fluoro;

(e) —$C_{1-6}$alkyl, —$C_{2-6}$alkenyl, and —$C_{2-6}$alkynyl, said alkyl, alkenyl and alkynyl groups being optionally substituted with $R^{12}$ and optionally substituted with $R^{13}$;

(f) —$C_{3-6}$ cycloalkyl optionally substituted with 1-3 substituents selected from the group consisting of fluoro, —$NH_2$, —OH and —$C_{1-3}$alkyl optionally substituted with 1-3 of fluoro;

(g) —O—$R^{6a}$; and (h) —H, —OH, —CN, —$CO_2R^4$, —$C(O)NR^7R^8$, —$NR^7R^8$, —$NR^bSO_pR^a$, —$NR^bC(O)R^a$, —$NR^bC(O)NR^aR^b$, —$S(O)_pR^a$, and —$S(O)_pNR^aR^b$;

p is an integer selected from 0, 1 and 2;

$R^2$ is selected from the group consisting of (a) —$C_{1-6}$alkyl optionally substituted with one or more substituents selected from the group consisting of —OH and fluoro (for example, 1-3 of fluoro), (b) —$C_{3-6}$ cycloalkyl optionally substituted with 1-3 of fluoro, and (c)

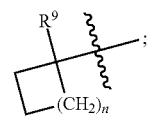

n is an integer selected from 0, 1, 2 and 3;

$R^3$ is selected from the group consisting of —H, —F, —OH, and —$C_{1-3}$alkyl optionally substituted with 1-5 fluoro (including for example —$CF_3$); or $R^2$ and $R^3$ are taken in combination and represent a mono- or bi-cyclic ring system containing 3 to 8 carbon atoms, said system being optionally substituted with 1-2 groups selected from: $C_{1-3}$alkyl, $OC_{1-3}$alkyl, F, OH, mono-, di- or tri-fluoro$C_{1-3}$alkyl and mono-, di- and tri-fluoro$C_{1-3}$alkoxy;

X is selected from the group consisting of and —O—, —S— and —$C(R^{14})_2$—, $R^4$ is selected from the group consisting of —H, —$C_{1-6}$alkyl and —$C_{3-6}$ cycloalkyl;

$R^5$ is selected from the group consisting of —H, —F, and —$CH_3$;

$R^6$ is selected from the group consisting of (a) —$C_{1-6}$alkyl optionally substituted with one or more substituents selected from the group consisting of —OH, —$NH_2$, —CN, —O—$C_{1-4}$alkyl and fluoro (for example, 1-3 of fluoro), (b) —$C_{1-6}$alkyl-$R^{10}$, (c) —$OC_{1-6}$alkyl optionally substituted with one or more substituents selected from the group consisting of —OH, —$NH_2$ and fluoro, (d) —$C_{3-6}$ cycloalkyl optionally substituted with one or more substituents selected from the group consisting of methyl, —OH, —$NH_2$, —$CF_3$ and fluoro, (e) —$NR^7R^8$, (f) —$SO_2C_{1-3}$alkyl, (g) —$CO_2$—$R^8$, (h) —OH, (i) =O (oxo), (j) —SH, (k) =S, (l) —SMe, (m) —Cl, (n) —$CF_3$, (o) —CN and (p) $R^{10}$;

$R^{6a}$ is selected from the group consisting of (1) —$C_{1-6}$alkyl optionally substituted with one or more substituents selected from the group consisting of $R^{12}$ and $R^{13}$, (2) —$C_{1-6}$alkyl-$R^{10}$ and (3) —$C_{3-6}$ cycloalkyl optionally substituted with one or more substituents selected from the group consisting of $R^{12}$ and $R^{13}$;

$R^7$ is selected from the group consisting of (a) —H, (b) —$C_{1-6}$alkyl optionally substituted with one or more substituents selected from the group consisting of —F, —$NH_2$ and —OH, (c) —$C_{3-6}$ cycloalkyl optionally substituted with one or more substituents selected from the group consisting of methyl, —$CF_3$, —F, —$NH_2$ and —OH, (d) —$COC_{1-6}$alkyl optionally substituted with one or more substituents selected from the group consisting of —F and —OH, (e) —$COC_{3-6}$ cycloalkyl optionally substituted with one or more substituents selected from the group consisting of methyl, —$CF_3$, —F, —$NH_2$ and —OH, and (f) a 4-6 membered saturated heterocyclic ring containing one N, wherein the ring is bonded to the nitrogen in —$NR^7R^8$ through a carbon atom in the ring, and wherein the ring is optionally substituted with one or more substituents selected from the group consisting of methyl, —$CF_3$, —F, —$NH_2$ and —OH;

$R^8$ is selected from the group consisting of (a) —H, (b) —$C_{1-6}$alkyl optionally substituted with one or more substituents selected from the group consisting of —F, —$NH_2$ and —OH, and (c) —$C_{3-6}$cycloalkyl optionally substituted with one or more substituents selected from the group consisting of methyl, —$CF_3$, —F, —$NH_2$ and —OH;

or R⁷ and R⁸ together represent —(CH₂)₃₋₅— which is bonded with the nitrogen to which R⁷ and R⁸ are attached to form a 4-6 membered ring, wherein the ring is optionally substituted with a substituent selected form the group consisting of —CH₃, —CF₃, —F and —OH;

R⁹ is selected from the group consisting of —H, —OH, —C₁₋₃alkyl and —F;

R¹⁰ is a heterocyclic ring selected from the group consisting of (a) azetidinyl optionally substituted with one or more of methyl, —F and —OH, (b) pyrrolidinyl optionally substituted with one or more of methyl, —F and —OH, (c) piperidinyl optionally substituted with one or more of methyl, —F and —OH and (d) morpholinyl optionally substituted with one or more of methyl, —F and —OH;

Y is selected from the group consisting of (a) a 5-membered aromatic or partially unsaturated heterocyclic ring containing 1 to 4 heteroatoms selected from 1 to 4 of N and zero to 1 of S, wherein the heterocyclic ring is optionally substituted with R¹¹, (b) a 6-membered aromatic or partially unsaturated heterocyclic ring containing 1 to 4 N heteroatoms, wherein the heterocyclic ring is optionally substituted with R¹¹, (c) a 9-membered bicyclic aromatic or partially unsaturated heterocyclic ring containing 1 to 4 N heteroatoms, wherein the heterocyclic ring is optionally substituted with R¹¹ and (d) a 10-membered bicyclic aromatic or partially unsaturated heterocyclic ring containing 1 to 4 N heteroatoms, wherein the heterocyclic ring is optionally substituted with R¹¹; and R¹¹ is selected from the group consisting of —F, —NH₂, —OH, —OC₃₋₄cycloalkyl, —C₁₋₃alkyl optionally substituted with 1-3 fluoro, and —OC₁₋₃alkyl optionally substituted with phenyl or 1-3 fluoro;

R¹² is selected from the group consisting of: —CO₂R⁴, —C(O)NR⁷R⁸, —N(Rᵃ)₂, —NRᵇSO₂Rᵃ, —NRᵇC(O)Rᵃ, —NRᵇC(O)NRᵃRᵇ, —S(O)ₚNRᵃRᵇ, —S(O)ₚRᵃ, —F, —CF₃, phenyl, Hetcy and Z¹, R¹³ is selected from the group consisting of —OH, —NH₂ and —F;

R¹⁴ is selected from the group consisting of —H and —C₁₋₄ alkyl optionally substituted with 1-3 fluoro groups;

each Rᵃ is independently selected from the group consisting of
a) —H,
b) —C₁₋₄alkyl, —C₂₋₄alkenyl and —C₂₋₄alkynyl, wherein each is optionally substituted with 1-2 substituents selected from the group consisting of: —OH, —OC₁₋₄ alkyl, —CN, —NH₂, —NHC₁₋₄alkyl, and —N(C₁₋₄ alkyl)₂, and —CF₃, and optionally with 1-3 of fluoro,
c) Hetcy and Hetcy-C₁₋₄alkyl-, the Hetcy moieties being optionally substituted on carbon with 1-2 substituents selected from the group consisting of —F, —OH, —CO₂H, —C₁₋₄alkyl, —CO₂C₁₋₄alkyl, —OC₁₋₄alkyl, —NH₂, —NHC₁₋₄alkyl, —N(C₁₋₄alkyl)₂, —NHC(O)C₁₋₄alkyl, oxo, —C(O)NHC₁₋₄alkyl and —C(O)N(C₁₋₄ alkyl)₂; and optionally substituted on nitrogen when present with a group selected from —C₁₋₄alkyl and —C₁₋₄acyl; and the alkyl portion of Hetcy-C₁₋₄alkyl- being optionally substituted with a member selected from the group consisting of —OH, —CN, —OC₁₋₄ alkyl, —NH₂, —NHC₁₋₄alkyl, —N(C₁₋₄alkyl)₂ and 1-3 of fluoro;
d) Z² and Z²—C₁₋₄alkyl-, the alkyl portion of Z²—C₁₋₄ alkyl- being optionally substituted with a substituent selected from the group consisting of —OH, —CN, —OC₁₋₄alkyl, —NH₂, —NHC₁₋₄alkyl, —N(C₁₋₄ alkyl)₂ and 1-3 of fluoro;

each Rᵇ is independently selected from the group consisting of —H and —C₁₋₃alkyl optionally substituted with 1-2 members selected from the group consisting of NH₂, —OH, —F, —CN and —CF₃;

Rᶜ, Rᵈ, and Rᵉ are each independently selected from —H, —F, —OH, —CN, —C₁₋₄alkyl optionally substituted with 1-3 of fluoro, and —OC₁₋₄alkyl optionally substituted with 1-3 of fluoro;

Hetcy is selected from the group consisting of azetidinyl, pyrrolidinyl, piperidinyl, piperazinyl, morpholinyl, tetrahydrofuranyl and β-lactamyl, δ-lactamyl, γ-lactamyl and tetrahydropyranyl;

Z¹ is selected from the group consisting of:
a) Z²,
b) an 8-membered aromatic or partially unsaturated ortho-fused bicyclic ring system containing 3-5 heteroatoms selected from one sulfur and 2-4 of nitrogen wherein one carbon in the ring is optionally substituted with a group selected from =O, =S, —SMe, —NH₂, —CF₃, —Cl, —C₁₋₄alkyl and C₁₋₄alkyl substituted with a group selected from —NH₂, —OH, —OC₁₋₄alkyl, —CN and 1-3 of fluoro, and
c) a 9-membered aromatic or partially unsaturated ortho-fused bicyclic ring system containing 3-4 nitrogen atoms, wherein one carbon in the ring is optionally substituted with a group selected from =O, =S, —SMe, —NH₂, —CF₃, —Cl, —C₁₋₄alkyl and C₁₋₄alkyl substituted with a group selected from —NH₂, —OH, —OC₁₋₄ alkyl, —CN and 1-3 of fluoro; and Z² is selected from the group consisting of:
a) a 5-membered aromatic or partially unsaturated heterocyclic ring containing 2-4 nitrogen atoms, wherein one nitrogen in the ring is optionally substituted with a group selected from —C₁₋₄alkyl and —C₁₋₄alkyl substituted with a group selected from —NH₂, —OH, —CN and 1-3 of fluoro, and one carbon in the ring is optionally substituted with a group selected from =O, =S, —SMe, —NH₂, —CF₃, —Cl, —C₁₋₄alkyl and —C₁₋₄ alkyl substituted with a group selected from —NH₂, —OH, —OC₁₋₄alkyl, —CN and 1-3 of fluoro,
b) a 5-membered aromatic or partially unsaturated heterocyclic ring containing 2-3 heteroatoms selected from one oxygen or one sulfur and 1-2 of nitrogen, wherein one nitrogen in the ring is optionally substituted with a group selected from C₁₋₄alkyl and C₁₋₄alkyl substituted with a group selected from —NH₂, —OH, —CN and 1-3 of fluoro, and one carbon in the ring is optionally substituted with a group selected from =O, =S, —SMe, —NH₂, —CF₃, —Cl, and C₁₋₄alkyl optionally substituted with a group selected from —NH₂, —OH, —OC₁₋₄alkyl, —CN and 1-3 of fluoro, and
c) a 6-membered aromatic or partially unsaturated heterocyclic ring containing 1-2 nitrogen atoms, wherein one nitrogen in the ring is optionally substituted with a group selected from —C₁₋₄alkyl and —C₁₋₄alkyl substituted with a group selected from —NH₂, —OH, —CN and 1-3 of fluoro, and one carbon in the ring is optionally substituted with a group selected from =O, =S, —SMe, —NH₂, —CF₃, —Cl, —C₁₋₄alkyl and —C₁₋₄ alkyl substituted with a group selected from —NH₂, —OH, —OC₁₋₄alkyl, —CN and 1-3 of fluoro.

In one embodiment of this invention are compounds of Formula II wherein q is one. Within this embodiment are compounds of Formula II wherein q is one and X is O or S.

The instant invention further provides a compound of Formula II represented by structural Formula I

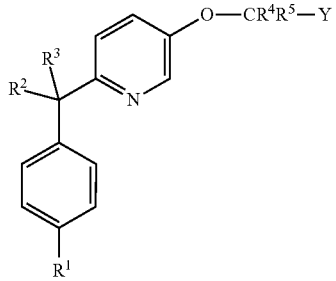

and the pharmaceutically acceptable salts thereof wherein:

$R^1$ is selected from the group consisting of (a) a 5-membered aromatic or partially unsaturated heterocyclic ring containing 2 to 4 heteroatoms selected from N, S and O, wherein the heterocyclic ring is optionally substituted with $R^6$, (b) a 6-membered aromatic or partially unsaturated heterocyclic ring containing 1 to 2 heteroatoms selected from N and O, wherein the heterocyclic ring is optionally substituted with $R^6$, and (c) —O—$R^{6a}$;

$R^2$ is selected from the group consisting of (a) —$C_{1-6}$alkyl optionally substituted with one or more substituents selected from the group consisting of —OH and fluoro, (b) —$C_{3-6}$cycloalkyl optionally substituted with 1-3 of fluoro, and

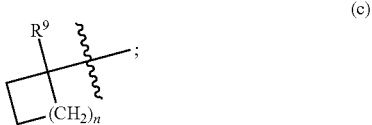

n is an integer selected from 0, 1, 2 and 3;

$R^3$ is selected from the group consisting of —H, —F, —OH, and —$C_{1-3}$alkyl optionally substituted with 1-5 fluoro, including, for example —$CF_3$;

$R^4$ is selected from the group consisting of —H, —$C_{1-4}$alkyl and —$C_{3-4}$ cycloalkyl;

$R^5$ is selected from the group consisting of —H and —$CH_3$; and $R^6$ is selected from the group consisting of (a) —$C_{1-6}$alkyl optionally substituted with one or more substituents selected from the group consisting of —OH, —$NH_2$ and 1-3 of fluoro, (b) —$C_{1-3}$ alkyl-$R^{10}$, (C) —$OC_{1-6}$alkyl optionally substituted with one or more substituents selected from the group consisting of —OH, —$NH_2$ and fluoro, (d) —$C_{3-6}$ cycloalkyl optionally substituted with one or more substituents selected from the group consisting of methyl, —OH, —$NH_2$, —$CF_3$ and fluoro, (e) —$NR^7R^8$, (f) —$SO_2C_{1-3}$alkyl (g) —$CO_2$—$R^8$, (h) oxo and (i) —CN;

$R^{6a}$ is selected from the group consisting of (a) —$C_{1-6}$alkyl optionally substituted with one or more substituents selected from the group consisting of —OH, —$NH_2$ and fluoro, (b) —$C_{1-3}$alkyl-$R^{10}$, and (c) —$C_{3-6}$ cycloalkyl optionally substituted with one or more substituents selected from the group consisting of —OH, —$NH_2$ and fluoro;

$R^7$ is selected from the group consisting of (a) —H, (b) —$C_{1-6}$alkyl optionally substituted with one or more substituents selected from the group consisting of —F and —OH, (c) —$C_{3-6}$ cycloalkyl optionally substituted with one or more substituents selected from the group consisting of methyl, —$CF_3$, —F, —$NH_2$ and —OH, (d) —$COC_{1-6}$alkyl optionally substituted with one or more substituents selected from the group consisting of —F and —OH, (e) —$COC_{3-6}$cycloalkyl optionally substituted with one or more substituents selected from the group consisting of methyl, —$CF_3$, —F, —$NH_2$ and —OH, and (f) a 4-6 membered saturated heterocyclic ring containing one N, wherein the ring is bonded to the nitrogen in —$NR^7R^8$ through a carbon atom in the ring, and wherein the ring is optionally substituted with one or more substituents selected from the group consisting of methyl, —$CF_3$, —F, —$NH_2$ and —OH;

$R^8$ is selected from the group consisting of (a) —H, (b) —$C_{1-6}$alkyl optionally substituted with one or more substituents selected from the group consisting of —F and —OH, and (c) —$C_{3-6}$cycloalkyl optionally substituted with one or more substituents selected from the group consisting of methyl, —$CF_3$, —F, —$NH_2$ and —OH;

$R^9$ is selected from the group consisting of —H, —$C_{1-3}$ alkyl and —F;

$R^{10}$ is selected from the group consisting of (a) azetidinyl optionally substituted with one or more of methyl, —F and —OH, (b) pyrrolidinyl optionally substituted with one or more of methyl, —F and —OH, (c) piperidinyl optionally substituted with one or more of methyl, —F and —OH, and (d) morpholinyl optionally substituted with one or more of methyl, —F and —OH; and Y is selected from the group consisting of (a) a 5-membered aromatic or partially unsaturated heterocyclic ring containing 1 to 4 heteroatoms selected from 1-4 of N and 0-1 of S, wherein the heterocyclic ring is optionally substituted with $R^{11}$, (b) a 6-membered aromatic or partially unsaturated heterocyclic ring containing 1 to 4 N heteroatoms, wherein the heterocyclic ring is optionally substituted with $R^{11}$, and (c) a 10-membered bicyclic aromatic or partially unsaturated heterocyclic ring containing 1 to 4 N heteroatoms, wherein the heterocyclic ring is optionally substituted with $R^{11}$; and $R^{11}$ is selected from the group consisting of —F, —$NH_2$, —OH, —$OC_{3-4}$cycloalkyl, —$C_{1-3}$alkyl optionally substituted with 1-3 fluoro, and —$OC_{1-3}$alkyl optionally substituted with phenyl or 1-3 fluoro.

In another embodiment of this invention are compounds of Formula I having structural Formula Ia:

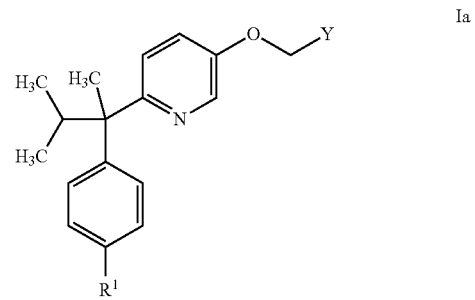

wherein the variables ($R^1$, Y, etc.) are as defined in Formula I, and the pharmaceutically acceptable salts thereof.

Within each of the embodiments defined by Formulas I and Ia is a first class of compounds wherein $R^1$ is selected from the group consisting of (a) a 5-membered aromatic or partially unsaturated heterocyclic ring containing a total of 2 to 4 heteroatoms selected from two to four of N, zero to one of O, and zero to one of S, wherein the heterocyclic ring is optionally substituted with $R^6$, (b) a 6-membered aromatic or partially unsaturated heterocyclic ring containing 1 to 2 heteroatoms selected from N and O, wherein the heterocyclic ring is optionally substituted with $R^6$, (c) —$C_{1-4}$alkyl optionally substituted with $R^{12}$, and particularly wherein $R^{12}$ is selected from Hetcy and $Z^1$, and optionally substituted with $R^{13}$, and particularly wherein $R^{13}$ is selected from —OH and —$NH_2$, (d) —$CO_2C_{1-6}$alkyl,
(e) —$C(O)NR^7R^8$,
(f) —CN, and
(g) —$C_{3-6}$ cycloalkyl optionally substituted with $R^{12}$, and particularly wherein $R^{12}$ is selected from Hetcy and $Z^1$, and optionally substituted with $R^{13}$, and particularly wherein $R^{13}$ is selected from —OH and —$NH_2$.

In a sub-class of the first class are compounds wherein $R^1$ is selected from the group consisting of:

(a) a 5-membered aromatic or partially unsaturated heterocyclic ring containing a total of 2 to 4 heteroatoms selected from two to four of N, zero to one of O, and Zero to one of S, wherein the heterocyclic ring is optionally substituted with $R^6$, and (b) a 6-membered aromatic or partially unsaturated heterocyclic ring containing 1 to 2 heteroatoms selected from N and O, wherein the heterocyclic ring is optionally substituted with $R^6$. In a sub-class of each first class are compounds wherein $R^1$ is selected from a 5-membered aromatic or partially unsaturated heterocyclic ring containing 2 to 4 heteroatoms selected from N and O, wherein the heterocyclic ring is optionally substituted with $R^6$. In a further sub-class of each first class are compounds wherein $R^1$ is selected from a 5-membered aromatic or partially unsaturated heterocyclic ring containing 2 to 4 heteroatoms selected from two to four of N, zero to one of O and zero to one of S, wherein the heterocyclic ring is optionally substituted with $R^6$, and particularly wherein $R^1$ is selected from:

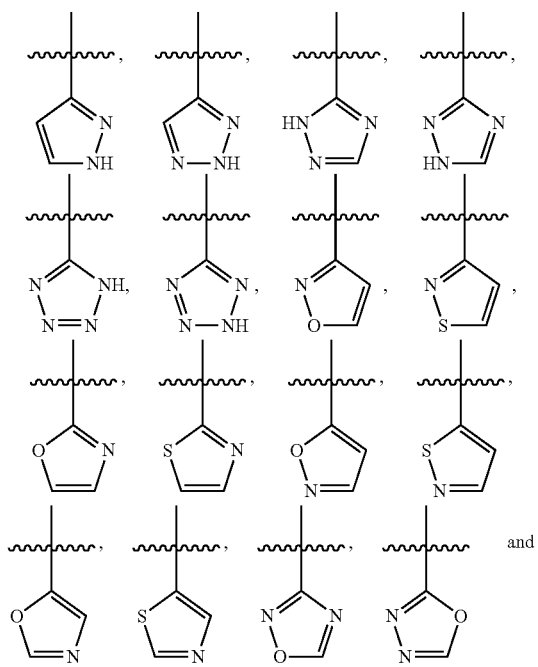

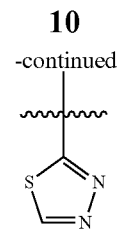

and is optionally substituted with $R^6$.

In another sub-class of each first class are compounds wherein $R^1$ is selected from a 6-membered aromatic or partially unsaturated heterocyclic ring containing 1 to 2 N heteroatoms, wherein the heterocyclic ring is optionally substituted with $R^6$, and particularly wherein $R^1$ is selected from:

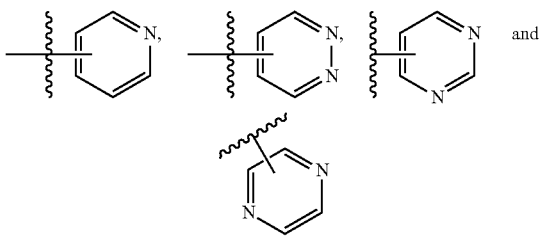

and is optionally substituted with $R^6$.

Within each of the embodiments defined by Formula II wherein q is one, and Formulas I and Ia, as well as within each of the first classes and sub-classes thereof is a second class of compounds wherein $R^6$, when present, is selected from the group consisting of:

(a) —$CR^xR^yR^z$ wherein $R^x$ is selected from —H, —$C_{1-3}$alkyl and —F, $R^y$ is selected from —H, —$C_{1-3}$-alkyl and —F, and $R^z$ is selected from —H, —$C_{1-3}$alkyl, —F, —$NH_2$ and —OH; or $R^x$ and $R^y$ are joined together with the carbon to which they are attached to form a cyclopropyl ring; (b) —$CH_2$—$R^{10}$, (c) —$OCH_3$ optionally substituted with 1-3 fluoro, (d) —$NR^7R^8$, (e) —$SO_2CH_3$ and (f) oxo.

In a sub-class of each second class of compounds are those wherein $R^6$ is selected from the group consisting of —$C(CH_3)_2$ OH,

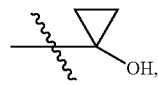

—$CH_3$, —$CF_3$ and —$CH_2$—$R^{10}$. Particularly $R^{10}$ is selected from

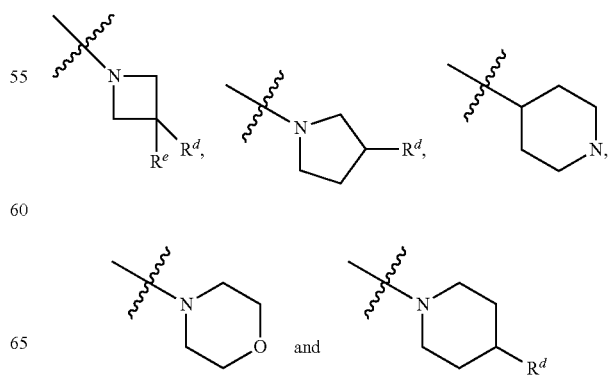

wherein $R^d$ is selected from —F and —OH, and $R^e$ is selected from —H, —F and —OH.

Within each of the embodiments defined by Formulas I and Ia, as well as within each of the first and second classes and sub-classes thereof defined above, is a third class of compounds wherein Y is selected from (a) a 5-membered aromatic or partially unsaturated heterocyclic ring containing 1 to 2 heteroatoms selected from 1 to 2 of N and zero to one of S, wherein the heterocyclic ring is optionally substituted with $R^{11}$, and (b) a 6-membered aromatic or partially unsaturated heterocyclic ring containing 1 to 2 N heteroatoms, wherein the heterocyclic ring is optionally substituted with $R^{11}$. In a sub-class of each third class of compounds are those wherein Y is selected from:

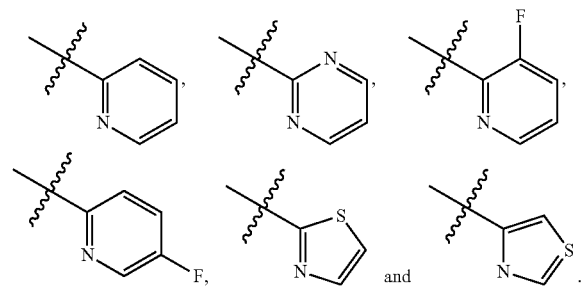

In another sub-class of each third class of compounds are those wherein Y is a 6-membered aromatic heterocyclic ring containing 1 to 2 N heteroatoms, wherein the heterocyclic ring is optionally substituted with $R^{11}$. Particularly, Y may be selected from:

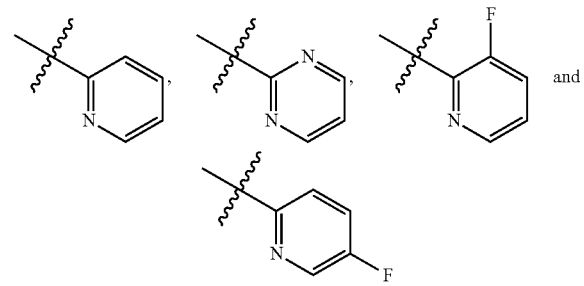

In still another sub-class of each third class of compounds are those wherein Y is a 5-membered aromatic or partially unsaturated heterocyclic ring containing one N and one S, and particularly is selected from:

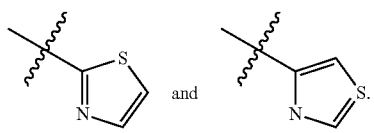

Within each of the embodiments defined by Formulas I and Ia, as well as within each of the first, second and third classes and sub-classes thereof defined above, is a fourth class of compounds wherein $R^{11}$ is —F or is absent (i.e., Y is unsubstituted).

Within the embodiments defined by each of Formula II wherein q is one and Formula I, as well as within each of the first, second, third and fourth classes and in each of any sub-classes thereof, is a fifth class of compounds wherein $R^2$ is selected from the group consisting of i-propyl, t-butyl, cyclopropyl, cyclobutyl,

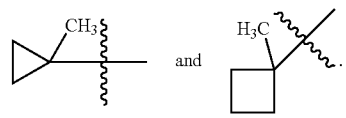

In a sub-class of each fifth class of compounds are those wherein $R^2$ is selected from i-propyl and t-butyl.

Within the embodiments defined by each of Formula II wherein q is one and Formula I, as well as within each of the first, second, third, fourth and fifth classes and in each of any sub-classes thereof, is a sixth class of compounds wherein $R^3$ is selected from the group consisting of —H and —$CH_3$. Particularly, when $R^3$ is —H, then $R^2$ is t-butyl; and when $R^3$ is —$CH_3$, then $R^2$ is i-propyl.

Within the embodiments defined by each of Formula II wherein q is one and Formula I, as well as within each of the first, second, third, fourth and sixth classes and in each of any sub-classes thereof, is a seventh class of compounds wherein $R^4$ is selected from the group consisting of —H, —$CH_3$ and —$CH_2CH_3$.

Within the embodiments defined by each of Formula II wherein q is one and Formula I, as well as within each of the first, second, third, fourth, fifth, sixth and seventh classes and sub-classes thereof, is an eighth class of compounds wherein $R^5$ is —H.

In another embodiment of this invention are compounds of Formula II wherein q is zero. The instant invention further provides a compound of Formula II represented by structural Formula IIa:

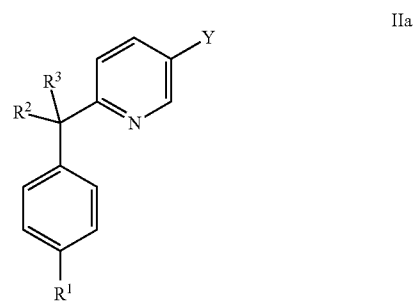

IIa wherein the variables ($R^1$, Y, etc.) are as defined in Formula II, and the pharmaceutically acceptable salts thereof.

In another embodiment of this invention are compounds of Formula IIa having structural Formula IIb:

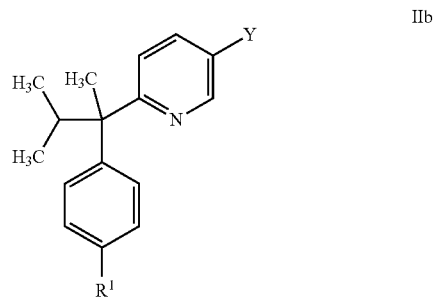

IIb wherein the variables ($R^1$, Y, etc.) are as defined in Formula II, and the pharmaceutically acceptable salts thereof.

Within each of the embodiments defined by Formula II wherein q is zero, Formulas IIa and IIb is a ninth class of compounds wherein Y is a 6-membered aromatic heterocyclic ring containing 1 to 2 N heteroatoms wherein the heterocyclic ring is optionally substituted with $R^{11}$. In a first subclass of each ninth class are compounds wherein Y is selected from:

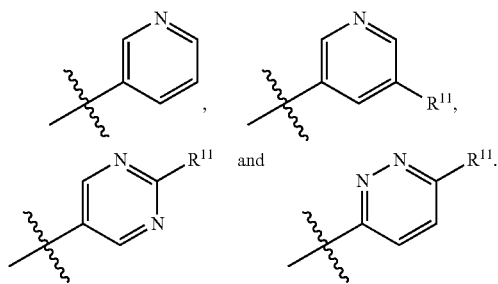

In a second subclass within each ninth class, Y is selected from:

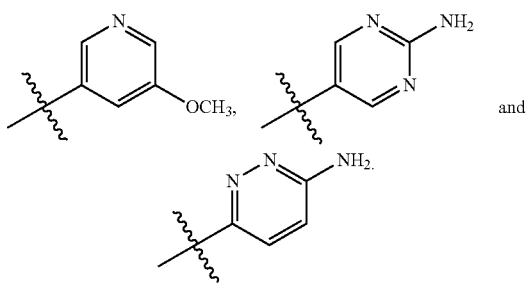

Within each of the embodiments defined by Formulas II, IIa and IIb, as well as within each of the ninth classes and sub-classes thereof, is a tenth class of compounds wherein $R^{11}$, when present, is selected from the group consisting of —$NH_2$ and —$OC_{1-3}$alkyl optionally substituted with phenyl or 1-3 of fluoro.

Within the embodiments defined by Formulas II wherein q is zero and IIa, as well as within each of the ninth and tenth classes and in each of any sub-classes thereof, is an eleventh class of compounds wherein $R^2$ is selected from the group consisting of i-propyl, t-butyl, cyclopropyl, cyclobutyl,

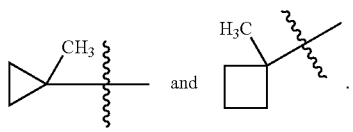

In a sub-class of each eleventh class of compounds are those wherein $R^2$ is selected from i-propyl and t-butyl.

Within the embodiments defined by Formulas II wherein q is zero and IIa, as well as within each of the ninth, tenth, and eleventh classes and in each of any sub-classes thereof, is a twelfth class of compounds wherein $R^3$ is selected from the group consisting of —H and —$CH_3$. In a further sub-class thereof are compounds wherein $R^3$ is —H when $R^2$ is t-butyl; and $R^3$ is —$CH_3$ when $R^2$ is i-propyl.

Within the embodiment defined by Formula II, as well as within any other embodiments wherein $R^c$, $R^d$ and $R^e$ are present, is a thirteenth class of compounds wherein $R^c$, $R^d$ and $R^e$ are each —H.

Within each of the embodiments defined by Formulas II, IIa and IIb, as well as within each of the ninth through thirteenth classes and sub-classes that are associated with the afore-mentioned Formulas, is a fourteenth class of compounds wherein $R^1$ is selected from the group consisting of:

(a) a 5-membered aromatic or partially unsaturated heterocyclic ring containing a total of 2 to 4 heteroatoms selected from two to four of N, zero to one of O, and zero to one of S, wherein the heterocyclic ring is optionally substituted with $R^6$, (b) a 6-membered aromatic or partially unsaturated heterocyclic ring containing 1 to 2 heteroatoms selected from N and O, wherein the heterocyclic ring is optionally substituted with $R^6$, (c) —$C_{1-4}$alkyl optionally substituted with $R^{12}$, and particularly wherein $R^{12}$ is selected from Hetcy and $Z^1$, and optionally substituted with $R^{13}$, and particularly wherein $R^{13}$ is selected from —OH and —$NH_2$, (d) —$OR^{6a}$ wherein $R^{6a}$ is —$C_{1-4}$alkyl optionally substituted with $R^{13}$, and particularly wherein $R^{13}$ is 1-5 of fluoro, (e) —$CO_2C_{1-6}$alkyl, (f) —$C(O)NR^7R^8$, (g) —CN, and (h) —$C_{3-6}$ cycloalkyl optionally substituted with $R^{12}$, and particularly wherein $R^{12}$ is selected from Hetcy and $Z^1$, and optionally substituted with $R^{13}$, and particularly wherein $R^{13}$ is selected from —OH and —$NH_2$.

In a first sub-class of each fourteenth class are compounds wherein $R^1$ is a 5-membered aromatic or partially unsaturated heterocyclic ring containing a total of 2 to 4 heteroatoms selected from two to four of N, zero to one of O, and zero to one of S, wherein the heterocyclic ring is optionally substituted with $R^6$, and particularly wherein $R^1$ is selected from:

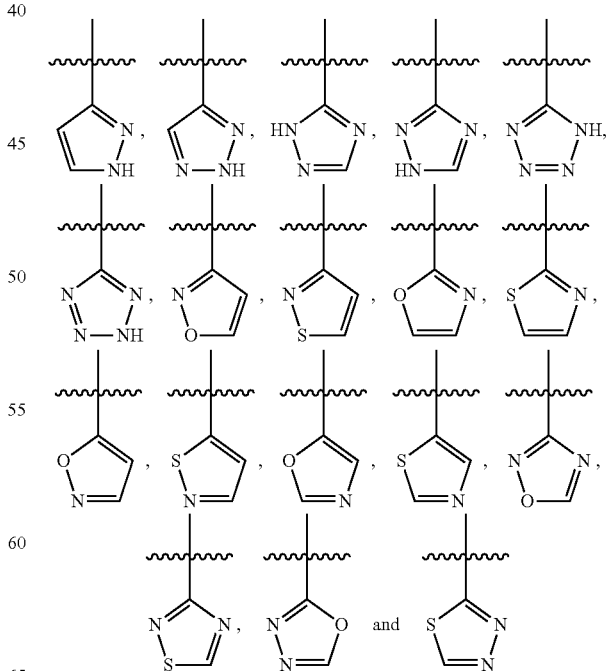

and is optionally substituted with $R^6$.

In second sub-class of each fourteenth class are compounds wherein $R^1$ is a 6-membered aromatic heterocyclic ring containing 1 to 2 N heteroatoms, wherein the heterocyclic ring is optionally substituted with $R^6$, and particularly wherein $R^1$ is selected from:

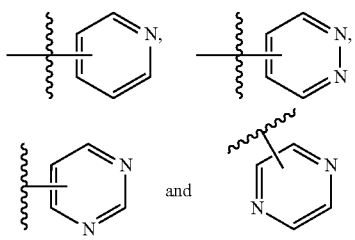

and is optionally substituted with $R^6$.

In a third sub-class of each fourteenth class are compounds wherein $R^1$ is selected from (a) —C(CH$_3$)$_2$OH, (b) —C(CH$_3$)$_2$NH$_2$ (c) —C$_{3-6}$ cycloalkyl optionally substituted with one or more substituents selected from the group consisting of —OH and —NH$_2$, (d) —OCH$_3$ optionally substituted with 1-3 of fluoro, (e) —CN, (f) —CO$_2$C$_{1-6}$alkyl, and (g) —C(O)NR$^7$R$^8$ wherein $R^8$ is —H and $R^7$ is selected from (i) —H, (ii) —C$_{1-6}$alkyl optionally substituted with one or more substituents selected from the group consisting of —F and —OH, (iii) —C$_{3-6}$ cycloalkyl optionally substituted with one or more substituents selected from the group consisting of —F and —OH, and (iv) a 4-6 membered saturated heterocyclic ring containing one N, wherein the ring is bonded to the nitrogen in —NR$^7$R$^8$ through a carbon atom in the ring, and wherein the ring is optionally substituted with one or more substituents selected from the group consisting of methyl, —CF$_3$, —F, —NH$_2$ and —OH.

Within each of the embodiments defined by Formula II wherein q is zero, and Formulas IIa and IIb, as well as within each of the ninth through fourteenth classes and sub-classes associated with any of the aforementioned Formulas, is a fifteenth class of compounds wherein $R^6$, when present, is selected from the group consisting of:

(a) —CR$^x$R$^y$R$^z$ wherein $R^x$ is selected from —H, —C$_{1-3}$alkyl and —F, $R^y$ is selected from —H, —C$_{1-3}$alkyl and —F, and $R^z$ is selected from —H, —C$_{1-3}$alkyl, —OC$_{1-3}$alkyl, —F, —NH$_2$ and —OH; or $R^x$ and $R^y$ are joined together with the carbon to which they are attached to form a cyclopropyl ring having the following structure

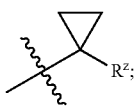

(b) —C$_{1-3}$ alkyl-R$^{10}$,
(c) —R$^{10}$,
(d) —OC$_{1-4}$alkyl optionally substituted with 1-5 fluoro,
(e) —NR$^7$R$^8$,
(f) —SO$_2$CH$_3$,
(g) oxo and
(h) —CO$_2$C$_{1-6}$alkyl.

In a sub-class of each fifteenth class of compounds are those wherein $R^6$ is selected from the group consisting of —C(CH$_3$)$_2$OH, —C(CH$_3$)$_2$NH$_2$, —CH$_2$OH,

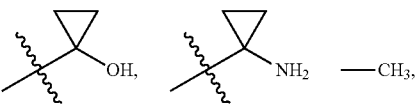

—CF$_3$, —CH$_2$—R$^{10}$, —CH(CH$_3$)—R$^{10}$, —C(CH$_3$)$_2$—R$^{10}$, —SO$_2$CH$_3$, and —NR$^7$R$^8$ wherein $R^7$ is selected from —H and —C$_{1-3}$alkyl, and $R^8$ is selected from —H, —C$_{1-3}$alkyl, and a 4-6 membered saturated heterocyclic ring containing one N, wherein the ring is bonded to the nitrogen in —NR$^7$R$^8$ through a carbon atom in the ring, and wherein the ring is optionally substituted with one or more substituents selected from the group consisting of methyl, —CF$_3$, —F, —NH$_2$ and —OH.

Within each of the embodiments defined by Formulas II, IIa and IIb, as well as within each of the ninth through fifteenth classes and sub-classes associated with any of Formulas II, IIa and IIb, is a sixteenth class of compounds wherein $R^{10}$ is selected from

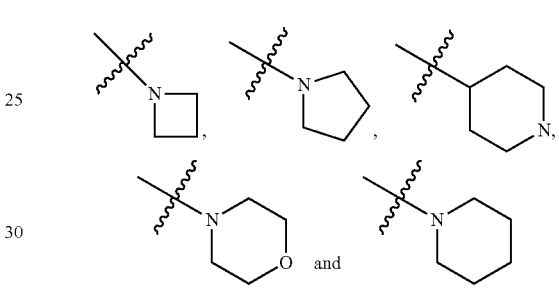

and is optionally substituted with a 1-2 substituents independently selected from —OH and fluoro.

Within each of the embodiments defined by Formulas II, IIa and IIb, as well as within each of the ninth through sixteenth classes and sub-classes associated with any of Formulas II, IIa and IIb, is a seventeenth class of compounds wherein $R^{12}$, when present, is Hetcy. In a further sub-class thereof are compounds wherein $R^{12}$ is absent.

Within each of the embodiments defined by Formulas II, IIa and IIb, as well as within each of the ninth through seventeenth classes and sub-classes associated with any of Formulas II, IIa and IIb, is an eighteenth class of compounds wherein $R^{13}$, when present, is —OH. In a further sub-class thereof, $R^{12}$ is absent and $R^{13}$ is —OH or is absent.

In compounds of Formula II, including those of Formulas I and IIa and all classes and subclasses thereof, when $R^2$ is i-propyl and $R^3$ is methyl, the (S)-enantiomer is preferred. Similarly, the (S)-enantiomers of Formulas Ia and IIb and all classes and subclasses thereof are preferred.

(S)-II

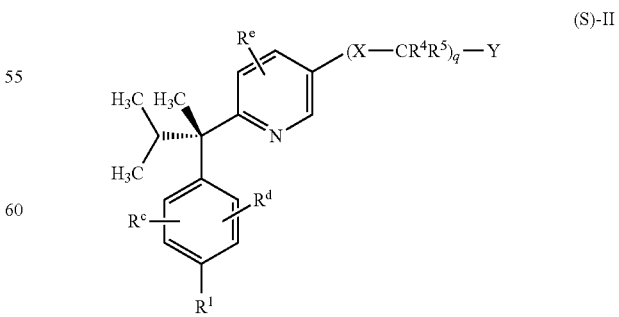

where $R^2$ = i-propyl
$R^3$ = methyl

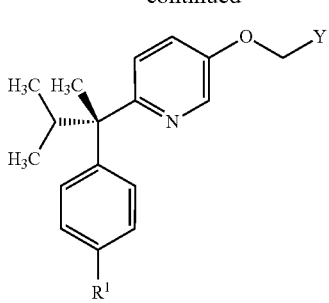

(S)-Ia

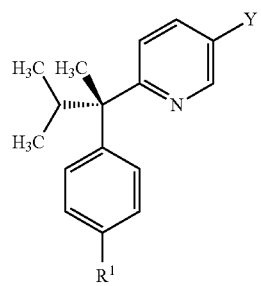

(S)-IIb

The term "alkyl" means carbon chains which may be linear or branched, or combinations thereof, containing the indicated number of carbon atoms. Examples of alkyl groups include methyl, ethyl, propyl, iso-propyl (i-propyl), butyl, sec- and tert-butyl (s-butyl, t-butyl), pentyl, hexyl, and the like. "Cycloalkyl" is intended to be a cyclized alkyl ring having the indicated number of carbon atoms Examples of cycloalkyl include cyclopropyl, cyclobutyl, cyclopentyl, and cyclohexyl. The cycloalkyl ring may be substituted on any available carbon which results in the creation of a stable structure, including the ring carbon which serves as the point of attachment to the rest of the molecule. Preferably, cycloalkyl is cyclopropyl or cyclobutyl, and more particularly, when it is substituted with —CH3 or —CF$_3$, the substituent is on the ring carbon which serves as the point of attachment to the rest of the molecule.

The terms "heterocycle" and derivatives thereof such as "heterocyclyl" and "heterocyclic ring" mean an aromatic, partially unsaturated or saturated ring containing one or more carbon atoms and one or more heteroatoms such as nitrogen, oxygen and sulfur, but may be more specifically defined where appropriate in the specification, for example with respect to degree of saturation, number of members (i.e. atoms) in the ring and/or the type and quantity of heteroatoms in the ring. The point of attachment in a compound structure may be via any carbon or nitrogen in the heterocyclic ring which results in the creation of a stable structure, unless specified otherwise. The heterocyclic ring may be substituted on any available carbon or nitrogen in the ring which results in the creation of a stable structure, unless specified otherwise.

The phrase "optionally substituted with one or more substituents" is intended to mean that the total number of substituents on the optionally substituted moiety overall may be zero, one or more than one, and that each carbon and heteroatom (when present) available for substitution in the given moiety may independently be unsubstituted or mono- or poly-substituted, with one or more substituents that are the same or different at each occurrence and which result in the creation of a stable structure. The term "poly-substituted" is intended to mean two or more substituents, e.g. di-, tri-, tetra-, pent-substitution and higher as appropriate, valence and stability permitting.

Some of the compounds encompassed herein may exist as tautomers, e.g., keto-enol tautomers. For the purpose of illustration, when $R^1$ is a 5-membered heterocyclic ring and $R^6$ is oxo, the resulting compound may be capable of tautomerism, as exemplified below:

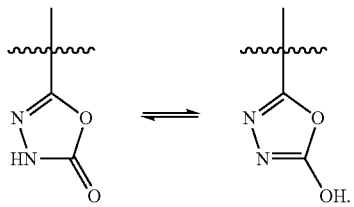 [SMILES: *c1n[nH]c(=O)o1 ; *c1nnc(O)o1]

Where compounds of this invention are capable of tautomerization, all individual tautomers as well as mixtures thereof are included in the scope of this invention.

Reference to compounds of "Formula II" herein also include compounds defined by the scope of each of the sub-generic descriptions such as Formulas I, Ia, IIa and IIb, as well as individual compounds within the scope of any of these sub-generic descriptions, unless in context a structural sub-group of compounds is being addressed as in, for example, the synthetic description of how to make certain compounds within a structural sub-group. Reference to the compounds of this invention as those of "Formula II," "Formula I," "Formula Ia," "Formula IIa," "Formula IIb," or any other generic structural formulas used herein is intended to encompass compounds falling within the scope of the structural Formula including pharmaceutically acceptable salts thereof. Pharmaceutically acceptable esters and solvates of compounds encompassed by Formula II are also included within the scope of this invention. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like, and particularly citric, fumaric, hydrobromic, hydrochloric, trifluoroacetic, maleic, phosphoric, sulfuric, and tartaric acids.

Reference to the compounds of this invention as those of "Formula II," "Formula I," "Formula Ia," "Formula IIa," "Formula IIb," or any other embodiments described herein is intended to encompass compounds falling within the scope of the structural Formula and also encompasses pharmaceutically acceptable esters thereof where such forms are possible. Pharmaceutically acceptable esters can optionally be made by esterification of an available carboxylic acid group or by formation of an ester on an available hydroxy group in a compound. Such esterified compounds may serve as prodrugs which can be hydrolyzed back to their acid or hydroxy form, particularly in vivo, and as such are encompassed within the scope of this invention. Examples of pharmaceutically acceptable esters include, but are not limited to, esters comprised of —$C_{1-4}$ alkyl and —$C_{1-4}$ alkyl substituted with phenyl.

The compounds of Formula II (including those of Formula I, Formula Ia, Formula IIa and Formula IIb) may contain one or more asymmetric centers, including chiral centers, and can thus occur as racemates, racemic mixtures e.g. enantiomeric mixtures, single enantiomers, diastereoisomeric mixtures and individual diastereoisomers. The present invention includes all such isomers, as well as salts, esters and solvates of such racemates, mixtures, enantiomers and diastereoisomers. Furthermore, some of the crystalline forms of compounds of the present invention may exist as polymorphs and as such all amorphous and crystalline forms are intended to be included within the scope of the present invention.

In addition, some of the compounds of Formula II (including those of Formula I, Formula Ia, Formula IIa and Formula IIb) of the instant invention may form solvates with water (known as a hydrate) or common organic solvents. Such pharmaceutically acceptable solvate compositions comprised of a compound of this invention and a solvent, including for example water, are likewise encompassed within the scope of this invention.

Compounds of structural Formula II may be separated into their individual diastereoisomers or enantiomers by, e.g., fractional crystallization from suitable solvents, e.g., DCM/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, synthesis can be performed using one or more chiral intermediates which results in a chiral final product.

The ability of the compounds of this invention to inhibit biosynthesis of the leukotrienes makes them useful for preventing or reversing the symptoms induced by the leukotrienes in a human subject. Accordingly, this invention provides a method for preventing the synthesis, the action, or the release of leukotrienes in a mammal which comprises administering to said mammal a FLAP inhibitory effective amount of a compound of this invention. Such FLAP inhibitory activity can be measured using the FLAP Assay described herein. Since leukotrienes are potent inflammatory mediators, also provided is method of treating an inflammatory condition in a mammal which comprises administering a therapeutically effective amount of a compound of this invention to a mammal in need of such treatment.

The inhibition of the mammalian biosynthesis of leukotrienes also indicates that the compounds and pharmaceutical compositions thereof are useful to treat, prevent or ameliorate atherosclerosis in mammals, and especially in humans. Therefore, the compounds of Formula II can be used for the treatment of atherosclerosis comprising administering a therapeutically effective amount of a compound of Formula II to a patient in need of such treatment. A further aspect of this invention involves a method for preventing or reducing the risk of developing atherosclerosis, comprising administering a prophylactically effective amount of a compound of Formula II to a patient in need of such treatment, for example, a patient who is at risk of developing atherosclerosis.

Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A FLAP inhibitor may be administered to prevent or reduce the risk of occurrence, or recurrence where the potential exists, of a coronary heart disease (CHD) event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a FLAP inhibitor to a patient at risk for such an event. The patient may already have atherosclerotic disease at the time of administration, or may be at risk for developing it.

The method of this invention particularly serves to prevent or slow new atherosclerotic lesion or plaque formation, and to prevent or slow progression of existing lesions or plaques, as well as to cause regression of existing lesions or plaques. Accordingly, one aspect of this invention encompassed within the scope of treatment of atherosclerosis involves a method for halting or slowing the progression of atherosclerosis, including halting or slowing atherosclerotic plaque progression, comprising administering a therapeutically effective amount of a FLAP inhibitor to a patient in need of such treatment. This method also includes halting or slowing progression of atherosclerotic plaques existing at the time the instant treatment is begun (i.e., "existing atherosclerotic plaques"), as well as halting or slowing formation of new atherosclerotic plaques in patients with atherosclerosis.

Another aspect of this invention encompassed within the scope of treatment of atherosclerosis involves a method for regression of atherosclerosis, including regression of atherosclerotic plaques existing at the time the instant treatment is begun, comprising administering a therapeutically effective amount of a FLAP inhibitor to a patient in need of such treatment. Another aspect of this invention involves a method for preventing or reducing the risk of atherosclerotic plaque rupture comprising administering a prophylactically effective amount of a FLAP inhibitor to a patient in need of such treatment.

The ability of the compounds of Formula II to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to prevent or reduce the risk for, treat or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, 16) multiple sclerosis, 17) proliferation of myoblastic leukemia cells, 18) pulmonary fibrosis, 19) respiratory syncytial virus, 20) acne and 21) sleep apnea. Moreover, the compounds of this invention can be administered to patients, including adult and pediatric patients, for the relief of symptoms of allergic rhinitis, including seasonal allergic rhinitis.

Particularly, the compounds of this invention can be administered to patients, including adult and pediatric patients, for the prophylaxis of asthma and for chronic treatment of asthma. The compounds of this invention can be administered to patients, including adult and pediatric patients, for the treatment of asthma: (1) as an alternative to low-dose inhaled corticosteroids (ICS) for patients with mild persistent asthma, (2) as concomitant therapy with low-dose inhaled corticosteroids (ICS) for patients with mild persistent asthma, or (3) as concomitant therapy in patients with persistent asthma who are inadequately controlled on inhaled corticosteroids (ICS) or on combined ICS/long-acting beta-agonist (LABA) therapy. The compounds can be used for treatment of asthmatic patients including, but not limited to, steroid resistant/non-responder asthmatics, asthmatics for whom leukotriene modifiers have previously failed, smoking asthmatics, and aspirin sensitive asthmatics.

The compounds can be administered to patients to: (1) improve FEV1 (Forced Expitory Volume in one minute), (2) improve morning and evening PEF (Peak Expitory flow), (3) reduce beta-agonist use (measured by puffs/day), (4) reduce inhaled/systemic steroid use. (5) improve daytime asthma symptoms, (6) reduce number of nocturnal awakenings, 7) improve asthma control days, (8) reduce number of asthma exacerbations, wherein an exacerbation is defined as: requiring systemic steroid, an emergency room visit, hospitalization, an unscheduled asthma related doctor visit, decrease in A.M. PEF by >20% or A.M. PEF <180 l/min, increased SABA (short-acting beta-agonist) use >70% from baseline (minimum increase 2 puffs), or increased symptom score of >50%, (9) reduce the number of asthma attacks (measured as % of days with at least one attack over a specified period of total days), wherein the attack is one that requires systemic steroid use, an emergency room visit, hospitalization, or an unscheduled asthma related doctor visit, (10) reduce the number of acute asthma attacks, (11) reduce blood and sputum eosinophils, and/or (12) prevent and treat EIB (exercised induced bronchoconstriction).

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also act as inhibitors of tumor metastasis and exhibit cytoprotective action.

The FLAP inhibitors of this invention can also be administered for prevention, amelioration and treatment of glomerulonephritis (see Guasch A., Zayas C. F., Badr K F. (1999), "MK-591 acutely restores glomerular size selectivity and reduces proteinuria in human glomerulonephritis," Kidney Int., 56:261-267); and also for and prevention, amelioration and treatment of kidney damage resulting from diabetes complications (see Valdivielso J M, Montero A., Badr K F., Munger K A. (2003), "Inhibition of FLAP decreases proteinuria in diabetic rats," J. Nephrol., 16(1):85-940.)

In addition, the compounds of this invention can also be used for the treatment of chronic obstructive pulmonary disease (COPD). As described in S. Kilfeather, Chest, 2002, vol 121, 197, airway neutrophilia in COPD patients is believed to be a contributing source of inflammation and is associated with airway remodeling. The presence of neutrophils is mediated in part by $LTB_4$, and treatment with the instant compounds could be used to reduce neutrophilic inflammation in patients with COPD and reduce the rate of COPD exacerbations. In particular, the compounds of this invention could be used for daily, preferably once-daily, maintenance treatment of airflow obstruction associated with COPD, including chronic bronchitis and emphysema.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like. Two assays can be used to measure cytoprotective ability. These assays are: (A) an ethanol-induced lesion assay and (B) an indomethacin-induced ulcer assay and are described in EP 140,684.

In particular, the compounds of the invention would be useful to reduce the gastric erosion caused by co-administration of a cyclooxygenase-2 selective inhibitor and low-dose aspirin. Cyclooxygenase-2 selective inhibitors are widely used as effective anti-inflammatory drugs with less potential for gastrointestinal complications as compared to traditional, non-selective non-steroidal anti-inflammatory drugs. However, the combined use of a cyclooxygenase-2 selective inhibitor with low-dose aspirin for cardio protection may compromise the gastrointestinal safety of this class of compounds. By virtue of its activity as a 5-lipoxygenase inhibitor, the compounds of the invention would be expected to be gastric protective in this regard. See Fiorucci, et al. FASEB J. 17:1171-1173, 2003. Cyclooxygenase-2 selective inhibitors for use with the invention include but are not limited to etoricoxib (ARCOXIA™) and celecoxib (CELEBREX®). A compound of this invention in combination with a cyclooxygenase-2 selective inhibitor could be administered in unit dosage form or separately to a patient on low-dose aspirin therapy. Alternatively, the cyclooxygenase-2 inhibitor could be administered in unit dosage form with low-dose aspirin, in which case a compound of this invention would be administered separately. All three active ingredients in unit dosage form is also encompassed. Conventional dosage amounts of the cyclooxygenase-2 selective inhibitor and aspirin (for cardio protection) may be utilized. Aspirin could be administered at 81 mg once daily.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of onset of atherosclerosis.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment to slow progression of existing atherosclerosis, and a prophylactically effective amount, e.g., for prevention of an atherosclerotic disease event or formation of new lesions.

In general, FLAP inhibitors can be identified as those compounds which have an $IC_{50}$ in the "FLAP Binding Assay" that is less than or equal to 1 μM, and preferably 500 nM or less, more preferably 100 nM or less, and most preferably 25 nM or less.

An effective amount of a FLAP inhibitor in the method of this invention is in the range of about 0.01 mg/kg to about 30 mg/kg of body weight per day, preferably 0.1 mg to about 15 mg per kg, and most preferably 0.5 to 7.5 mg per kg, in single or divided doses. A single daily dose is preferred but not necessary. For an average body weight of 70 kg, the dosage level is therefore from about 1 mg to about 2000 mg of drug per day, e.g. 10 mg, 25 mg, 50 mg, 75 mg, 100 mg, 125 mg, 150 mg, 175 mg, 200 mg, 250 mg or 500 mg per day, preferably given as a single daily dose or in divided doses two to four times a day, or in sustained release form. It will be understood, however, that the specific dose level for any particular patient will depend upon a variety of factors including the age, body weight, general health, sex, diet, time of administration, route of administration, rate of excretion, drug combination and the severity of the patient's condition. A consideration of these factors is well within the purview of the ordinarily skilled clinician for the purpose of determining the therapeutically effective or prophylactically effective dosage amount needed to prevent, counter, or arrest the progress of the condition. It is expected that the FLAP inhibitor will administered chronically on a daily basis for a length of time appropriate to treat or prevent the medical condition relevant to the patient, including a course of therapy lasting months, years or the life of the patient.

One or more additional active agents may be administered with a compound of Formula II. The term "additional active agent (or agents)" is intended to mean a pharmaceutically active agent (or agents) different from the compound of Formula II. In a broad embodiment, any suitable additional active agent or agents, including but not limited to anti-atherosclerotic agents such as a lipid modifying compound, anti-diabetic agents and/or anti-obesity agents, and agents used for the treatment of metabolic syndrome, may be used in combination with the compound of Formula II in a single dosage formulation, or may be administered to the patient in a separate dosage formulation, which allows for concurrent or sequential administration of the active agents. The additional active agent or agents may have more than one pharmaceutical activity, for example it may have both lipid-modifying effects and anti-diabetic activity. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), pravastatin, particularly the sodium salt thereof (see U.S. Pat. No. 4,346,227), fluvastatin particularly the sodium salt thereof (see U.S. Pat. No. 5,354,772), atorvastatin, particularly the calcium salt thereof (see U.S. Pat. No. 5,273,995), pitavastatin also referred to as NK-104 (see PCT international publication number WO 97/23200) and rosuvastatin (CRESTOR®; see U.S. Pat. No. 5,260,440); 5-lipoxygenase inhibitors; cholesterol ester transfer protein (CETP) inhibitors, for example JTT-705 and torcetrapib, also known as CP529,414; HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; niacin; niacin receptor agonists such as acipimox and acifran, as well as niacin receptor partial agonists; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABCA1 gene expression; FXR and LXR ligands including both inhibitors and agonists; bisphosphonate compounds such as alendronate sodium; and cyclooxygenase-2 inhibitors such as etoricoxib, celecoxib and valdecoxib.

Other advantageous pharmaceutical combinations comprise the compounds of this invention in combination with anti-cholinergics such as ipratropium bromide and tiotropium, bronchodilators such as the beta agonist salbutamol, metaproterenol, terbutaline, fenoterol, salmeterol, formoterol and the like, and the anti-asthmatic drugs theophylline, choline theophyllinate and enprofylline, the calcium antagonists nifedipine, diltiazem, nitrendipine, verapamil, nimodipine, felodipine, etc., and the corticosteroids, hydrocortisone, methylprednisolone, betamethasone, dexamethasone, beclomethasone, and the like.

Particularly, for the prophylaxis and treatment of asthma, compounds of this invention can be used in combination with orally inhaled corticosteroids, such as beclomethasone (e.g. QVAR® Inhalation Aerosol), budesonide (e.g. Pulmicort Respules), flunisolide (e.g., AEROBID® and AEROBID®-M Inhaler System), fluticasone (e.g., FLOVENT® DISKUS® inhalation powder, FLOVENT® HFA Inhalation Aerosol), mometasone (e.g., ASMANEX® TWISTHALER®), and triamcinolone (e.g., AZMACORT® Inhalation Aerosol), and also with inhaled corticosteroid/LABA products such as fluticasone propionate/salmeterol (e.g., ADVAIR DISKUS®). The instant compounds could also be used in combination with leukotriene receptor antagonists such as montelukast (e.g., SINGULAIR®); phosphodiesterase 4 (PDE4) inhibitors such as roflumilast, N-Cyclopropyl-1-[3-(1-oxido-3-pyridinylethynyl)phenyl]-1,4-dihydro[1,8]naphthyridin-4-one-3-carboxamide and the compounds disclosed in PCT Publication WO2003/018579; and Very Late Antigen 4 (VLA4) inhibitors such as the compounds disclosed in U.S. Pat. No. 6,229,011, particularly R411 (N-(2-Chloro-6-methylbenzoyl)-4-[(2,6-dichlorobenzoyl)amino]-L-phenylalanine-2-(diethylamino)ethyl ester which is an ester pro-drug of the active moiety, N-(2-chloro-6-methylbenzoyl)-4-[(2,6-dichlorobenzoyl)amino]-L-phenylalanine), and the compounds disclosed in PCT publication WO2006/023396.

Still another type of agent that can be used in combination with the compounds of this invention are cholesterol absorption inhibitors. Cholesterol absorption inhibitors block the movement of cholesterol from the intestinal lumen into enterocytes of the small intestinal wall. This blockade is their primary mode of action in reducing serum cholesterol levels. These compounds are distinct from compounds which reduce serum cholesterol levels primarily by mechanisms of action such as acyl coenzyme A—cholesterol acyl transferase (ACAT) inhibition, inhibition of triglyceride synthesis, MTP inhibition, bile acid sequestration, and transcription modulation such as agonists or antagonists of nuclear hormones. Cholesterol absorption inhibitors include but are not limited to those described in U.S. Pat. Nos. 5,846,966, 5,631,365, 5,767,115, 6,133,001,5,886,171, 5,856,473, 5,756,470,5,739,321,5,919,672, 6,498,156, US2004/0082561, US2004/0067913, US2004/0063929, US2002-0137689, WO 05/047248, WO 05/021497, WO 05/021495, WO 05/000353, WO 04/005247, WO 00/63703, WO 00/60107, WO 00/38725, WO 00/34240, WO 00/20623, WO 97/45406, WO 97/16424, WO 97/16455, and WO 95/08532. An exemplary cholesterol absorption inhibitor is ezetimibe, marketed in the U.S. under the tradename ZETIA® described in U.S. Pat. No. Re 37721 and the Physician's Desk Reference.

This and other cholesterol absorption inhibitors can be identified according to the assay of hypolipidemic compounds using the hyperlipidemic hamster described in U.S. Patent Re 37721, beginning in column 20, in which hamsters are fed a controlled cholesterol diet and dosed with test compounds for seven days. Plasma lipid analysis is conducted and data is reported as percent reduction of lipid versus control.

Therapeutically effective amounts of cholesterol absorption inhibitors include dosages of from about 0.01 mg/kg to about 30 mg/kg of body weight per day, preferably about 0.1 mg/kg to about 15 mg/kg. For an average body weight of 70 kg, the dosage level is therefore from about 0.7 mg to about 2100 mg of drug per day, e.g. 10, 20, 40, 100 or 200 mg per day, preferably given as a single daily dose or in divided doses two to six times a day, or in sustained release form. This dosage regimen may be adjusted to provide the optimal therapeutic response when the cholesterol absorption inhibitor is used in combination with a compound of the instant invention.

In the method of treatment of this invention, the FLAP inhibitors may be administered via any suitable route of administration such as orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred.

For oral use, the pharmaceutical compositions of this invention containing the active ingredient may be in forms such as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Oral immediate-release and time-controlled release dosage forms may be employed, as well as enterically coated oral dosage forms. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. One example of a time-controlled release device is described in U.S. Pat. No. 5,366,738. They may also be coated by the technique described in U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The instant invention also encompasses a process for preparing a pharmaceutical composition comprising combining a compound of Formula II with a pharmaceutically acceptable carrier. Also encompassed is the pharmaceutical composition which is made by combining a compound of Formula II with a pharmaceutically acceptable carrier.

A therapeutically effective amount of a compound of Formula II can be used for the preparation of a medicament useful for treating or preventing any of the medical conditions described herein, in dosage amounts described herein. For example, a compound of Formula II can be used for the preparation of a medicament useful for preventing or reducing the risk of developing atherosclerotic disease, halting or slowing the progression of atherosclerotic disease once it has become clinically manifest, and preventing or reducing the risk of a first or subsequent occurrence of an atherosclerotic disease event. Additionally, the medicament may be useful for the treatment of asthma, allergies and allergic conditions, inflammation, COPD or erosive gastritis. The medicament comprised of a compound of Formula II may also be prepared with one or more additional active agents, such as those described herein.

The compounds of structural Formula II of the present invention can be prepared according to the procedures of the following Schemes and Examples, using appropriate materials and are further exemplified by the specific examples which follow. Moreover, by utilizing the procedures described herein, one of ordinary skill in the art can readily prepare additional compounds of the present invention claimed herein. The compounds illustrated in the examples are not, however, to be construed as forming the only genus that is considered as the invention. All temperatures are degrees Celsius unless otherwise noted. Mass spectra (MS) were measured by electron-spray ion-mass spectroscopy (ES-MS).

The instant compounds are generally isolated in a pharmaceutically acceptable form which can either be the free base or an appropriate salt derivative, such as those described above. The free amine bases corresponding to the isolated salts can be generated by neutralization with a suitable base, such as aqueous sodium hydrogencarbonate, sodium carbonate, sodium hydroxide, or potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization.

Some abbreviations used herein are as follows:

ABCA1 is adenosyltriphosphate-binding cassette-family A1; Ac is acetyl; AIBN is 2,2'-azobis(2-methylpropionitrile); aq. is aqueous; Ar is Aryl; Bn is benzyl; Boc is tertbutylcarbamoyl; br is broad; Bu is butyl; $^tBu$ is tert-butyl; celite is Celite® diatomaceous earth; cpm is counts per minute; δ is chemical shift; DCM is dichloromethane; d is doublet; DEAD is diethylazodicarboxylate; DIAD is diisopropylazodicarboxylate; DIPEA is diisopropylethylamine; DMAP is 4-dimethylaminopyridine; DMF is N,N-dimethylformamide; dppf is 1,1'-bis(diphenylphosphino)ferrocene; DMSO is dimethyl sulfoxide; EDC is N-(3-dimethylaminopropyl)-N'-ethylcarbodiimide hydrochloride; EDTA is ethylendiamine tetraacetic acid; equiv. is equivalent(s); ES-MS is electrospray ion-mass spectroscopy; Et is ethyl; $Et_2O$ is diethyl ether; EtOH is ethanol, EtOAc is ethyl acetate; FXR is farnesoid X receptor; g is gram; h is hours; HetAr or HAR is Heteroaryl; HATU is O-(7-azabenzotriazol-1-yl)-N,N,N',N'-tetramethyluronium hexafluorophosphate; HMG-CoA is 3-hydroxy-3-methyl-glutaryl coenzyme A; $^1$HNMR is proton nuclear magnetic resonance; HOAt is 1-hydroxy-7-azabenzotriazole; HOBt is 1-hydroxybenzotriazole; HPLC is high performance liquid chromatography; Hz is hertz; i is Iso; $IC_{50}$ is concentration at which 50% inhibition exists; J is internuclear coupling constant; kg is kilogram; LG is leaving group; $LTB_4$ is leukotriene $B_4$; LXR is liver X receptor; m is multiplet; M is molar; Me is methyl; m.p. is melting point; mg is milligram; μg is microgram; MeCN is acetonitrile; MeOH is methanol; MHz is megahertz; min is minute; mL is milliliter; mm is millimeter; μL is microliter; mM is milimolar; μM is micromolar; mmol is milimoles; Ms is methanesulfonyl; MS is mass spectrum, and a mass spectrum obtained by ES-MS may be denoted herein by "ES"; m/z is mass to charge ratio; n is normal; N is normal (unless in context it is referring to nitrogen); nm is nanometer; nM is nanomolar; NMM is N-methylmorpholine; NMO is N-methylmorpholine-N-oxide; NMP is N-methylpyrrolidin-2-one; $^n$Pr is n-propyl; p is pentet; p is para; PEG is polyethylene glycol; Ph is phenyl; Phth is phthalimidoyl; PPARα is peroxisome proliferator activated receptor alpha; Pr is propyl; iPr is isopropyl; p-TSA is para-toluenesulfonic acid; PyBOP is benzotriazole-1-yloxy-tris-pyrrolidino-phosphonium hexafluorophosphate; q is quartet; rt is room temperature; s is singlet; sec is secondary; t is triplet; $^t$BuOH is tert-butanol; tert is tertiary; Tf is trifluoromethanesulfonyl; TFA is trifluoroacetic acid; and THF is tetrahydrofuran; Ts is tosyl; UV is ultraviolet; x g is times gravity; ° C. is degrees Celsius.

The following reaction schemes illustrate the methods employed in the synthesis of the compounds of the present invention of structural Formula U. All abbreviations are as defined above unless indicated otherwise.

Reaction scheme A illustrates a preferred method of synthesis of a compound type 10. In this method, a ketone or aldehyde of type 1 is treated with an organometallic reagent of type 2, capable of transferring an aryl group, to afford a compound of type 3. Preferred organometallic reagents for effecting this transformation include organolithium (2, M=Li) and organomagnesium (2, M=Mg; Grignard) compounds. When organolithium reagents are employed, the reaction can be conducted in a variety of solvents, such as hexanes or diethyl ether or the like, at temperatures between −78° C. and rt. When Grignard reagents are employed as shown in scheme A, it is customary to conduct the reaction in a suitable ethereal solvent such as THF or diethyl ether, or mixtures thereof, at temperatures between −78° C. and the boiling temperature of the solvent. The organolithium and Grignard reagents are commonly purchased from commercial sources, but can be prepared synthetically according to known methods of organic synthesis. The resulting alcohol 3 can be treated with a protected aminomethylfuran derivative of type 4 in an electrophilic aromatic substitution process generally referred to as a Friedel Crafts arylation reaction. The preferred protecting group for the amino functionality in 4 as depicted in scheme A is phthalimide, but is by no means limited to such a group. Typical conditions for performing the arylation of 3 include the generation of an intermediate carbocation of type 5 derived from 3, followed by in situ trapping with a suitable aromatic coupling partner of type 4 to afford a product of type 6. It is customary to conduct the reaction in the presence of either suitable Bronstead acids such as tetrafluoboric acid or the like, or Lewis acids such as boron trifluoride or the like (*J. Am. Chem. Soc.* 2005, 127, 9348-9349). The reaction may also be performed in the presence of a variety of inert organic solvents, such as dichloromethane or 1,2-dichloroethane or the like, at temperatures typically between −78° C. and P. Preferred conditions for removal of the phthalimide protecting group involve treatment of 6 with reagents such as sodium methoxide or hydrazine or n-butylamine, in solvents such as MeOH or EtOH, at temperatures typically between it and the boiling temperature of the solvent. The product of the reaction is an amine of type 7 which can be transformed to a compound of type 8 in the presence of a suitable activating reagent, such as bromine or iodine. The reaction can be conducted in a variety of aqueous solvent mixtures that include solvents such as MeOH or EtOH or the like, at temperatures between rt and −20° C. The product 8 can be elaborated to a compound of type 10 by treatment with an appropriate alkylating agent. Usually, the reaction is performed in the presence of a suitable base such as potassium carbonate or cesium carbonate or the like, in a polar aprotic solvent such as DMF, at temperatures between −20° C. and 50° C. (*Acta Chem. Scand.* 1956, 10, 1603-1605). The product of the reaction is 10, which can be further elaborated to other compounds of the present invention (I).

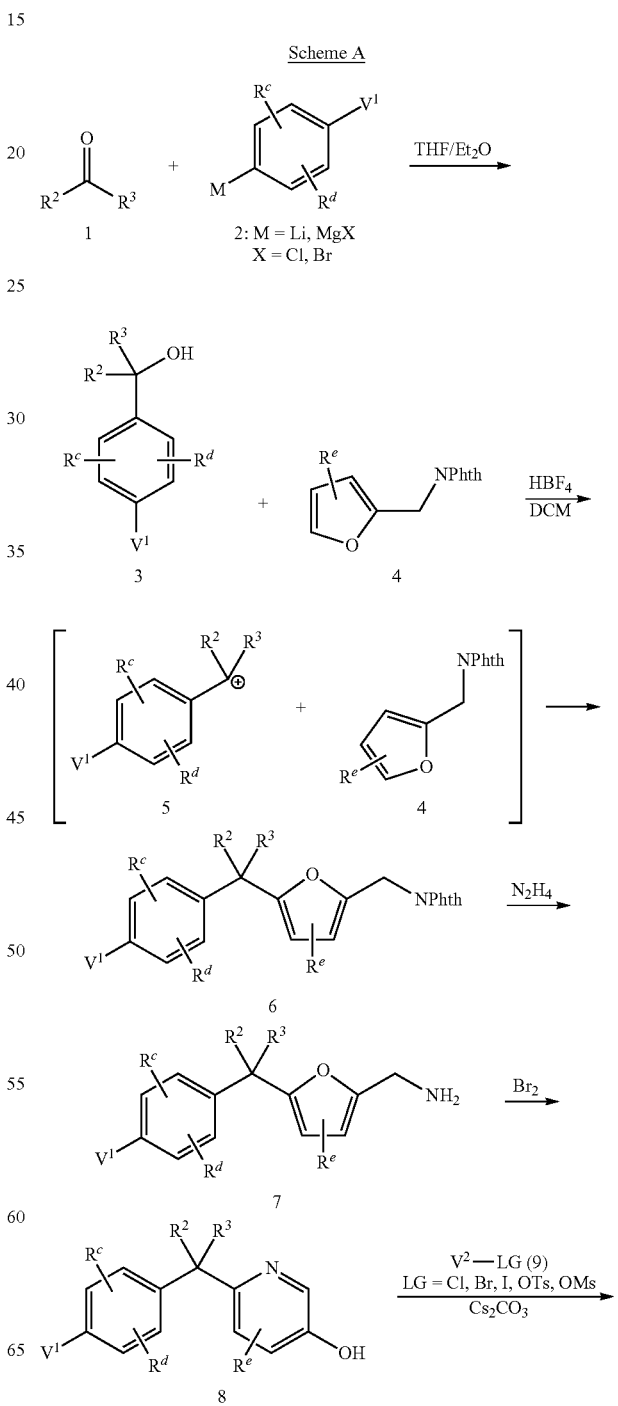

Scheme A

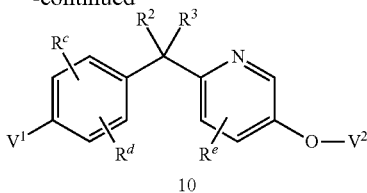

V¹ = R¹ as defined in formula I or a group that can be converted to R¹
V² = ―― CR⁴R⁵ ― Y as defined in formula I
or a group that can be converted to
―― CR⁴R⁵ ― Y Reaction scheme B illustrates a preferred method of synthesis of a compound of type 18. In this method, an acid chloride derivative of type 11, often generated from the respective carboxylic acid precursor using methods known to those skilled in the art of organic synthesis, is treated with an organometallic reagent of type 12 or type 13 to afford a product of type 14. Preferred organometallic reagents for effecting this transformation include organomagnesium (Grignard) and organozinc compounds. When Grignard reagents (12) are employed, the preferred conditions are similar to those described in scheme A. When organozinc reagents (13) are employed, the reaction is generally conducted in the presence of a suitable organotransition metal catalyst such as bis(triphenylphosphino)palladium(II) dichloride or copper(I) chloride or the like, in a variety of solvents such as THF or diethyl ether, at temperatures between −20° C. and rt (*Chem. Rev.* 1993, 93, 2117-2188). The Grignard and organozinc reagents are commonly purchased from commercial sources, but can be prepared synthetically according to known methods of organic synthesis. The resulting ketone 14 can then be treated with an organometallic reagent of type 2 under similar conditions to those described in scheme A to furnish a product of type 15. The hydroxyl group in 15 can be removed in a reaction sequence commonly referred to as the Barton-McCombie Deoxygenation strategy (*J. Chem. Soc., Perkin Trans.* 11975, 1574-1585). The reaction process requires initial activation of the hydroxyl moeity, which is achieved via alkylation of this group with a reagent such as phenyl thionochloroformate, in the presence of a suitable tertiary amine base such as pyridine, to afford a thiocarbonate derivative of type 16. Acylations of this type can be conducted in a variety of inert organic solvents such as dichloromethane or 1,2-dichloroethane, at temperatures typically between −20° C. and rt. Alternatively, a xanthate derivative of type 17 may also be prepared, often by a three step sequence involving treatment of 15 with a base such as sodium hydride or potassium hydride, followed by introduction of carbon disulfide, and finally, in situ alkylation with an agent such as methyl iodide. Xanthate formation is generally performed in an ethereal solvent such as THF or diethyl ether, at temperatures typically between −20° C. and it. Deoxygenation of 16 or 17 can be effected with a reducing agent such as a trialkyltin hydride, often in the presence of a free radical initiator such as AIBN or the like. Reactions of this type are performed in an inert organic solvent such as benzene or toluene or dimethoxyethane, that has been appropriately degassed, and at temperatures often corresponding to the boiling temperature of the solvent. It may be preferable to use an additive, such as potassium iodide or tetrabutylammonium iodide or the like, to accelerate or promote the reaction. The product is a compound of type 18, which can be elaborated to compounds of the present invention (I).

Scheme B

R² ― MgX (12)
X = Cl, Br
or
R² ― ZnX (13)
X = Br, I
―――――
Pd(PPh₃)₂Cl

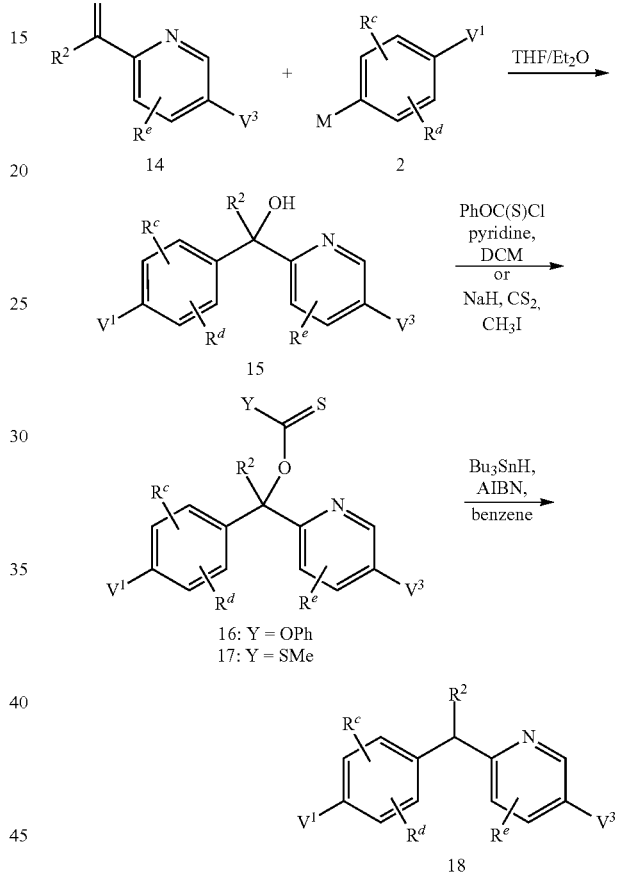

V³ = ――(X ― CR⁴R⁵)_q ― Y, as defined in formula I,
or a group that can be converted
to ――(X ― CR⁴R⁵)_q ― Y Reaction scheme C illustrates a preferred method for the elaboration of a compound of type 19 to afford a compound of type 20. In this method, 19 is treated with MeOH in the presence of a suitable palladium catalyst, such as [1,1′-bis (diphenylphosphino)ferrocene]dichloropalladium(II) or the like, and a tertiary amine base such as triethylamine or diisopropylethylamine or the like, in an inert organic solvent like DMF. The reaction is usually conducted at elevated temperature, typically between 50° C. and 100° C., for periods of 3-24 h, under an atmosphere of carbon monoxide (*J. Org. Chem.* 1974, 39, 3318-3326). In certain cases, it may be preferable to use elevated pressures of carbon monoxide, or an additive, such as lithium chloride, to promote or accelerate the reaction. The product of the reaction is an ester of type 20, which can be elaborated to compounds of the present invention (I).

Scheme C

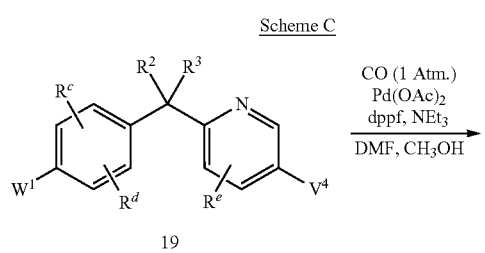

19

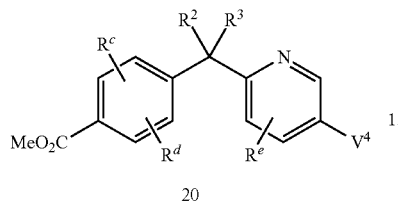

20

$W^1$ = Br or I
$V^4$ = OH or ——$(X—CR^4R^5)_q$—Y, as defined in formula I, or a group that can be converted to ——$(X—CR^4R^5)_q$—Y Reaction scheme D illustrates a preferred method for the elaboration of a compound type 19 to afford a compound of type 21. In this method, 19 is treated with a cyanide source such as potassium cyanide or trimethylsilylcyanide or the like, in the presence of a suitable palladium catalyst/ligand reagent system. It may be preferable to use an inorganic additive such as a copper(I) salt and/or a base such as triethylamine to accelerate or promote the reaction. It is customary to conduct the reaction in inert organic solvent, preferably a dipolar aprotic solvent, such as DMF or NMP or MeCN, at elevated reaction temperatures typically between 50-140° C., for a period of 3-24 hours. The product of the reaction is a nitrile of type 21, which can be elaborated to compounds of the present invention (I).

Scheme D

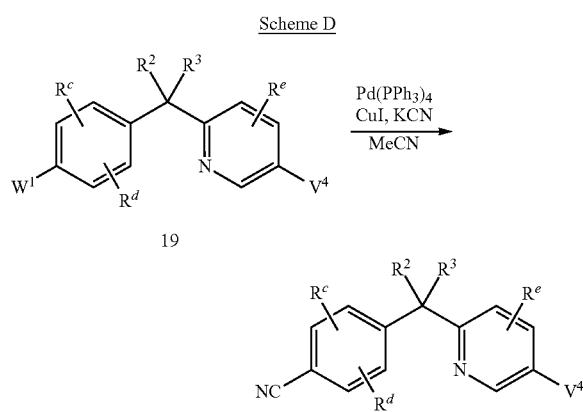

Reaction scheme E illustrates a preferred method of synthesis of compounds of structural formula 24. In this method, commonly referred to as the Suzuki reaction, a compound of type 19 can be treated with an aryl- or heteroaryl-coupling partner of type 22 or type 23, in the presence of a suitable palladium catalyst, such as [1,1'-bis(diphenylphosphino) ferrocene]dichloropalladium(II) or tetrakistriphenylphosphine-palladium(0) or the like, and a base such as aqueous sodium carbonate or aqueous tribasic sodium phosphate or the like (*Pure Appl. Chem.* 1991, 63, 419-422). The reaction is usually performed in an inert organic solvent such as a toluene-EtOH mixture or dioxane, at temperatures above rt, for a period of 3-24 h. Recent advancements in the Suzuki reaction have allowed this type of transformation to be conducted in many cases at rt (for example, see: *J. Am. Chem. Soc.* 2000, 122, 4020-4028 and references cited therein).

Scheme E

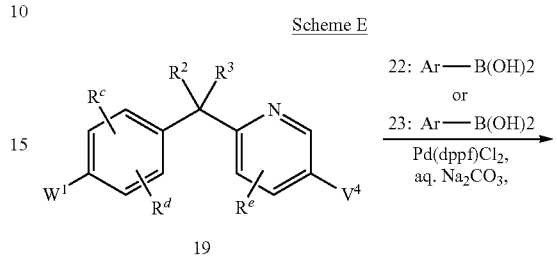

19

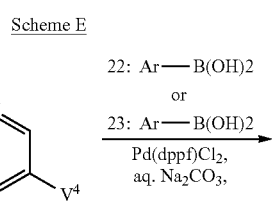

24

Reaction scheme F illustrates an alternative method of synthesis of compounds of structural formula 24. In this method, a compound of type 19 is treated with bis(pinacolato)diboron in the presence of a suitable palladium catalyst, such as [1,1'-bis(diphenylphosphino)ferrocene]dichloropalladium (II) and an auxiliary nucleophile such as potassium acetate or the like. The reaction is generally conducted in an inert organic solvent, such as DMSO or dioxane or the like, at elevated temperatures generally between 70° C. and 100° C., for a period of 1-24 h (*J. Org. Chem.* 1995, 60, 7508-7510). The product of this reaction is an intermediate boronate of type 25, which can participate in organotransition metal catalyzed cross-coupling reactions such as the aforementioned Suzuki reaction (scheme E) to afford compounds of the present invention (I).

Scheme F

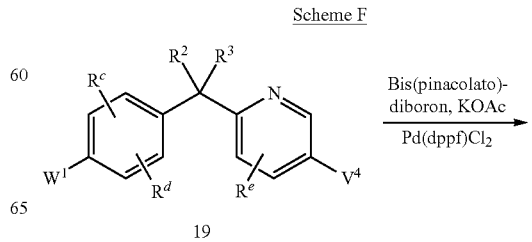

19

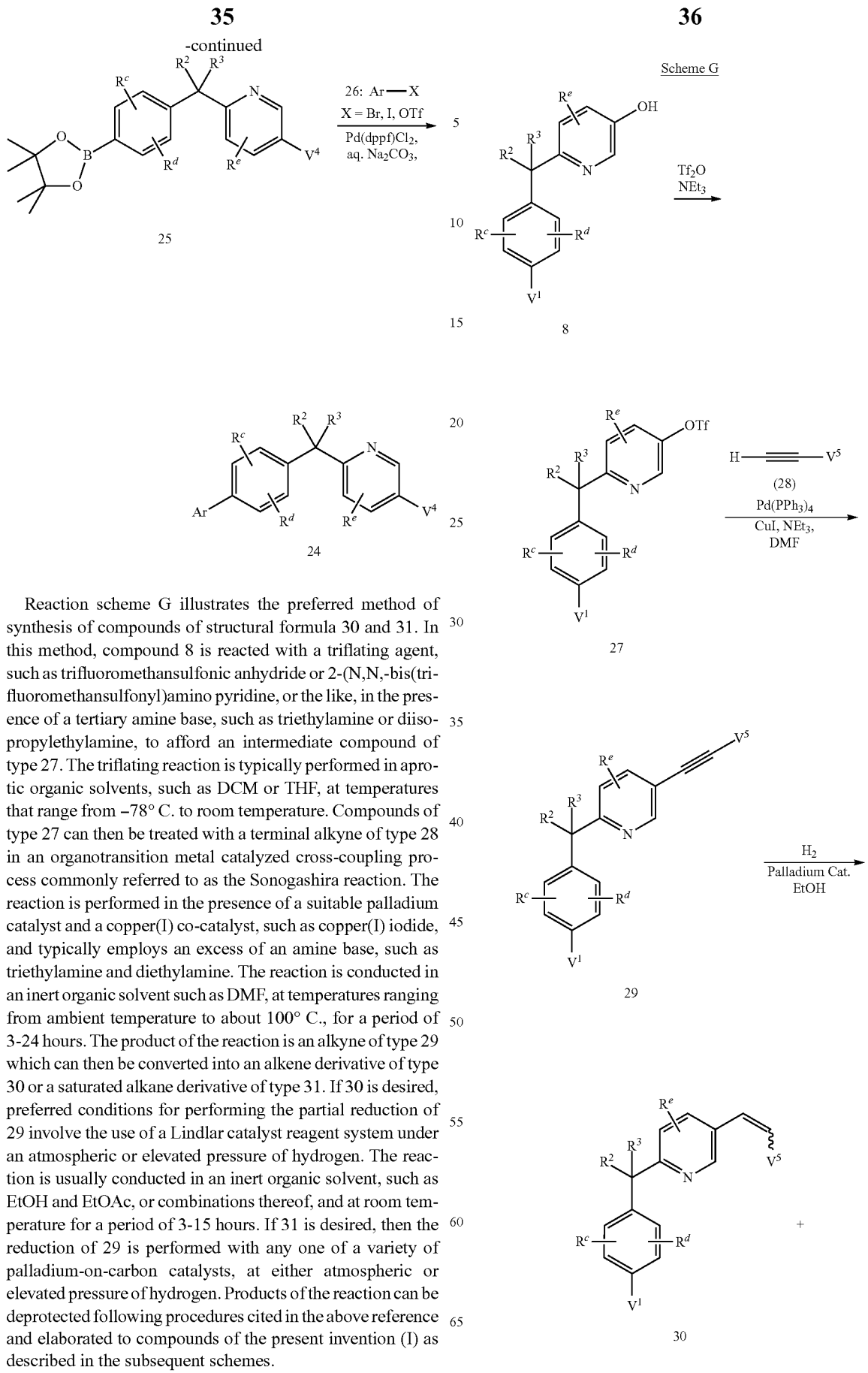

Reaction scheme G illustrates the preferred method of synthesis of compounds of structural formula 30 and 31. In this method, compound 8 is reacted with a triflating agent, such as trifluoromethansulfonic anhydride or 2-(N,N,-bis(trifluoromethansulfonyl)amino pyridine, or the like, in the presence of a tertiary amine base, such as triethylamine or diisopropylethylamine, to afford an intermediate compound of type 27. The triflating reaction is typically performed in aprotic organic solvents, such as DCM or THF, at temperatures that range from −78° C. to room temperature. Compounds of type 27 can then be treated with a terminal alkyne of type 28 in an organotransition metal catalyzed cross-coupling process commonly referred to as the Sonogashira reaction. The reaction is performed in the presence of a suitable palladium catalyst and a copper(I) co-catalyst, such as copper(I) iodide, and typically employs an excess of an amine base, such as triethylamine and diethylamine. The reaction is conducted in an inert organic solvent such as DMF, at temperatures ranging from ambient temperature to about 100° C., for a period of 3-24 hours. The product of the reaction is an alkyne of type 29 which can then be converted into an alkene derivative of type 30 or a saturated alkane derivative of type 31. If 30 is desired, preferred conditions for performing the partial reduction of 29 involve the use of a Lindlar catalyst reagent system under an atmospheric or elevated pressure of hydrogen. The reaction is usually conducted in an inert organic solvent, such as EtOH and EtOAc, or combinations thereof, and at room temperature for a period of 3-15 hours. If 31 is desired, then the reduction of 29 is performed with any one of a variety of palladium-on-carbon catalysts, at either atmospheric or elevated pressure of hydrogen. Products of the reaction can be deprotected following procedures cited in the above reference and elaborated to compounds of the present invention (I) as described in the subsequent schemes.

Scheme I

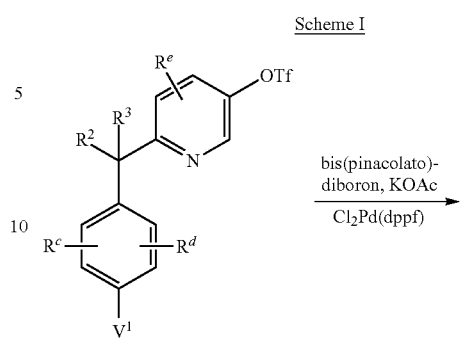

27

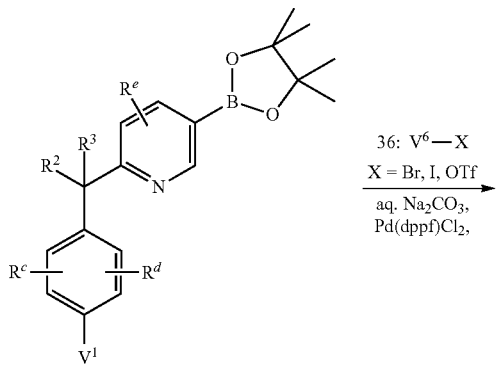

35

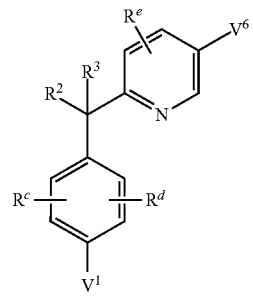

34

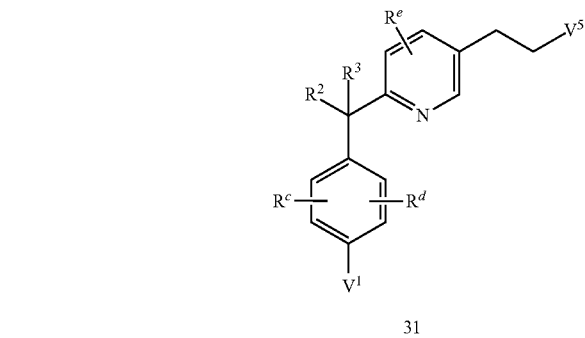

31

$V^5$ = Y as defined in formula I or a group that can be converted to Y

Reaction scheme H illustrates a preferred method of synthesis of compounds of structural formula 34 following methods similar to those previously described in Scheme E. Compounds of type 34 that are derived from inputs of type 32 or 33 that contain additional functional groups can be elaborated in numerous ways known in organic synthesis to furnish other compounds of the present invention (I).

Scheme H

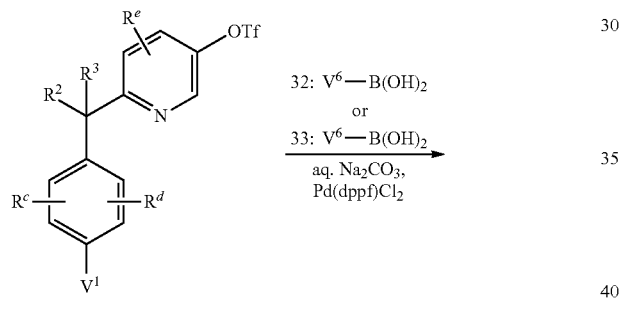

27

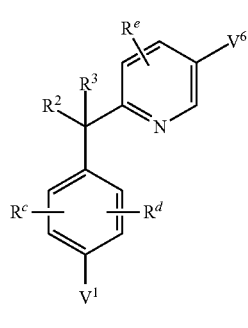

34

$V^6$ = Y as defined in formula I, or a group that can be converted to Y

Reaction scheme I illustrates a preferred method of synthesis of compounds of structural formula 34 following methods similar to those previously described in Scheme E.

Reaction scheme J illustrates a preferred method of synthesis of compounds of type 37. In this method, a compound of type 20 can be hydrolyzed to a carboxylic acid of type 37 using a variety of methods known to those skilled in organic synthesis. The product carboxylic acid 37 can be used as directed in reaction scheme H or synthetically modified using a variety of methods known in organic synthesis to afford compounds of the present invention (I).

Scheme J

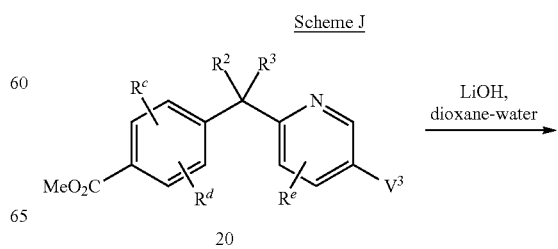

20

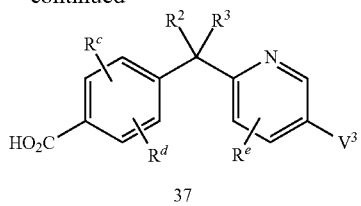

37

Reaction scheme K illustrates the preferred method of synthesis of compounds of structural formula 39, 40 and 41. In this method, 38 is treated with either allyltributylstannane or vinyltributylstannane in the presence of a suitable a palladium catalyst such as [1,1'-bis(diphenylphosphino)-ferrocene]dichloropalladium(II), in an inert organic solvent like DMF or NMP. The reaction is usually conducted at elevated temperatures, typically between 50-120° C., for periods of 2-24 hours. In certain cases, it may be essential to use an additive such as lithium chloride to promote the reaction. Often, the reaction times can be significantly reduced if the reaction is conducted under microwave irradiation. The product of the reaction is an alkene of structural formula 39 which can be synthetically elaborated, using a variety of methods known in organic synthesis. For example, 39 can be oxidatively cleaved to afford an aldehyde of type 40, which can be further oxidized to a carboxylic acid derivative of structural formula 41. A preferred method for the oxidative cleavage reaction is the two-step process shown in reaction scheme I. Alkene 39 is first oxidized to a vicinal diol using catalytic osmium tetraoxide in the presence of a stoichiometric reoxidant such as NMO, in a solvent system such as acetone-water. The intermediate vicinal diol which forms is generally not isolated, but is in turn subjected to cleavage with sodium periodate in a suitable mixed solvent system like THF-water to afford 40. Both steps in the oxidative cleavage sequence are generally completed during periods of several minutes to a few hours, at temperatures between 0° C. and room temperature. Aldehyde 40 can then be further oxidized to 41 using a buffered chlorite oxidation system. In this method, 40 is treated with sodium chlorite and monobasic sodium phosphate in the presence of a chlorine scavenger, such as 2-methyl-2-butene. The reaction is conducted typically in a solvent system like n-butanol-water, for periods of 1-6 hours, at temperatures between 0° C. and room temperature. In certain cases, 40 can be directly converted to 41 using the sodium periodate/ruthenium trichloride reagent system. Both 40 and 41 can be elaborated in numerous ways known in organic synthesis to furnish other compounds of the present invention (I).

Scheme K

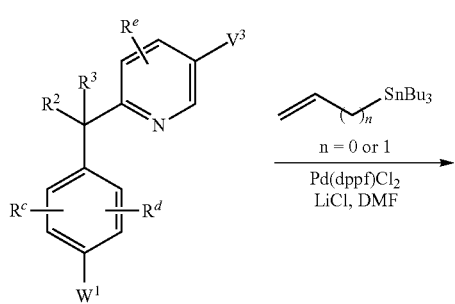

38

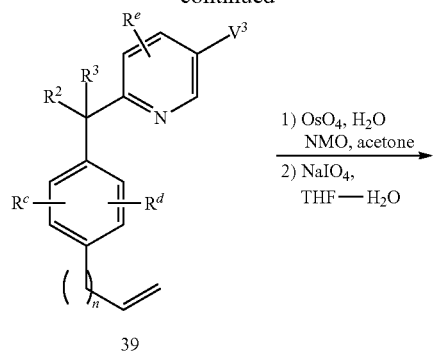

39

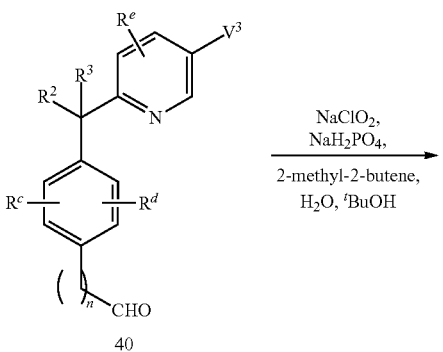

40

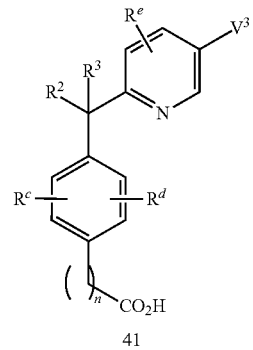

41

Reaction scheme L illustrates the preferred method of synthesis of compounds of structural formula 43. In the most general case, 41 is treated with an amine of type 42 to afford an amide of type 43. The amide bond coupling reaction illustrated in reaction scheme L is conducted in an appropriate inert solvent such as DMF, DCM or the like and may be performed with a variety of reagents suitable for amide coupling reactions such as HATU, EDC or PyBOP. Preferred conditions for the amide bond coupling reaction shown in reaction Scheme M are known to those skilled in organic synthesis. Such modifications may include, but are not limited to, the use of basic reagents such as triethylamine, DIPEA, or NMM, or the addition of an additive such as HOAt or HOBt. Alternatively, 42 may be treated with an activated ester or acid chloride derivative of 41, which also affords 43. The amide bond coupling shown in reaction Scheme L is usually conducted at a temperature between 0° C. and room temperature, occasionally at elevated temperatures, and the coupling reaction is typically conducted for periods of 1 to 24 hours.

Scheme L

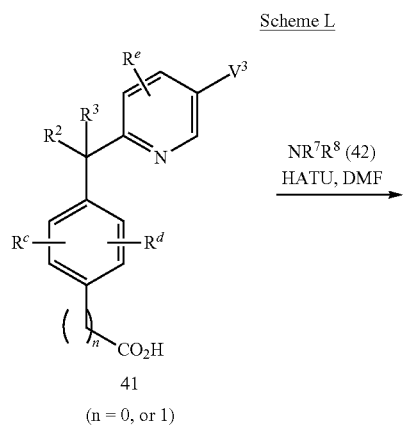

Scheme M

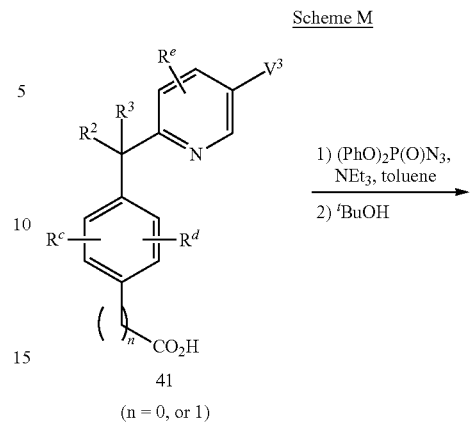

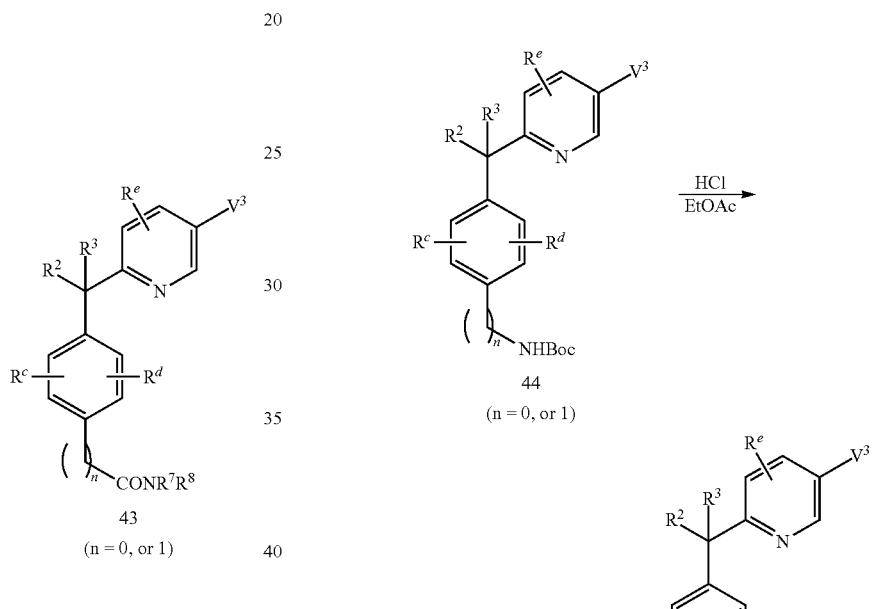

Reaction scheme M illustrates a preferred method for the synthesis of a compound of type 45. In this method, 41 is subjected to the Curtius reaction to afford a N-Boc protected amine derivative of structural formula 44. The reaction is performed by reacting 41 with diphenylphosphoryl azide in the presence of a tertiary amine such as triethylamine or DIPEA in a solvent such as toluene. The initial product is generally accepted to be the acyl azide, which is rearranged to the isocyanate in a thermal process analogous to the Wolff rearrangement of acyl carbenes. The rearrangement is conducted typically at the reflux temperature of the solvent, for instance 110° C., and the rearrangement is usually completed in periods of 1-5 hours. The intermediate isocyanate which forms is generally not isolated, but is in turn subjected to in situ reaction with a suitable alcohol such as tert-butyl alcohol to afford carbamate 44. The N-Boc group can be removed by a suitable deprotection method such as treatment with hydrogen chloride in EtOAc or TFA in DCM. The deprotection is conducted typically at temperatures between 0° C. and room temperature, and the reaction is usually complete in 0.5-3 hours. The product amine of structural formula 45 can be used as a coupling partner using a variety of methods known in organic synthesis to afford compounds of the present invention (I).

Reaction scheme N illustrates preferred methods for the syntheses of compounds of type 48. For example, 45 can participate in amide bond coupling reactions with a carboxylic acid of type 46 to afford an amide structural formula 48, using the reagents and conditions described for the generalized amide coupling protocol shown in reaction Scheme L. Alternatively, 45 may also be treated with an activated ester or acid chloride derivative of type 47, which also affords 48. Typical conditions for effecting such a transformation include treatment of 45 with acid chloride 47 in the presence of excess tertiary amine base such as triethylamine. It is customary to perform the reaction in an inert organic solvent such as DMF or DCM, at temperatures between 0° C. and the reflux temperature of the solvent, frequently at room temperature and for periods of 1-24 hours.

Scheme N

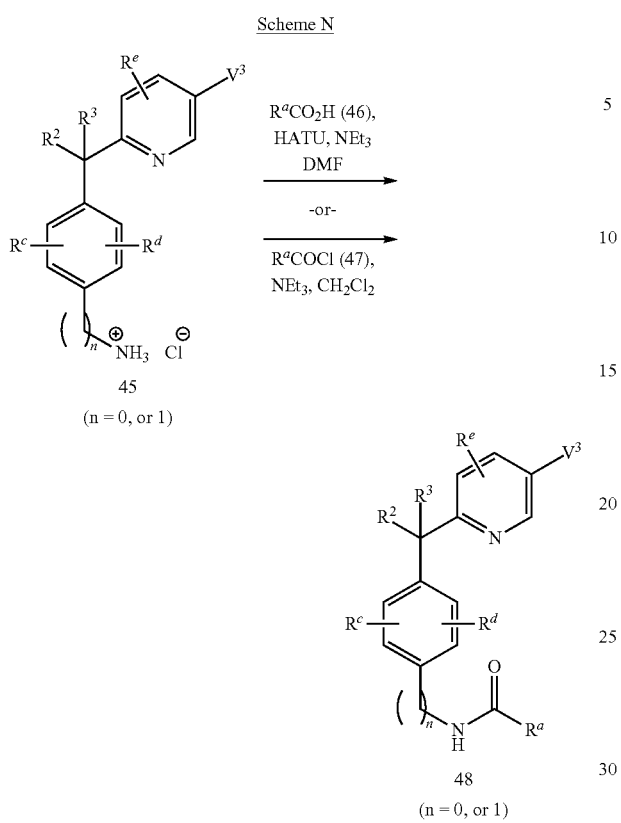

As shown in reaction scheme O, 45 can also be elaborated using the Fukuyama modification of the Mitsunobu reaction (Fukuyama, T.; Jow, C.-K.; Cheung, M. *Tetrahedron Lett.* 1995, 36, 6373-74). For example, 45 may be reacted with an arylsulfonyl chloride such as 2-nitrobenzenesulfonyl chloride, 4-nitrobenzenesulfonyl chloride or 2,4-dinitrobenzenesulfonyl chloride and a tertiary amine base such as 2,4,6-collidine or 2,6-lutidine in an inert organic solvent such as DCM. Alternatively, the reaction can also be performed under the classical Schotten-Baumann conditions as shown in scheme O, in which 45 and the arylsulfonyl chloride are allowed to react in aqueous alkaline solution. The product of this reaction is the sulfonamide of type 49, which can be further modified by reaction with an alcohol of type 50 in the presence of triphenylphosphine and an activating agent such as DEAD, DIAD, or the like. The reaction is performed in a suitable inert organic solvent such as benzene, toluene, THF or mixtures thereof, typically at room temperature, and the reaction is generally complete in 0.5-3 hours. The product of this reaction is the dialkylsulfonamide of type 51, which can be desulfonylated by treatment with either a nucleophilic amine like n-propylamine, in a solvent such as DCM, or with mercaptoacetic acid and triethylamine in DCM. In either case, the reaction is conducted typically at room temperature, for periods of 5 minutes to 1 hour. When a 2- or 4-nitrobenzenesulfonyl derivative is employed, the cleavage of the sulfonamide is accomplished with either the combination of thiophenol and potassium carbonate in a solvent like DMF, or with mercaptoacetic acid and lithium hydroxide in DMF. In either case, the reaction is conducted at room temperature, for periods of 1-3 hours. The secondary amine product of type 52 can be modified further using a variety of methods known in organic synthesis to provide other compounds of the present invention (I). For example, 52 may be subjected to a reductive amination reaction with an aldehyde or ketone of type 53 using the conditions described in the bottom of reaction Scheme O to afford compounds of type 54.

Scheme O

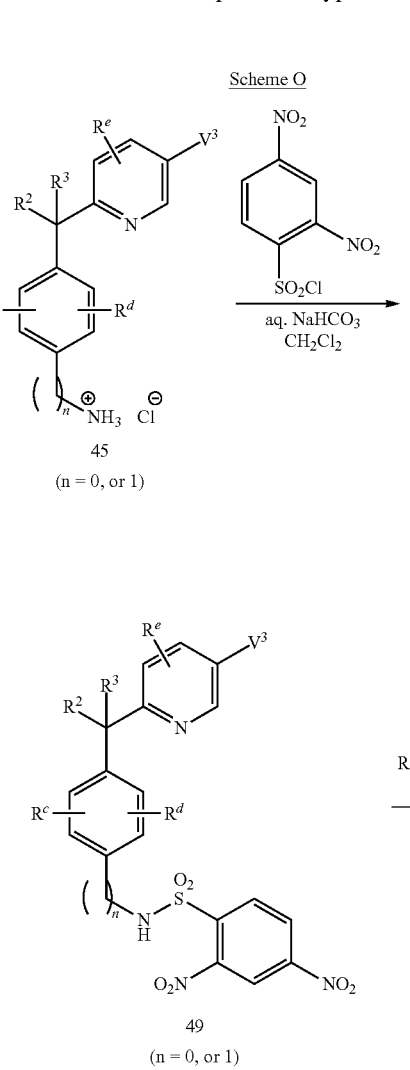

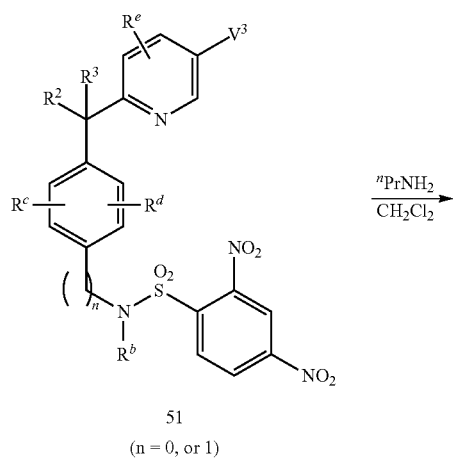

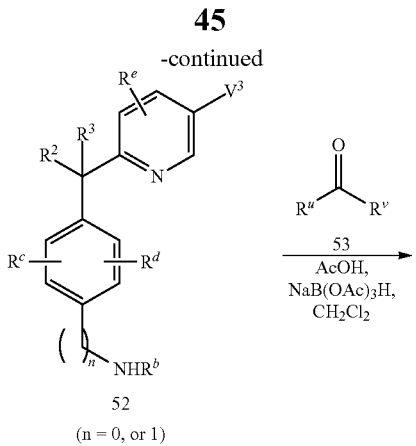

52
(n = 0, or 1)

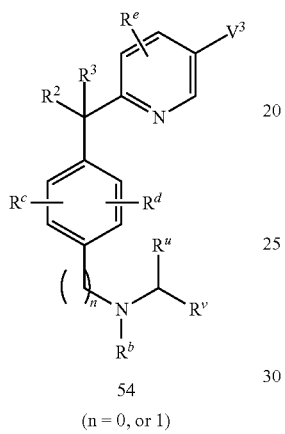

54
(n = 0, or 1)

In compound 54 when n=1,

—CHR$^u$R$^v$=a group within the scope of R$^a$ or a group that can be converted to R$^a$ as defined in formula II or when n=0, —CHR$^u$R$^v$=a group within the scope of R$^7$ or a group that can be converted to R$^7$ as defined in formula II Scheme P illustrates in the most generalized manner how compounds of type 55 can be elaborated to a variety of heterocyclic derivatives of structural formula 56 using known methods in organic synthesis. Specific examples of such transformations are shown in the Examples section.

Leading references for effecting such transformations include:

1) Joule, J. A; Mills, K. and Smith, G. F. Heterocyclic Chemistry, Chapman & Hall, 1995, 3rd Edn., and references cited therein;

2) Katritzky, A. R.; Rees, C. W. (Eds), Comprehensive Heterocyclic Chemistry: The Structure, Reactions, Synthesis, and Uses of Heterocyclic Compounds, Pergamon Press, Oxford, 1984, 8v, and references cited therein; and 3) Comprehensive Heterocyclic Chemistry II: Review of the Literature 1982-1995: The Structure, Reactions, Synthesis and Uses of Heterocyclic Compounds, Pergamon Press, New York, 2nd Edn., 1996, 11v, and references cited therein. (Comprehensive Heterocyclic Chemistry, vol. 4-6 Pergamon Press, New York, 1984, and references therein).

4) For compounds shown in Example 2, see: *Org. Lett.* 2001, 3, 3165-3168 and references cited therein.

5) For compounds shown in Example 3, see: *J. Med. Chem.* 1992, 35, 3691-3698 and references cited therein.

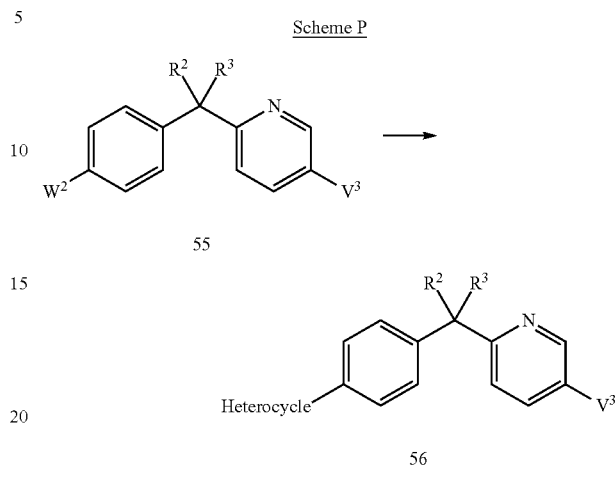

$W^2 = CO_2H, CO_2Me, CN$

Scheme Q illustrates the preferred method for the resolution of a racemic compound of structural formula 57 in which the asterisked carbon is a center of chirality. Generally, the latter or intermediates en route to their preparation, may be resolved to afford enantiomerically pure compounds such as 58 and 59 by employing chiral stationary phase liquid chromatography techniques or other suitable methods known in organic synthesis.

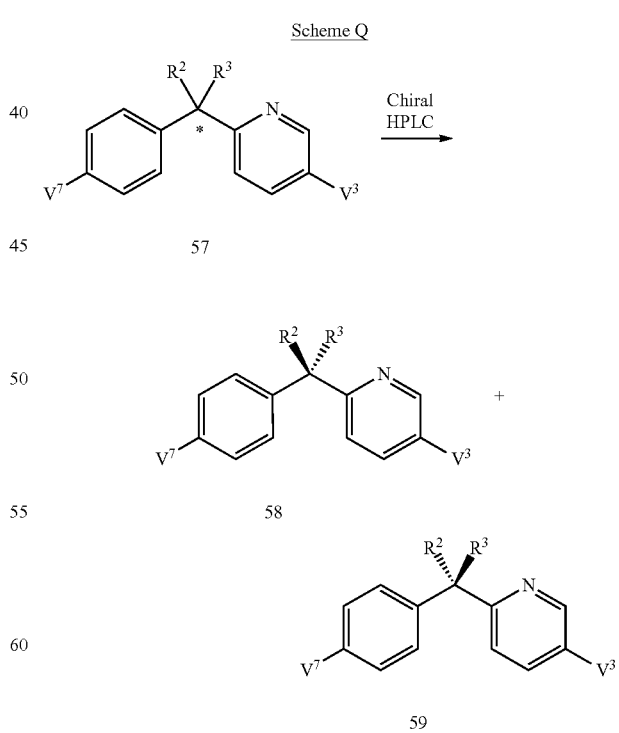

$V^7 = R^1$ as defined in formula I, or a group that can be converted to $R^1$

Intermediates used in the synthesis of compounds of this invention can be prepared using the following procedures.

Scheme i-1

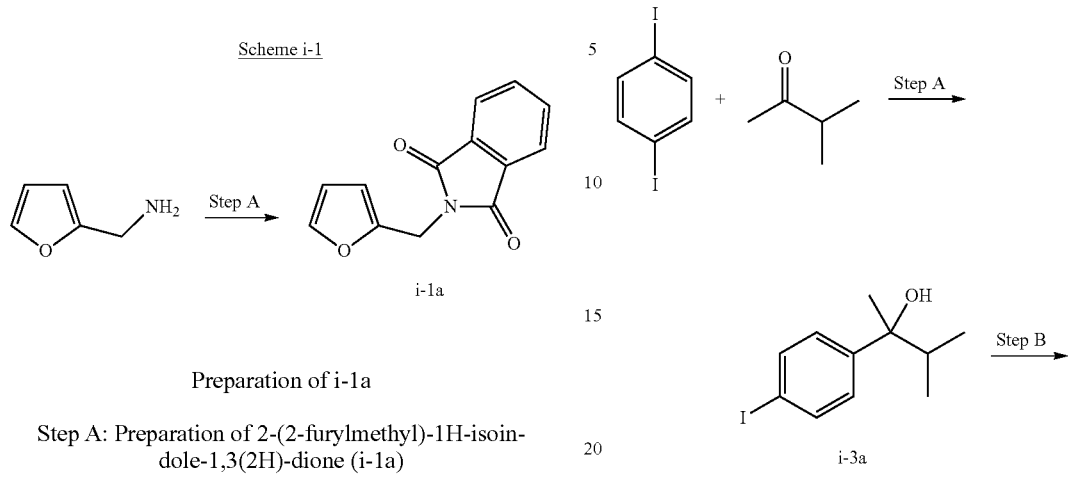

Preparation of i-1a

Step A: Preparation of 2-(2-furylmethyl)-1H-isoindole-1,3(2H)-dione (i-1a)

Furfurylamine (5.70 mL, 61.8 mmol) and phthalic anhydride (10.0 g, 90.9 mmol) were heated to 120° C. for approximately 45 min. The reaction mixture was cooled to it and then suspended in EtOH. The resulting suspension was filtered to afford the title compound i-1a. $^1$HNMR (500 MHz, CDCl$_3$): δ 7.88 (dd, 2H, J=3.2, 5.3 Hz), 7.73 (dd, 2H, J=3.0, 5.5 Hz), 6.38 (d, 1H, J=3.2 Hz), 6.32 (m, 1H), 4.88 (s, 2H).

Scheme i-2

Preparation of i-2a

Step A: Preparation of pyrimidin-2-ylmethyl methanesulfonate (i-2a)

Methanesulfonyl chloride (4.40 mL, 57.1 mmol) was added to a stirred solution of 2-hydroxymethylpyrimidine (6.28 g, 57.1 mmol) and triethylamine (9.50 mL, 68.5 mmol) in DCM (250 mL) at 0° C. After approximately 20 min, the reaction mixture was poured into water, the organic layer was separated and the aqueous phase was re-extracted twice with DCM. The combined organic extracts were washed with water, brine, dried (sodium sulfate), and concentrated in vacuo to afford the title compound i-2a. $^1$HNMR (500 MHz, CDCl$_3$): δ 8.81 (d, 2H, J=4.8 Hz), 7.32 (t, 1H, J=4.9 Hz), 5.46 (s, 2H), 3.24 (s, 3H).

Intermediate i-2b was prepared from 2-hydroxymethylthiazole following a procedure similar to that described for i-2a.

For i-2b: $^1$HNMR (500 MHz, CDCl$_3$): δ 7.88 (d, 1H, J=3.2 Hz), 7.50 (d, 1H, J=3.2 Hz), 5.55 (s, 2H), 3.11 (s, 3H).

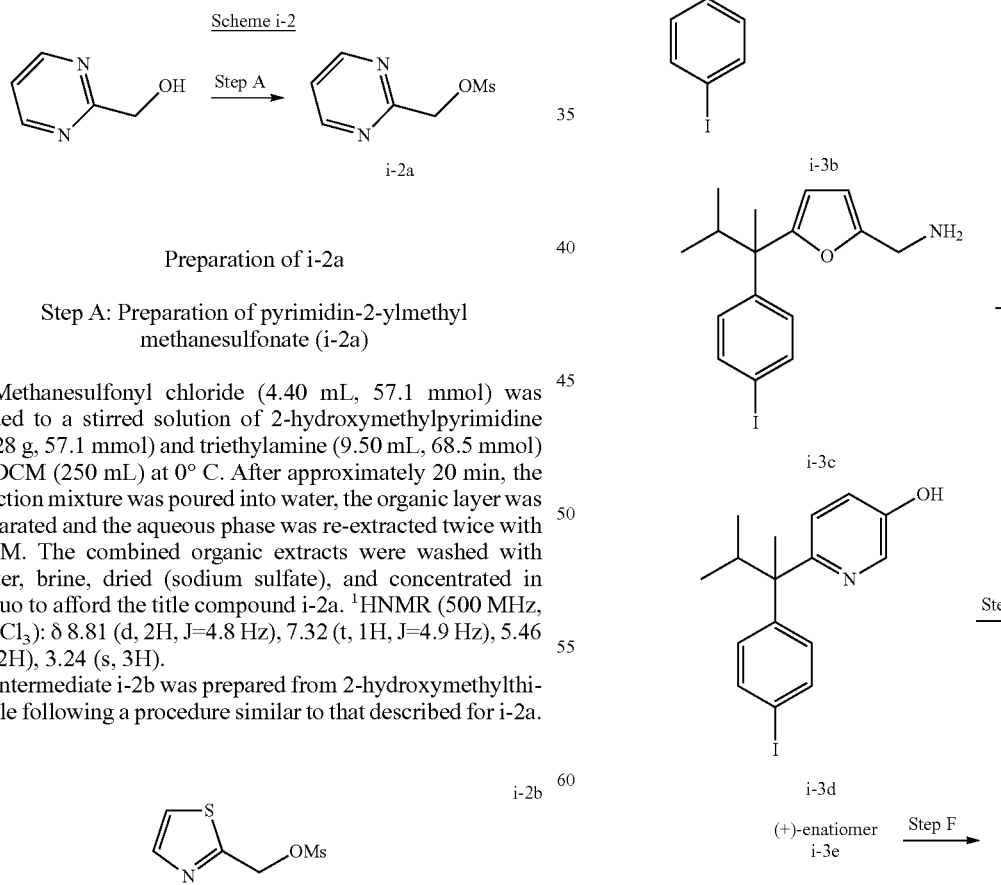

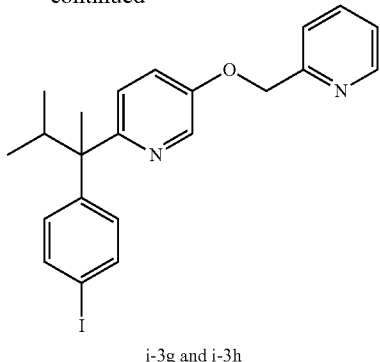

i-3g and i-3h

Preparation of i-3g and i-3h

Step A: Preparation of 2-(4-iodophenyl)-3-methylbutan-2-ol (i-3a)

n-Butyllithium (37.0 mL of a 2.5 M solution in hexanes, 92.8 mmol) was added to a stirred solution of 1,4-diiodobenzene (30.0 g, 90.9 mmol) in THF (200 mL) at −78° C. After approximately 20 min, 3-methyl-2-butanone (10.2 mL, 95.5 mmol) was added, and the resulting mixture was allowed to stir at −78° C. for about 1 h. The reaction mixture was poured into aqueous 1N HCl and extracted twice with diethyl ether. The combined organic extracts were washed water, brine, dried (magnesium sulfate) and concentrated in vacuo to afford the title compound i-3a. m/z (ES) 273 (M-OH)$^+$.
$^1$HNMR (500 MHz, CDCl$_3$): δ 7.67 (d, 2H, J=8.5 Hz), 7.20 (d, 2H, J=8.7 Hz), 2.00 (m, 1H, J=6.7 Hz), 1.52 (s, 3H), 0.92 (d, 3H, J=6.7 Hz), 0.81 (d, 3H, J=6.9 Hz).

Step B: Preparation of 2-({5-[1-(4-iodophenyl)-1,2-dimethylpronyl]-2-furyl}methyl)-1H-isoindole-1,3 (2H)-dione (i-3b)

Tetrafluoroboric acid (13.0 mL of a 54% wt solution in diethyl ether, 96.1 mmol) was added to a stirred solution of i-3a (23.2 g, 80.1 mmol) in DCM (200 mL) at −78° C. After approximately 5 min, i-1a (19.1 g, 84.1 mmol) was added in one portion and the resulting suspension stirred at −78° C. for about 15 min. After warming to rt over approximately 2 h, the reaction mixture was quenched cautiously with saturated aqueous sodium bicarbonate, and the organic layer was separated. The aqueous layer was extracted twice with DCM and the combined organic extracts were washed with brine, dried (sodium sulfate) and concentrated in vacuo. The crude residue was purified by flash chromatography on silica gel (gradient elution; 5%-20% EtOAc/hexanes as eluent) to afford the title compound i-3b. m/z (ES) 500 (MH)$^+$.
$^1$HNMR (500 MHz, CDCl$_3$): δ 7.88 (dd, 2H, J=3.0, 5.5 Hz), 7.77 (dd, 2H, J=3.0, 5.5 Hz), 7.47 (dd, 2H, J=2.5, 9.0 Hz), 7.06 (dd, 2H, J=2.3, 8.8 Hz), 6.24 (d, 1H, J=3.0 Hz), 6.01 (d, 1H, J=3.0 Hz), 4.85 (m, 2H), 2.58 (m, 1H, J=7.0 Hz), 1.50 (s, 3H), 0.82 (d, 3H, J=6.5 Hz), 0.68 (d, 3H, J=6.5 Hz).

Step C: Preparation of 1-{5-[1-(4-iodophenyl)-1,2-dimethylpropyl]-2-furyl}methanamine (i-3c)

Hydrazine monohydrate (27.0 mL, 566 mmol) was added to a stirred solution of i-3b (18.8 g, 37.8 mmol) in EtOH (200 mL). The reaction mixture was heated at reflux for approximately 1 h, then cooled to room temperature and filtered. The residue was washed four times with EtOAc, and the collected filtrate was partially concentrated in vacuo. The resultant solution was washed with water, brine, dried (sodium sulfate) and concentrated in vacuo to afford the title compound i-3c.
$^1$HNMR (500 MHz, CDCl$_3$): δ 7.62 (d, 2H, J=8.5 Hz), 7.09 (d, 2H, J=8.7 Hz), 6.06 (m, 2H), 3.81 (s, 2H), 2.58 (m, 1H, J=6.8 Hz), 1.55 (s, 3H), 0.92 (d, 3H, J=6.8 Hz), 0.74 (d, 3H, J=6.9 Hz).

Step D: Preparation of 6-[1-(4-iodophenyl)-1,2-dimethylpropyl]pyridin-3-ol (i-3d)

Bromine (32.0 mL of a 1.0 M solution in MeOH) was added dropwise via a pressure equalizing addition funnel to a stirred solution of i-3c (13.9 g, 37.8 mmol) in MeOH (15.0 mL) and water (35.0 mL) at 0° C. After approximately 1 h, the reaction mixture was quenched with saturated aqueous sodium bicarbonate and extracted twice with EtOAc. The combined organic extracts were washed with brine, dried (sodium sulfate), and concentrated in vacuo. The crude residue was purified by flash chromatography on silica gel (gradient elution; 0%-50% EtOAc/hexanes as eluent) to afford the title compound i-3d. m/z (ES) 368 (MH)$^+$.
$^1$HNMR (500 MHz, CDCl$_3$): δ 8.11 (m, 1H), 7.55 (d, 2H, J=8.2 Hz), 7.08 (m, 3H), 7.01 (m, 1H), 2.94 (m, 1H), 1.62 (s, 3H), 0.83 (d, 3H, J=6.7 Hz), 0.79 (d, 3H, J=6.8 Hz).

Step E: Preparation of (i-3e) and (i-3f)

Enantiomers i-3e and i-3f were separated using preparative normal phase chiral HPLC. A solution of i-3d in MeOH was injected onto a CHIRALCEL® OD-H (available from Chiral Technologies, Inc., Exton, Pa.) semi-preparative (250×21 mm) HPLC column (eluting with 15% MeOH/CO$_2$ with a column temperature of 40° C. at 50 mL/min with UV detection at 220 nm). The enantiomers were separated with the faster eluting enantiomer i-3e having a retention time of 5.83 min and the slower eluting enantiomer i-3f having a retention time of 6.40 min. The separated fractions were concentrated to provide the enantiomers i-3e and i-3f.

Step F: Preparation of 2-[1-(4-iodophenyl)-1,2-dimethylpropyl]-5-(pyridin-2-ylmethoxy)pyridine (i-3g)

Cesium carbonate (0.520 g, 1.60 mmol), potassium iodide (126 mg, 0.760 mmol), and 2-picolyl chloride hydrochloride (138 mg, 0.840 mmol) were added to a stirred solution of i-3e (280 mg, 0.760 mmol) in DMF (5.00 mL) at rt. After approximately 18 h, the reaction mixture was quenched by the addition of saturated aqueous ammonium chloride, the resulting mixture was poured into water and extracted three times with EtOAc. The combined organic extracts were washed with saturated aqueous sodium bicarbonate, water, brine, dried (magnesium sulfate) and concentrated in vacuo to afford the title compound i-3g. m/z (ES) 459 (MH)$^+$. $^1$HNMR (500 MHz, CDCl$_3$): δ 8.61 (d, 1H, J=4.5 Hz), 8.38 (d, 1H, J=3.0 Hz), 7.74 (t, 1H, J=7.7 Hz), 7.57 (d, 2H, J=8.2 Hz), 7.52 (d, 1H, J=7.8 Hz), 7.27 (m, 1H), 7.17 (dd, 1H, J=2.8, 8.8 Hz), 7.11 (m, 3H), 5.22 (s, 2H), 3.00 (m, 1H, J=6.7 Hz), 1.63 (s, 3H), 0.83 (d, 3H, J=6.7 Hz), 0.77 (d, 3H, J=6.9 Hz). In a similar manner, intermediate i-3f can be converted to i-3h.

Following procedures similar to that described for preparing intermediate i-3g employing chiral intermediate i-3e, the following additional intermediates i-3i and i-3j were

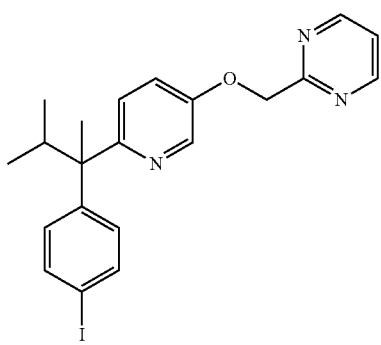

i-3i

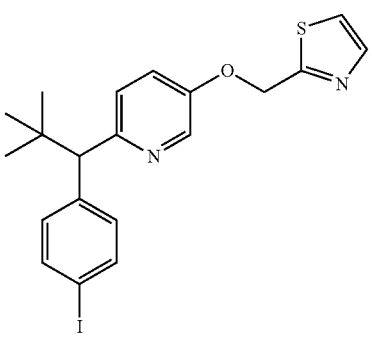

i-3k

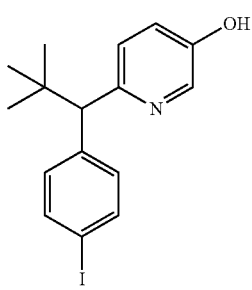

i-3j

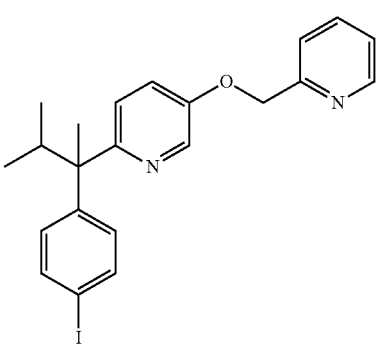

i-3l

For i-3i: m/z (ES) 460 (MH)⁺. ¹HNMR (500 MHz, CDCl₃): δ 8.81 (d, 2H, J=4.8 Hz), 8.39 (d, 1H, J=3.0 Hz), 7.57 (d, 2H, J=8.2 Hz), 7.29 (m, 1H), 7.22 (dd, 1H, J=2.6, 8.8 Hz), 7.12 (m, 3H), 5.34 (s, 2H), 3.00 (m, 1H, J=6.7 Hz), 1.63 (s, 3H), 0.83 (d, 3H, J=6.6 Hz), 0.77 (d, 3H, J=6.9 Hz).

For i-3j: m/z (ES) 465 (MH)⁺. ¹HNMR (500 MHz, CDCl₃): δ 8.38 (d, 1H, J=2.9 Hz), 7.82 (d, 1H, J=2.2 Hz), 7.57 (d, 2H, J=8.5 Hz), 7.41 (d, 1H, J=2.4 Hz), 7.22 (dd, 1H, J=3.0, 8.9 Hz), 7.13 (d, 1H, J=8.7 Hz), 7.11 (d, 2H, J=8.7 Hz), 5.40 (s, 2H), 3.00 (m, 1H, J=6.8 Hz), 1.63 (s, 3H), 0.82 (d, 3H, J=6.6 Hz), 0.77 (d, 3H, J=6.9 Hz)

Following procedures similar to that described above for the preparation of intermediate i-3d, but substituting pivaldehyde for 3-methyl-2-butanone, the following intermediate can be prepared.

i-3m

i-3n

Following procedures similar to that described above for preparing intermediates i-3g, i-3i, i-3j, and the following additional intermediates can be prepared from intermediate i-3n in chiral or racemic form.

Scheme i-4

 Step A → i-3g

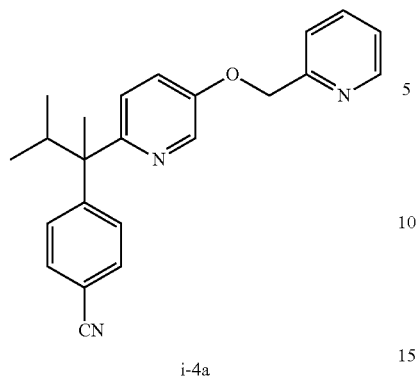

i-4a

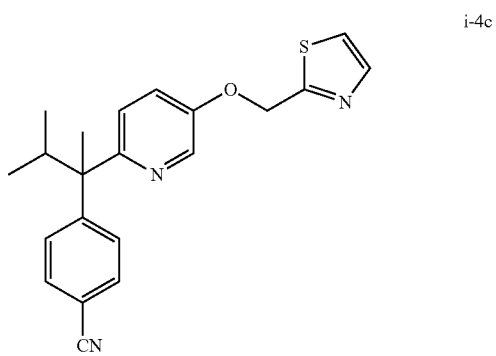

i-4c

Preparation of i-4a

Step A: Preparation of 4-{1,2-dimethyl-1-[5-(pyridin-2-ylmethoxy)pyridin-2-yl]propyl}benzonitrile (i-4a)

Tetrakis(triphenylphosphine) palladium(0) (49.0 mg, 0.0420 mmol) was added to a stirred solution of i-3g (385 mg, 0.840 mmol), potassium cyanide (109 mg, 1.68 mmol) and copper(I) iodide (16.0 mg, 0.0840 mmol) in MeCN (6.00 mL) at rt. The resulting mixture was heated to 80° C. for approximately 25 min. After cooling to rt, the reaction mixture was diluted with water, and the resulting biphasic mixture was filtered through a short column of Celite®, eluting with EtOAc. The organic phase was separated from the filtrate, washed with brine, dried (sodium sulfate) and concentrated in vacuo. The crude residue was purified by flash chromatography on silica gel (gradient elution; 0%-50% EtOAc/hexanes as eluent) to afford the title compound i-4a. m/z (ES) 358 (MH)$^+$. $^1$HNMR (500 MHz, CDCl$_3$): δ 8.63 (d, 1H, J=4.4 Hz), 8.40 (d, 1H, J=3.0 Hz), 7.76 (dt, 1H, J=1.7, 7.7 Hz), 7.53 (m, 5H), 7.28 (m, 1H), 7.21 (dd, 1H, J=2.9, 8.7 Hz), 7.15 (d, 1H, J=8.7 Hz), 5.24 (s, 2H), 3.06 (m, 1H, J=6.7 Hz), 1.69 (s, 3H), 0.86 (d, 3H, J=6.9 Hz), 0.76 (d, 3H, J=6.7 Hz).

Following procedures similar to that described for intermediate i-4a, the following additional intermediates i-4b and i-4c can be prepared from i-3i and i-3j, respectively.

For i-4b: m/z (ES) 359 (MH)$^+$. $^1$HNMR (500 MHz, CDCl$_3$): δ 8.81 (d, 2H, J=5.0 Hz), 8 8.41 (d, 1H, J=3.0 Hz), 7.55 (d, 2H, J=8.5 Hz), 7.48 (d, 2H, J=8.7 Hz), 7.30 (m, 1H), 7.25 (dd, 1H, J=2.7, 8.7 Hz), 7.14 (d, 1H, J=8.9 Hz), 5.34 (s, 2H), 3.05 (m, 1H, J=6.7 Hz), 1.68 (s, 3H), 0.85 (d, 3H, J=6.6 Hz), 0.75 (d, 3H, J=6.9 Hz).

Following procedures similar to that described for intermediate i-4a, the following additional intermediates i-4d, i-4e, and i-4f can be prepared from i-3k, i-3l and i-3m, respectively.

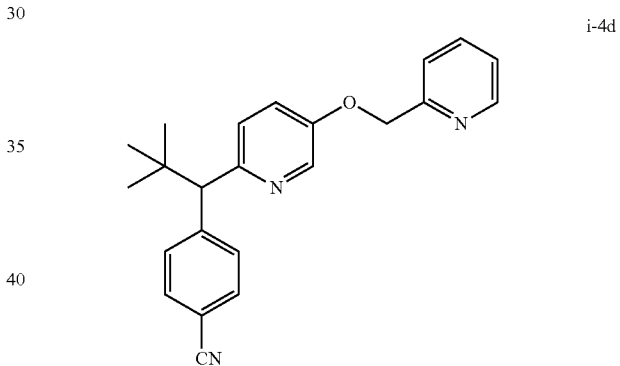

i-4d

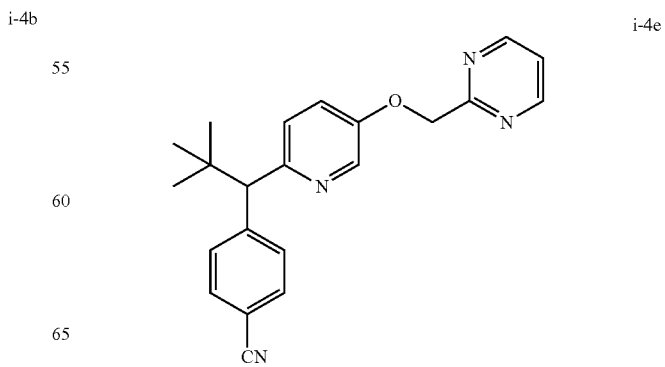

i-4e

-continued

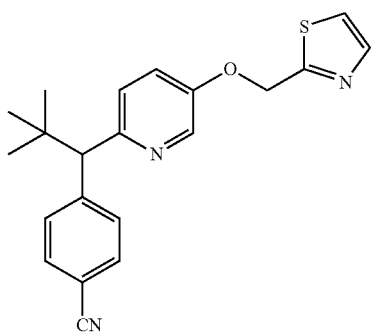
i-4f

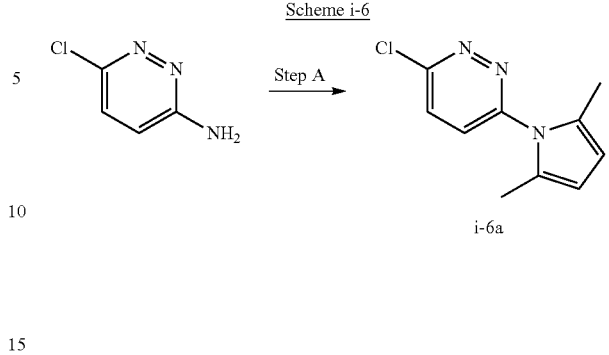

Preparation of 3-chloro-6-(2,5-dimethyl-1H-pyrrol-1-yl)pyridazine (i-6a)

A mixture of p-TSA (117 mg, 0.618 mmol), 2,5-hexanedione (4.36 mL, 37.1 mmol) and 3-amino-6-chloropyridazine (4.00 g, 30.9 mmol) in toluene (150 mL) was heated at 140° C. for 5 h in a round bottom flask equipped with a condenser and Dean-Stark apparatus. The reaction mixture was cooled to rt and charcoal was added. The mixture was filtered through CELITE and concentrated in vacuo to afford the title compound i-6a. m/z (ES) 208 (MH)$^+$.

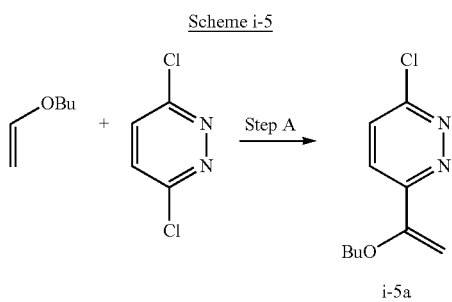

Preparation of i-5a

Step A: Preparation of 3-(1-butoxyvinyl)-6-chloropyridazine (i-5a)

THF (24.0 mL) was added rapidly dropwise to tert-butyllithium (150 mL of a 1.7 M solution in pentane) at −78° C. After 15 min, n-butyl vinyl ether (14.0 mL, 109.4 mmol) was added, and the resulting mixture was warmed to −30° C., at which point modest gas evolution was observed. As gas evolution ceased, a second portion of n-butyl vinyl ether (14.0 mL, 109.4 mmol) was added, maintaining the reaction temperature at −30° C. After gas evolution had ceased, the reaction mixture was cooled to −78° C., and a solution of zinc chloride (29.8 g, 219 mmol) in THF (250 mL) was added rapidly dropwise. After 15 min, the reaction was warmed to −10° C. and transferred via cannula to a stirred solution of 3,6-dichloropyridazine (32.6 g, 219 mmol) and [1,1'-bis(diphenylphosphino)ferrocene]dichloropalladium(II) (16.0 g, 21.9 mmol) in THF (200 mL) at 0° C. After 1 h at 0° C., the reaction mixture was diluted with EtOAc and filtered through a short column of CELITE®, eluting with EtOAc. The filtrate was washed with water and brine, dried (sodium sulfate), and concentrated in vacuo. The crude residue was purified by flash chromatography on silica gel (gradient elution; 0%-15% EtOAc/hexanes as eluent) to afford the title compound i-5a. $^1$HNMR (500 MHz, CDCl$_3$): δ 7.80 (d, 1H, J=8.9 Hz), 7.52 (d, 1H, J=8.9 Hz), 5.76 (d, 1H, J=2.5 Hz), 4.55 (d, 1H, J=2.5 Hz), 3.97 (t, 2H, J=6.4 Hz), 1.83 (m, 2H), 1.57 (m, 2H), 1.02 (t, 3H, J=7.5 Hz).

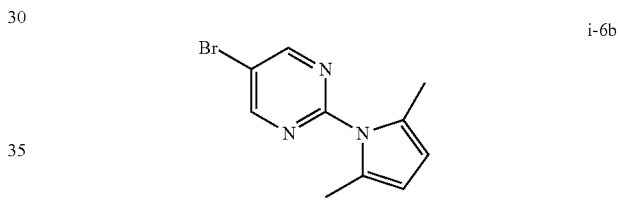

Preparation of 5-bromo-2-(2,5-dimethyl-1H-pyrrol-1-yl)pyrimidine (i-6b)

Compound i-6b was prepared following the procedures described above. m/z (ES) 252 (MH)$^+$.

In the Tables in the following Examples, compounds having mass spectral data were synthetically prepared.

EXAMPLE 1

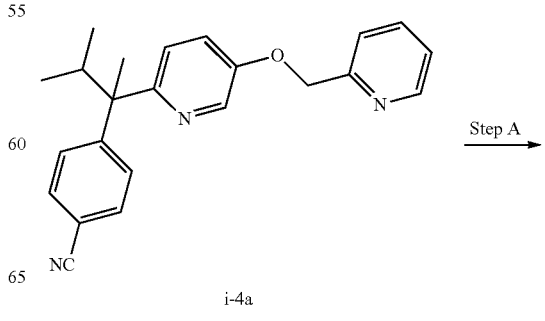
i-4a

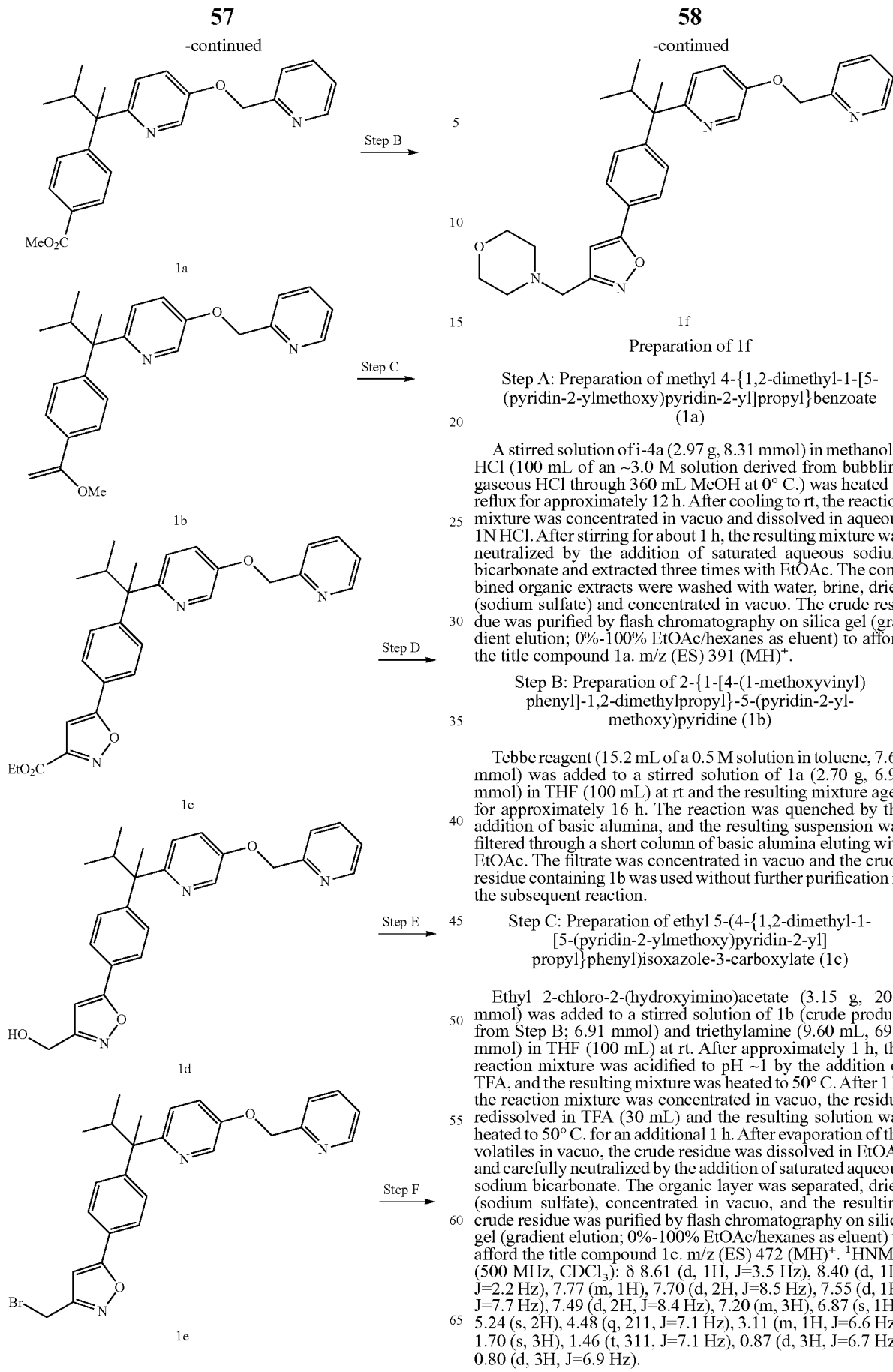

Preparation of 1f

Step A: Preparation of methyl 4-{1,2-dimethyl-1-[5-(pyridin-2-ylmethoxy)pyridin-2-yl]propyl}benzoate (1a)

A stirred solution of i-4a (2.97 g, 8.31 mmol) in methanolic HCl (100 mL of an ~3.0 M solution derived from bubbling gaseous HCl through 360 mL MeOH at 0° C.) was heated at reflux for approximately 12 h. After cooling to rt, the reaction mixture was concentrated in vacuo and dissolved in aqueous 1N HCl. After stirring for about 1 h, the resulting mixture was neutralized by the addition of saturated aqueous sodium bicarbonate and extracted three times with EtOAc. The combined organic extracts were washed with water, brine, dried (sodium sulfate) and concentrated in vacuo. The crude residue was purified by flash chromatography on silica gel (gradient elution; 0%-100% EtOAc/hexanes as eluent) to afford the title compound 1a. m/z (ES) 391 (MH)+.

Step B: Preparation of 2-{1-[4-(1-methoxyvinyl)phenyl]-1,2-dimethylpropyl}-5-(pyridin-2-ylmethoxy)pyridine (1b)

Tebbe reagent (15.2 mL of a 0.5 M solution in toluene, 7.60 mmol) was added to a stirred solution of 1a (2.70 g, 6.91 mmol) in THF (100 mL) at rt and the resulting mixture aged for approximately 16 h. The reaction was quenched by the addition of basic alumina, and the resulting suspension was filtered through a short column of basic alumina eluting with EtOAc. The filtrate was concentrated in vacuo and the crude residue containing 1b was used without further purification in the subsequent reaction.

Step C: Preparation of ethyl 5-(4-{1,2-dimethyl-1-[5-(pyridin-2-ylmethoxy)pyridin-2-yl]propyl}phenyl)isoxazole-3-carboxylate (1c)

Ethyl 2-chloro-2-(hydroxyimino)acetate (3.15 g, 20.7 mmol) was added to a stirred solution of 1b (crude product from Step B; 6.91 mmol) and triethylamine (9.60 mL, 69.1 mmol) in THF (100 mL) at rt. After approximately 1 h, the reaction mixture was acidified to pH ~1 by the addition of TFA, and the resulting mixture was heated to 50° C. After 1 h, the reaction mixture was concentrated in vacuo, the residue redissolved in TFA (30 mL) and the resulting solution was heated to 50° C. for an additional 1 h. After evaporation of the volatiles in vacuo, the crude residue was dissolved in EtOAc and carefully neutralized by the addition of saturated aqueous sodium bicarbonate. The organic layer was separated, dried (sodium sulfate), concentrated in vacuo, and the resulting crude residue was purified by flash chromatography on silica gel (gradient elution; 0%-100% EtOAc/hexanes as eluent) to afford the title compound 1c. m/z (ES) 472 (MH)+. $^1$HNMR (500 MHz, CDCl$_3$): δ 8.61 (d, 1H, J=3.5 Hz), 8.40 (d, 1H, J=2.2 Hz), 7.77 (m, 1H), 7.70 (d, 2H, J=8.5 Hz), 7.55 (d, 1H, J=7.7 Hz), 7.49 (d, 2H, J=8.4 Hz), 7.20 (m, 3H), 6.87 (s, 1H), 5.24 (s, 2H), 4.48 (q, 2H, J=7.1 Hz), 3.11 (m, 1H, J=6.6 Hz), 1.70 (s, 3H), 1.46 (t, 3H, J=7.1 Hz), 0.87 (d, 3H, J=6.7 Hz), 0.80 (d, 3H, J=6.9 Hz).

Step D: Preparation of [5-(4-{1,2-dimethyl-1-[5-(pyridin-2-ylmethoxy)pyridin-2-yl]propyl}phenyl)isoxazol-3-yl]methanol (1d)

Lithium aluminum hydride (7.80 mL of a 1.0 M solution in THF, 7.80 mmol) was added to a stirred solution of 1c (2.46 g, 5.22 mmol) in diethyl ether (10.0 mL) at 0° C. After approximately 10 min, 1N NaOH was added to quench the reaction followed by dilution with EtOAc. The resulting mixture was dried (magnesium sulfate), filtered and concentrated in vacuo. The crude residue was purified by flash chromatography on silica gel (gradient elution; 0%-100% EtOAc/hexanes as eluent) to afford the title compound 1d. m/z (ES) 430 (MH)+. $^1$HNMR (500 MHz, CDCl$_3$): δ 8.61 (d, 1H, J=4.5 Hz), 8.40 (d, 1H, J=2.5 Hz), 7.75 (m, 1H), 7.67 (d, 211, J=8.5 Hz), 7.53 (d, 1H, J=8.0 Hz), 7.47 (d, 2H, J=8.5 Hz), 7.29 (m, 1H), 7.19 (m, 2H), 6.53 (s, 1H), 5.23 (s, 2H), 4.81 (s, 2H), 3.08 (m, 1H), 1.68 (s, 3H), 0.87 (d, 3H, J=6.6 Hz), 0.80 (d, 3H, J=6.9 Hz).

Step E: Preparation of 2-(1-{4-[3-(bromomethyl)isoxazol-5-yl]phenyl}-1,2-dimethylpropyl)-5-(pyridin-2-ylmethoxy)pyridine (1e)

Triphenylphosphine (1.34 g, 5.21 mmol) was added to a stirred solution of 1d (1.49 g, 3.47 mmol) and carbon tetrabromide (1.73 g, 5.21 mmol) in THF (100 mL) at rt. After approximately 1.5 h, the reaction mixture was poured into saturated aqueous sodium bicarbonate and extracted three times with EtOAc. The combined organic extracts were dried (magnesium sulfate), concentrated in vacuo, and the crude residue was purified by flash chromatography on silica gel (gradient elution; 0%-70% EtOAc/hexanes as eluent) to afford the title compound 1e. m/z (ES) 494 (MH)+.

Step F: Preparation of 4-{[5-(4-{1,2-dimethyl-1-[5-(pyridin-2-ylmethoxy)pyridin-2-yl]propyl}phenyl)isoxazol-3-yl]methyl}morpholine (1f)

Morpholine (17.5 μL, 0.200 mmol) was added to a stirred solution of 1e (49.0 mg, 0.100 mmol) and cesium carbonate (130 mg, 0.400 mmol) in DMF (1.00 mL) at rt. The resulting mixture was heated to 50° C. for approximately 1 h, cooled to rt, and then filtered through a short column of CELITE® eluting with EtOAc. The filtrate was concentrated in vacuo and the crude residue was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 1f. m/z (ES) 499 (MH)+.

Following procedures similar to that described above for compounds 1c, 1d and 1f, the following additional compounds can be prepared (Table 1):

TABLE 1

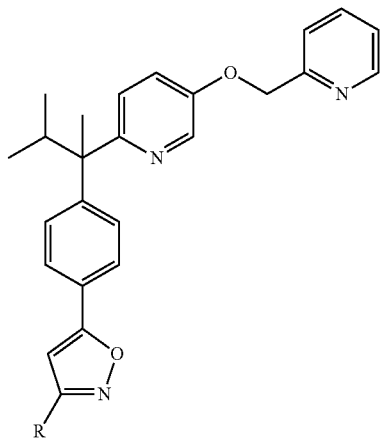

1A

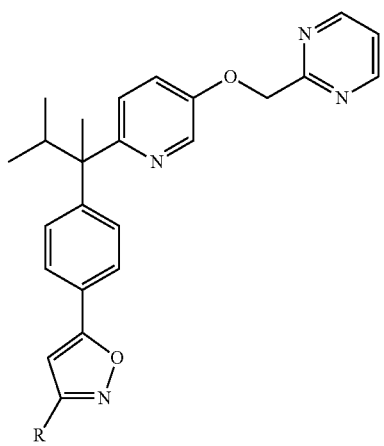

1B

TABLE 1-continued
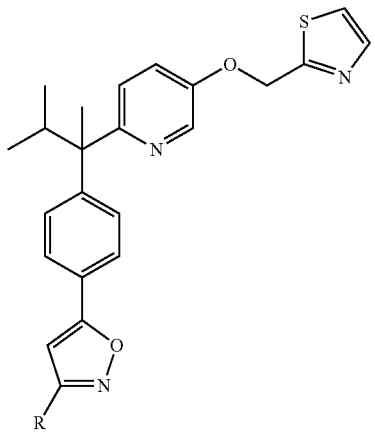
1C
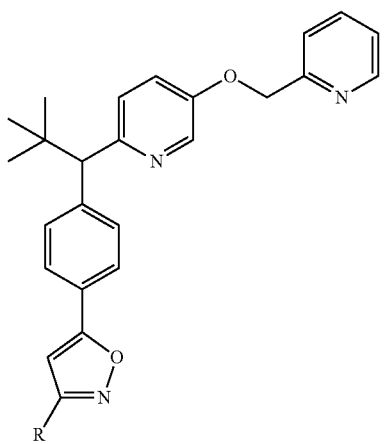
1D
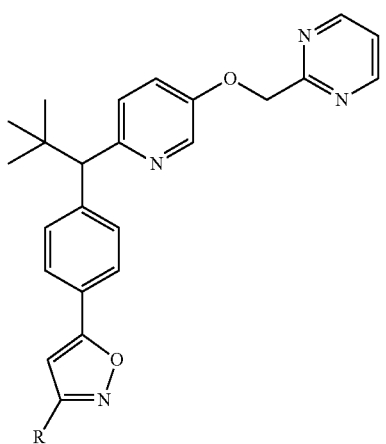
1E

TABLE 1-continued
1F
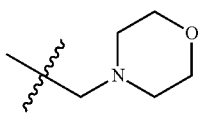 [SMILES: *CN1CCOCC1]
| Ex. #1A | Ex. #1B | Ex. #1C | Ex. #1D | Ex. #1E | Ex. #1F | R |
|---------|---------|---------|---------|---------|---------|---|
| — | a | a | a | a | a | CO$_2$Me |
| — | b | b | b | b | b | —CH$_2$OH |
| — | c | c | c | c | c | 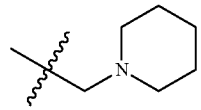 [SMILES: *CN1CCCCC1] |
| d | d | d | d | d | d | 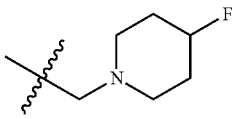 [SMILES: *CN1CCC(F)CC1] |
| e | e | e | e | e | e | 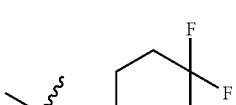 |
| f | f | f | f | f | f | 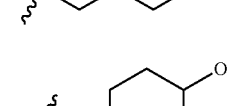 |
| g | g | g | g | g | g | 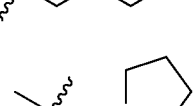 |
| h | h | h | h | h | h | 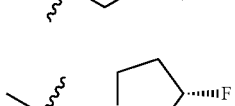 |
| i | i | i | i | i | i | 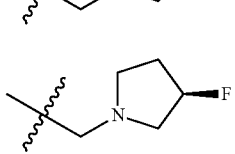 |
| j | j | j | j | j | j |  |

TABLE 1-continued

| | | | | | | |
|---|---|---|---|---|---|---|
| k | k | k | k | k | k | pyrrolidine-3-ol (R) |
| l | l | l | l | l | l | pyrrolidine-3-ol (S) |
| m | m | m | m | m | m | azetidine-3-ol |
| n | n | n | n | n | n | 3-fluoroazetidine |
| o | o | o | o | o | o | 3,3-difluoroazetidine |

Table 1. Parent Ion m/z (MH)+ data for compounds 1Ad: 497; 1Ae: 515; 1Af: 533; 1Ag: 513; 1Ah: 483; 1Ai: 501; 1Aj: 501; 1Ak: 499; 1Al: 499; 1Am: 485; 1An: 487; 1Ao: 505; 1Ca: 464; 1Cb: 436; 1Cc: 506; 1Ci: 508; 1Cm: 491; 1Cn: 494; 1Co: 512.

EXAMPLE 2

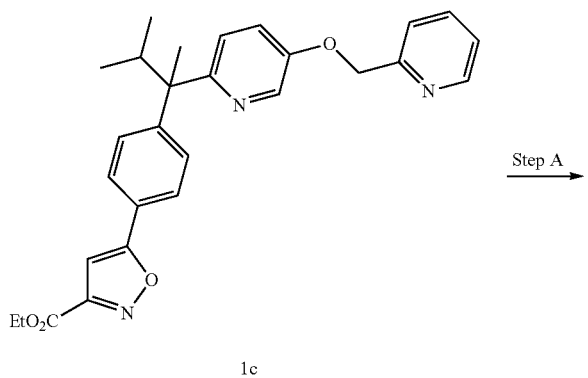

1c

Preparation of 2a

Step A: Preparation of 2-[5-(4-{1,2-dimethyl-1-[5-(pyridin-2-ylmethoxy)pyridin-2-yl]propyl}phenyl)isoxazol-3-yl]propan-2-ol (2a)

Methyl magnesium bromide (334 μL of a 1.4M solution in toluene:THF (75:25), 0.468 mmol) was added to a stirred solution of 1c (55.0 mg, 0.117 mmol) in THF (1.00 mL) at 0° C. After approximately 1 h, the reaction was quenched with water, and the resulting mixture was purified directly by flash chromatography on silica gel (gradient elution; 0%-100% EtOAc/hexanes as eluent) to afford the title compound 2a. m/z (ES) 457 (MH)+. $^1$HNMR (500 MHz, CDCl$_3$): δ 8.61 (d, 1H, J=4.6 Hz), 7.67 (m, 1H), 7.67 (d, 2H, J=8.5 Hz), 7.58 (d, 1H, J=8.0 Hz), 7.36 (d, 2H, J=8.5 Hz), 7.25 (m, 1H), 7.19 (d, 2H, J=8.3 Hz), 6.92 (d, 2H, J=8.9 Hz), 5.22 (s, 2H), 2.72 (m, 1H), 1.68 (s, 6H), 1.63 (s, 3H), 0.89 (d, 3H, J=6.7 Hz), 0.86 (d, 3H, J=6.7 Hz).

Following procedures similar to that described above for compound 2a, the following additional compounds 2b and 2c can be prepared:

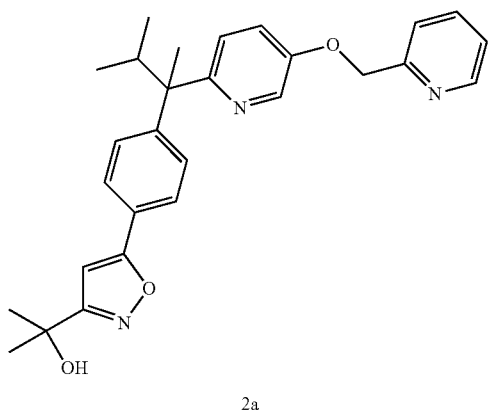

2a

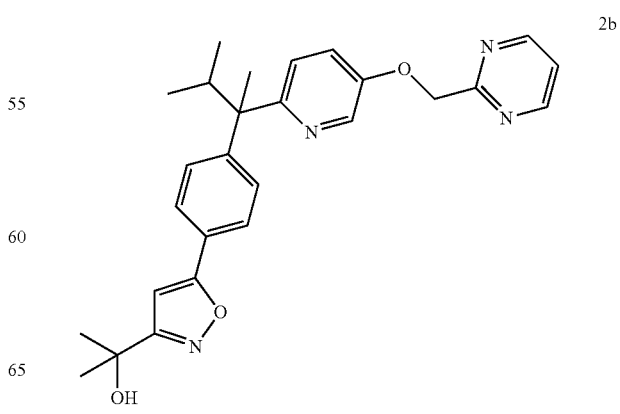

2b

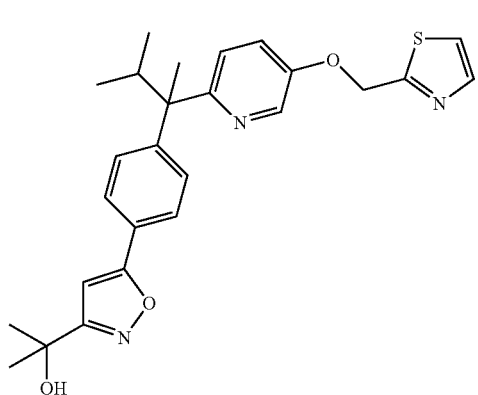
2c
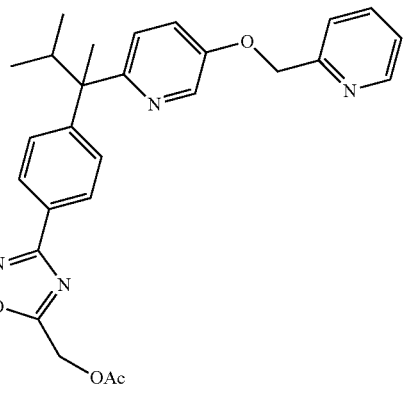
3c
EXAMPLE 2
Parent Ion m/z (MH)+ data for compounds 2c: 464.
EXAMPLE 3
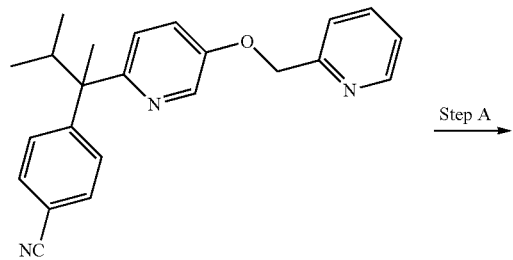
i-4a
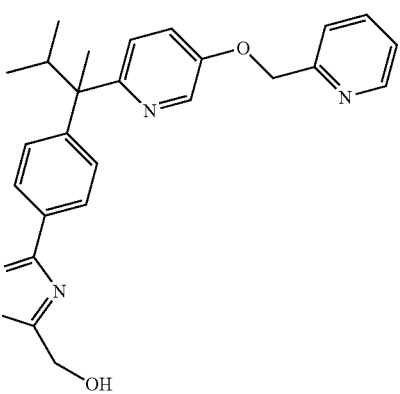
3d
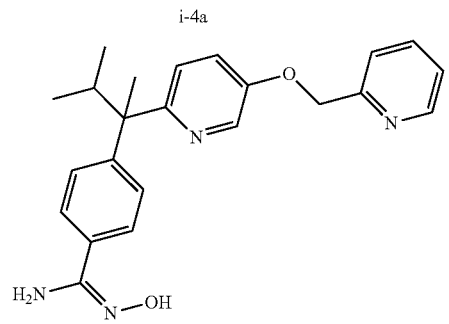
3a
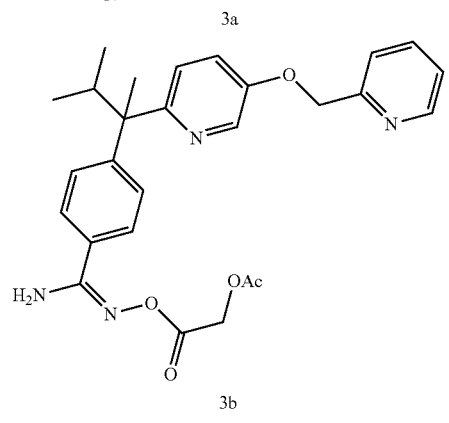
3b
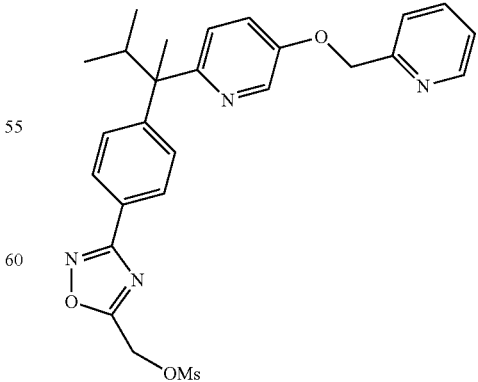
3e

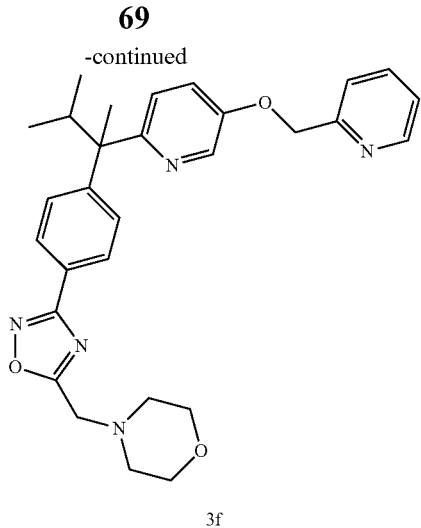

3f

Preparation of 3f

Step A: Preparation of 4-{1,2-dimethyl-1-[5-(pyridin-2-ylmethoxy)pyridin-2-yl]propyl}-N'-hydroxybenzenecarboximidamide (3a)

Hydroxylamine (483 µL of a 50% solution in H$_2$O, 7.35 mmol) was added to a stirred solution of i-4a (877 mg, 2.45 mmol) in EtOH (22.0 mL) at rt, and the resulting mixture was heated to 80° C. for approximately 3 h. After cooling to rt, the reaction mixture was concentrated in vacuo, and the crude residue was purified by flash chromatography on silica gel (gradient elution; 0%-4% MeOH/DCM as eluent) to furnish the title compound 3a. m/z (ES) 391 (MH)$^+$. $^1$HNMR. (500 MHz, CD$_3$OD): δ 8.55 (d, 1H, J=3.7 Hz), 8.26 (d, 1H, J=3.0 Hz), 7.88 (dt, 1H, J=1.7, 7.8 Hz), 7.61 (d, 1H, J=7.5 Hz), 7.52 (d, 2H, J=8.5 Hz), 7.37 (m, 4H), 7.29 (d, 1H, J=8.9 Hz), 5.22 (s, 2H), 3.05 (m, 1H, J=6.8 Hz), 1.67 (s, 3H), 0.84 (d, 3H, J=6.7 Hz), 0.78 (d, 3H, J=6.9 Hz).

Step B: Preparation of 2-({[(1E)-amino(4-{1,2-dimethyl-1-[5-(pyridin-2-ylmethoxy)pyridin-2-yl]propyl}phenyl)methylene]amino}-2-oxoethyl acetate (3b)

Compound 3a (350 mg, 0.896 mmol) was added to a stirred solution of acetoxyacetic acid (126 mg, 1.07 mmol), EDC (205 mg, 1.07 mmol) and HOBt (157 mg, 1.16 mmol) in DCM (7.00 mL) at rt. After approximately 45 min, the reaction mixture was poured into saturated aqueous sodium bicarbonate and extracted three times with EtOAc. The combined organic extracts were washed with water, brine, dried (sodium sulfate) and concentrated in vacuo to afford the title compound 3b, which was used without further purification in the subsequent reaction. m/z (ES) 491 (MH)$^+$.

Step C: Preparation of [3-(4-{1,2-dimethyl-1-[5-(pyridin-2-ylmethoxy)pyridin-2-yl]propyl}phenyl)-1,2,4-oxadiazol-5-yl]methyl acetate (3c)

A stirred solution of 3b (0.896 mmol) in xylene (6.00 mL) was heated to 110° C. for approximately 1 h. After cooling to rt, the reaction mixture was concentrated in vacuo to afford the title compound 3c, which was used without further purification in the subsequent reaction. m/z (ES) 473 (MH)$^+$.

Step D: Preparation of [3-(4-{1,2-dimethyl-1-[5-(pyridin-2-ylmethoxy)pyridin-2-yl]propyl}phenyl)-1,2,4-oxadiazol-5-yl]methanol (3d)

Potassium carbonate (743 mg, 5.38 mmol) in water (1.00 mL) was added to a stirred solution of 3c (0.896 mmol) in MeOH (3.00 mL) at rt. After approximately 1 h, the reaction mixture was poured into saturated aqueous sodium bicarbonate and extracted three times with EtOAc. The combined organic extracts were washed with water, brine, dried (sodium sulfate) and concentrated in vacuo. The crude residue was purified by flash chromatography on silica gel (gradient elution; 0%-6% MeOH/DCM as eluent) to furnish the title compound 3d. m/z (ES) 431 (MH)$^+$. $^1$HNMR. (500 MHz, CD$_3$OD): δ 8.55 (d, 1H, J=3.3 Hz), 8.28 (d, 1H, J=2.7 Hz), 7.94 (d, 2H, J=8.5 Hz), 7.88 (dt, 1H, J=1.7, 7.7 Hz), 7.61 (d, 1H, J=7.8 Hz), 7.48 (d, 2H, J=8.5 Hz), 7.35 (m, 3H), 5.23 (s, 2H), 3.08 (m, 1H, J=6.6 Hz), 1.70 (s, 3H), 0.86 (d, 3H, J=6.6 Hz), 0.80 (d, 3H, J=6.6 Hz).

Step E: Preparation of [3-(4-{1,2-dimethyl-1-[5-(pyridin-2-ylmethoxy)pyridin-2-yl]propyl}phenyl)-1,2,4-oxadiazol-5-yl]methyl methanesulfonate (3e)

Methanesulfonyl chloride (27.0 µL, 0.348 mmol) was added to a stirred solution of 3d (100 mg, 0.232 mmol) and DIPEA (101 µL, 0.580 mmol) in DCM (2.00 mL) at 0° C. After approximately 1.5 h, the reaction mixture was poured into water and extracted three times with EtOAc. The combined organic extracts were washed with water, brine, dried (sodium sulfate) and concentrated in vacuo to afford the title compound 3e, which was used without further purification in the subsequent reaction.

Step F: Preparation of 4-{[3-(4-{1,2-dimethyl-1-[5-(pyridin-2-ylmethoxy)pyridin-2-yl]propyl}phenyl)-1,2,4-oxadiazol-5-yl]methyl}morpholine (3f)

Morpholine (101 µL, 1.16 mmol) was added to a stirred solution of 3e (0.116 mmol) and tetrabutylammonium iodide (47.0 mg, 0.127 mmol) in DMF (1.00 mL) at rt. After approximately 2 h, the reaction mixture was poured into saturated aqueous sodium bicarbonate and extracted three times with EtOAc. The combined organic extracts were washed with water, brine, dried (sodium sulfate) and concentrated in vacuo. The crude residue was purified by flash chromatography on silica gel (gradient elution; 0%-5% MeOH/DCM as eluent) to furnish a mixture of the title compound 3f and tetrabutylammonium iodide. The mixture was dissolved in EtOAc, washed several times with water, brine, dried (sodium sulfate) and concentrated in vacuo to afford the title compound, 3f. m/z (ES) 500 (MH)$^+$. $^1$HNMR (500 MHz, CD$_3$OD): δ 8.90 (d, 1H, J=5.0 Hz), 8.60 (m, 2H), 8.31 (dd, 1H, J=3.0, 9.4 Hz), 8.18 (d, 1H, J=8.2 Hz), 8.13 (m, 3H), 8.03 (m, 1H), 7.55 (d, 2H, J=8.5 Hz), 5.74 (s, 2H), 4.96 (s, 2H), 4.00 (br, 4H), 3.62 (br, 4H), 3.05 (m, 1H, J=6.7 Hz), 1.88 (s, 3H), 0.98 (d, 3H, J=6.6 Hz), 0.92 (d, 3H, J=6.6 Hz).

Following procedures similar to that described above for compounds 3c and 3f, the following additional compounds can be prepared (Table 3):

TABLE 3
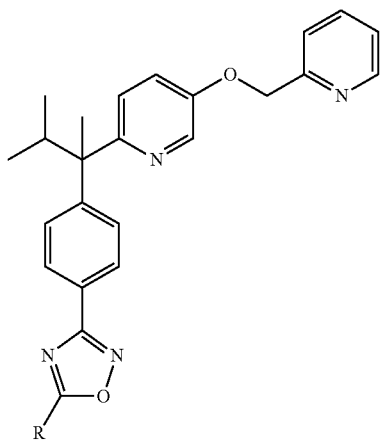
3A
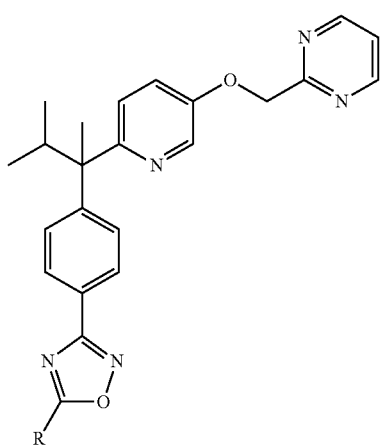
3B
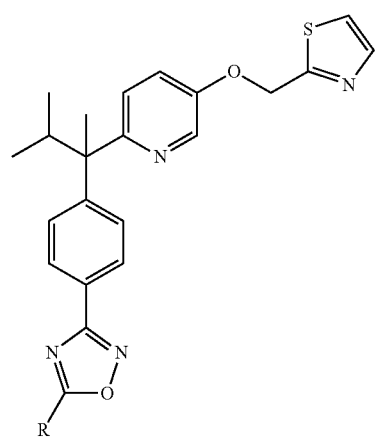
3C

TABLE 3-continued
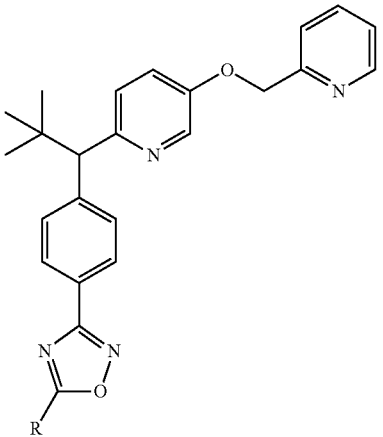
3D
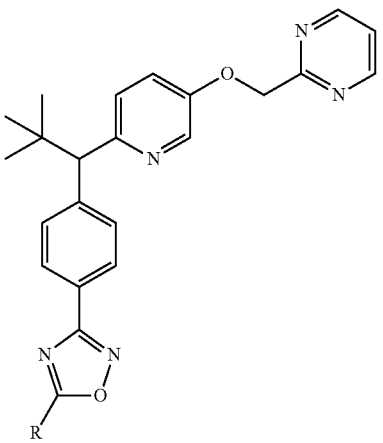
3E
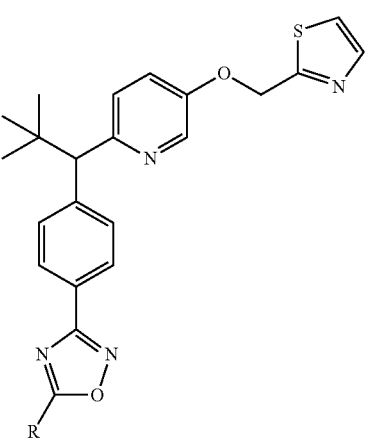
3F
| Ex. #3A | Ex. #3B | Ex. #3C | Ex. #3D | Ex. #3E | Ex. #3F | R |
|---------|---------|---------|---------|---------|---------|---|
| a | a | a | a | a | a |  |
| — | b | b | b | b | b | —CH$_2$OH |
| c | c | c | c | c | c | 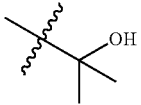 [SMILES: *C(C)(C)O] |

TABLE 3-continued
| | | | | | | |
|---|---|---|---|---|---|---|
| d | d | d | d | d | d | 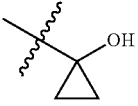 |
| — | e | e | e | e | e | 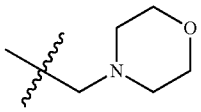 [SMILES: *CN1CCOCC1] |
| f | f | f | f | f | f | 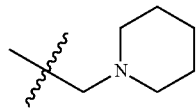 [SMILES: *CN1CCCCC1] |
| g | g | g | g | g | g | 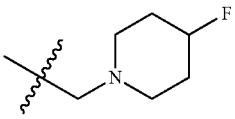 [SMILES: *CN1CCC(F)CC1] |
| h | h | h | h | h | h | 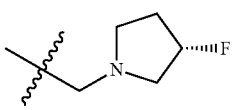 [SMILES: *CN1CC[C@H](F)C1] |
| i | i | i | i | i | i | 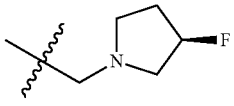 [SMILES: *CN1CC[C@@H](F)C1] |
| j | j | j | j | j | j | 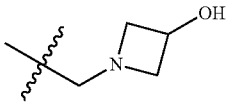 [SMILES: *CN1CC(O)C1] |
| k | k | k | k | k | k | 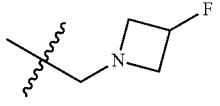 [SMILES: *CN1CC(F)C1] |
| l | l | l | l | l | l | 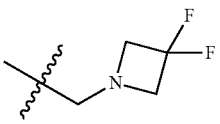 [SMILES: *CN1CC(F)(F)C1] |
| m | m | m | m | m | m | 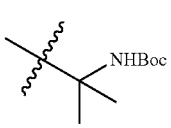 [SMILES: *C(C)(C)NC(=O)OC(C)(C)C] |
| n | n | n | n | n | n | 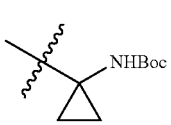 [SMILES: *C1(NC(=O)OC(C)(C)C)CC1] |
Table 3. Parent Ion m/z (MH)+ data for compounds 3Aa: 484; 3Ac: 459; 3Ad: 457; 3Af: 498; 3Ag: 516; 3Ah: 502; 3Ai: 502; 3Aj: 486; 3Ak: 488; 3Al: 506; 3Am: 559; 3An: 557; 3Bb: 432; 3Be: 501; 3Bg: 517; 3Ca: 490; 3Cb: 437; 3Cc: 465; 3Cd: 463; 3Ce: 506; 3Cf: 504; 3Cg: 522; 3Ch: 508; 3Ci: 508; 3Cj: 492; 3Ck: 494; 3Cl: 512.

EXAMPLE 4

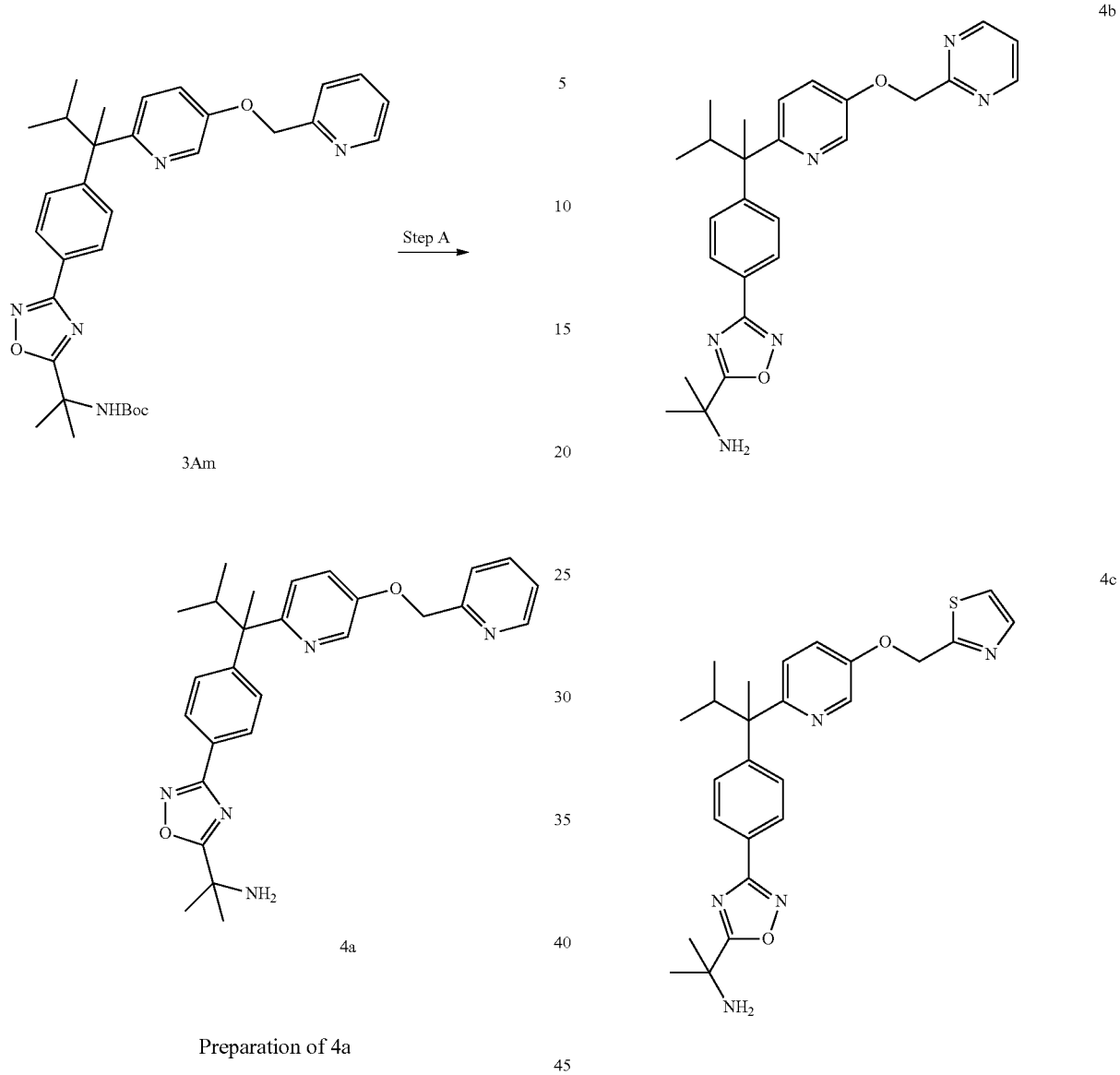

Preparation of 4a

Step A: Preparation of 2-[3-(4-{1,2-dimethyl-1-[5-(pyridin-2-ylmethoxy)pyridin-2-yl]propyl}phenyl)-1,2,4-oxadiazol-5-yl]propan-2-amine (4a)

Aqueous HCl (190 μL of a 4.0 M 1,4-dioxane solution in 10.0 μL water) was added to a stirred solution of 3Am (0.036 mmol) in 1,4-dioxane (100 μL) at 10° C., and the resulting mixture was allowed to warm to rt. After approximately 2 h, the reaction mixture was poured into saturated aqueous sodium bicarbonate and extracted three times with EtOAc. The combined organic extracts were washed with water, brine, dried (sodium sulfate) and concentrated in vacuo. The crude residue was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 4a. m/z (ES) 458 (MH)$^+$.

Following procedures similar to that described above for compound 4a, the following additional compounds 4b-4-f can be prepared:

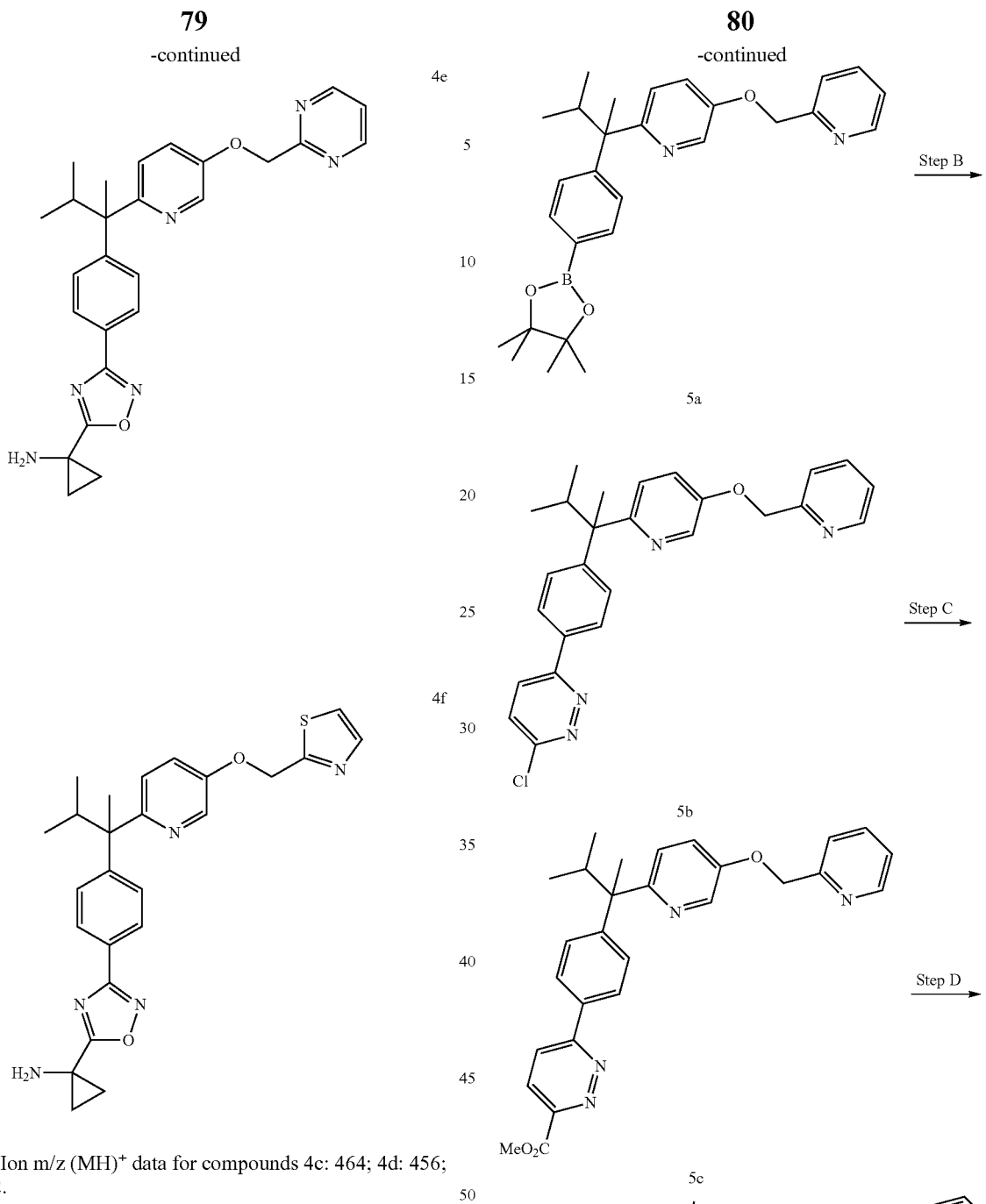
Parent Ion m/z (MH)+ data for compounds 4c: 464; 4d: 456; 4f: 462.
EXAMPLE 5
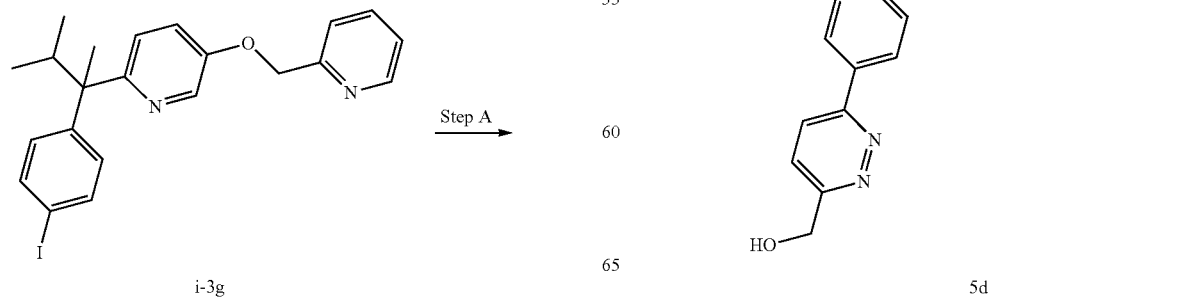

Preparation of 5e

Step A: Preparation of 2-{1,2-dimethyl-1-[4-(4,4,5,5-tetramethyl-1,3,2-dioxaborolan-2-yl)phenyl]propyl}-5-(pyridin-2-ylmethoxy)pyridine (5a)

[1,1'-Bis(diphenylphosphino)ferrocene]dichloropalladium(II) (120 mg, 0.164 mmol) was added to a stirred suspension of i-3g (3.278 mmol), bis(pinacolato)diboron (1.08 g, 4.26 mmol) and potassium acetate (960 mg, 9.85 mmol) in DMSO (10.0 mL) at rt. The resulting suspension was heated to 80° C. for approximately 1.5 h. After cooling to rt, the reaction mixture was diluted with EtOAc and filtered through a short column of CELITE®, eluting with EtOAc. The filtrate was washed with water, brine, dried (sodium sulfate) and concentrated in vacuo. The crude residue was purified by flash chromatography on silica gel (gradient elution; 10%-50% EtOAc/hexanes as eluent) to furnish the title compound 5a. $^1$HNMR (500 MHz, CDCl$_3$): δ 8.61 (d, 1H, J=4.6 Hz), 8.37 (d, 1H, J=2.8 Hz), 7.73 (m, 1H), 7.71 (d, 2H, J=8.0 Hz), 7.52 (d, 1H, J=7.8 Hz), 7.36 (d, 2H, J=8.0 Hz), 7.26 (m, 1H), 7.14 (dd, 1H, J=3.0, 8.9 Hz), 7.09 (d, 1H, J=8.7 Hz), 5.22 (s, 2H), 3.04 (m, 1H), 1.33 (s, 12H), 1.26 (s, 3H), 0.84 (d, 3H, J=6.6 Hz), 0.78 (d, 3H, J=6.6 Hz).

Step B: Preparation of 3-chloro-6-(4-{1,2-dimethyl-1-[5-(pyridin-2-ylmethoxy)pyridin-2-yl]propyl}phenyl)pyridazine (5b)

[1,1'-Bis(diphenylphosphino)ferrocene]dichloropalladium(II) (69.0 mg, 0.0950 mmol) was added to a stirred solution of 5a (1.45 g, 3.16 mmol), 3,6-dichloropyridazine (660 mg, 4.43 mmol) and sodium carbonate (3.20 mL of a 2.0 M aqueous solution, 6.32 mmol) in EtOH:toluene (10.0 mL of an 80:20 mixture, respectively) at rt. The resulting solution was heated to 95° C. for approximately 4 h. After cooling to rt, the reaction mixture was filtered through a short column of CELITE®, eluting with EtOAc. The filtrate was washed with water, brine, dried (sodium sulfate) and concentrated in vacuo. The crude residue was purified by flash chromatography on silica gel (gradient elution; 20%-80% EtOAc/hexanes as eluent) to furnish the title compound 5b. m/z (ES) 445 (MH)$^+$. $^1$HNMR (500 MHz, CDCl$_3$): δ 8.63 (d, 1H, J=4.1 Hz), 8.41 (d, 1H, J=1.8 Hz), 7.96 (d, 2H, J=8.7 Hz), 7.80 (d, 1H, J=8.9 Hz), 7.76 (dt, 1H, J=1.7, 7.7 Hz), 7.53 (m, 4H), 7.27 (dd, 1H, J=5.1, 7.1 Hz), 7.19 (m, 2H), 5.24 (s, 2H), 3.11 (m, 1H, J=6.7 Hz), 1.61 (s, 3H), 0.89 (d, 3H, J=6.6 Hz), 0.83 (d, 3H, J=6.9 Hz).

Step C: Preparation of methyl 6-(4-{1,2-dimethyl-1-[5-(pyridin-2-ylmethoxy)pyridin-2-yl]propyl}phenyl)pyridazine-3-carboxylate (5c)

Palladium (II) acetate (8.00 mg, 0.0350 mmol) and 1,1'-bis(diphenylphosphino)ferrocene (39.0 mg, 0.070 mmol) were added successively to a stirred solution of 5b (155 mg, 0349 mmol) in triethylamine:DMF:MeOH (4.00 mL of a 1:10:10 mixture, respectively) at rt. A gentle stream of the carbon monoxide gas was bubbled through the reaction mixture for approximately 15 min, after which the resulting mixture was heated to 70° C. under a carbon monoxide atmosphere (balloon) for about 5 h. After cooling to rt, the reaction mixture was filtered through a short column of CELITE®, eluting with DCM. The filtrate was partially concentrated in vacuo and diluted with EtOAc. The organic phase was washed with water, brine, dried (sodium sulfate) and concentrated in vacuo. Purification of the crude residue by flash chromatography on silica gel (gradient elution; 30%-100% EtOAc/hexanes as eluent) afforded the title compound 5c. m/z (ES) 469 (MH)$^+$. $^1$HNMR (500 MHz, CDCl$_3$): δ 8.62 (d, 1H, J=4.8 Hz), 8.41 (m, 1H), 8.22 (d, 1H, J=8.7 Hz), 8.08 (d, 2H, J=8.8 Hz), 7.96 (d, 1H, J=8.9 Hz), 7.75 (dt, 1H, J=1.7, 7.7 Hz), 7.56 (d, 2H, J=8.7 Hz), 7.53 (d, 1H, J=7.8 Hz), 7.26 (dd, 1H, J=5.2, 7.3 Hz), 7.19 (m, 2H), 5.23 (s, 2H), 4.10 (s, 3H), 3.11 (m, 1H, 6.6 Hz), 1.73 (s, 3H), 0.89 (d, 3H, J=6.7 Hz), 0.83 (d, 3H, J=6.8 Hz).

Step D: Preparation of [6-(4-{1,2-dimethyl-1-[5-(pyridin-2-ylmethoxy)pyridin-2-yl]propyl}phenyl)pyridazin-3-yl]methanol (5d)

Sodium borohydride (14.0 mg, 0.362 mmol) was added to a stirred solution of 5c (113 mg, 0.241 mmol) in EtOH (2.00 mL) at 0° C., and the resulting mixture was allowed to warm to rt. After approximately 12 h, the reaction mixture was cooled to 0° C. and quenched by the addition of aqueous 1N HCl. The resulting mixture was poured into saturated aqueous sodium bicarbonate and extracted three times with EtOAc. The combined organic extracts were washed with brine, dried (sodium sulfate) and concentrated in vacuo. Purification of the crude residue by flash chromatography on silica gel (gradient elution; 30%-100% EtOAc/hexanes as eluent) afforded the title compound 5d. m/z (ES) 441 (MH)$^+$. $^1$HNMR (500 MHz, CDCl$_3$): δ 8.61 (d, 1H, J=3.2 Hz), 8.40 (m, 1H), 7.97 (d, 2H, J=8.2 Hz), 7.83 (d, 1H, J=8.7 Hz), 7.75 (m, 1H), 7.52 (m, 4H), 7.26 (m, 1H), 7.19 (m, 2H), 5.23 (s, 2H), 3.09 (m, 1H, J=6.6 Hz), 1.72 (s, 3H), 0.88 (d, 3H, J=6.6 Hz), 0.83 (d, 3H, J=6.6 Hz).

Compound 5e was prepared from 5d following procedures similar to that described for compound 3f.

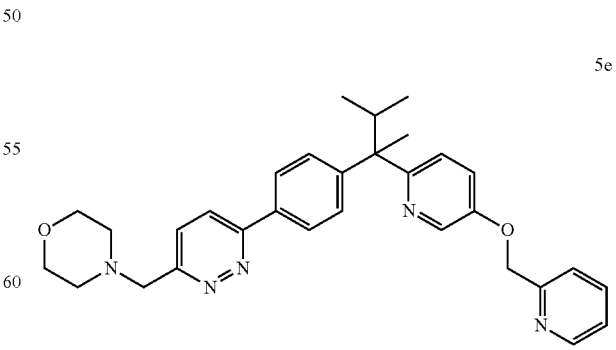

5e

Following procedures similar to that described above in Example 5, the following compounds can be prepared (Table 5):

TABLE 5
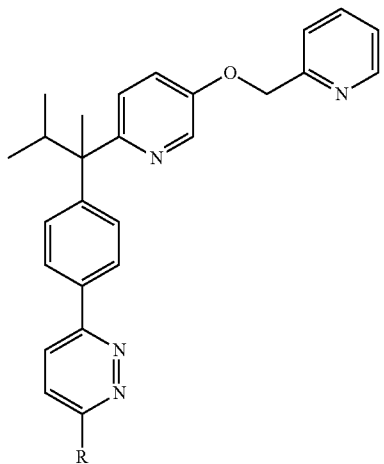
5A
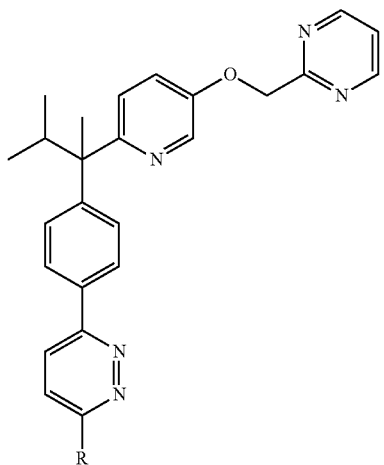
5B
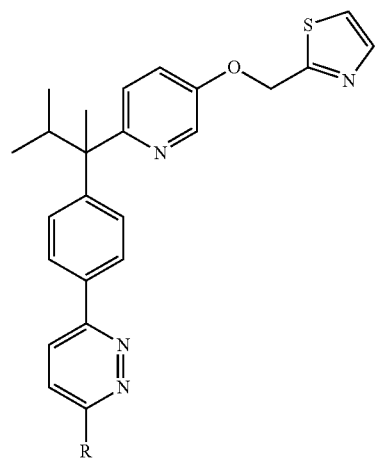
5C

TABLE 5-continued
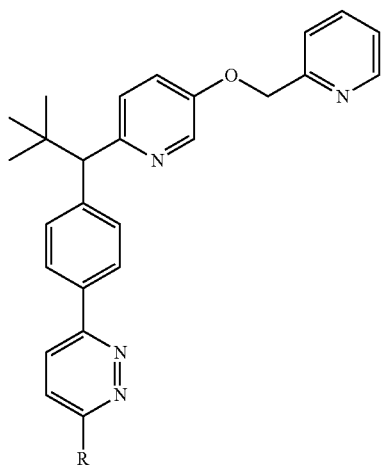
5D
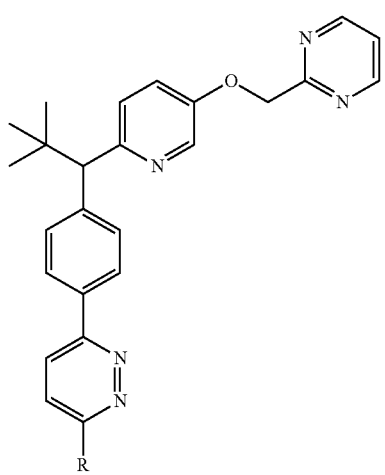
5E
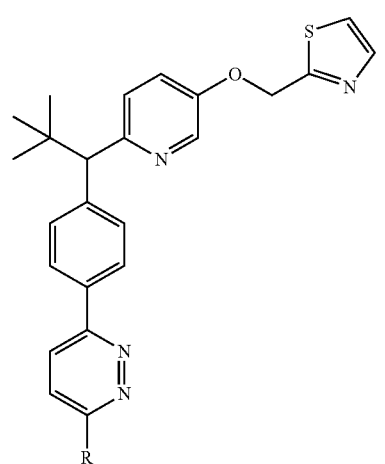
5F
| Ex. #5A | Ex. #5B | Ex. #5C | Ex. #5D | Ex. #5E | Ex. #5F | R |
|---|---|---|---|---|---|---|
| — | a | a | a | a | a | CO₂Me |
| — | b | b | b | b | b | —CH₂OH |
| — | c | c | c | c | c |  |

TABLE 5-continued

| | | | | | | |
|---|---|---|---|---|---|---|
| d | d | d | d | d | d | CH₃ |
| e | e | e | e | e | e | CF₃ |
| f | f | f | f | f | f | *piperidinylmethyl* |
| g | g | g | g | g | g | *4-fluoropiperidinylmethyl* |
| h | h | h | h | h | h | *pyrrolidinylmethyl* |
| i | i | i | i | i | i | *(R)-3-fluoropyrrolidinylmethyl* |
| j | j | j | j | j | j | *(S)-3-fluoropyrrolidinylmethyl* |
| k | k | k | k | k | k | *3-hydroxyazetidinylmethyl* |
| l | l | l | l | l | l | *3-fluoroazetidinylmethyl* |
| m | m | m | m | m | m | *3,3-difluoroazetidinylmethyl* |
| n | n | n | n | n | n | NH₂[1] |
| o | o | o | o | o | o | OH[2] |
| p | p | p | p | p | p | SO₂Me[3] |

Table 5. Parent Ion m/z (MH)⁺ data for compounds 5Ae: 479; 5Af: 508; 5Ag: 526; 5Ah: 494; 5Ai: 512; 5Aj: 512; 5Ba: 470; 5Cc: 516; 5Cd: 431; 5Ce: 485; 5Cg: 532; 5Ch: 500; 5Ci: 518; 5Cj: 518; 5Ck: 502; 5Cl: 504.

[1] Appropriate protection of the NH₂ group is required during Step B. For example, the NH₂ functionality can be protected as the 2,5-dimethylpyrrole derivative and then removed using known methods.

[2] Appropriate protection of the OH group is required during Step B. For example, the OH functionality can be protected with either trialkylsilyl groups such as t-butyldimethylsilyl, and then removed using known methods.

[3] The SO₂Me group can be introduced via reaction of 5b with sodium methanesulfinate according to the method of Miyashita et al described in Heterocycles 1994, 39(1), 345-356.

EXAMPLE 6

Step A
5c →

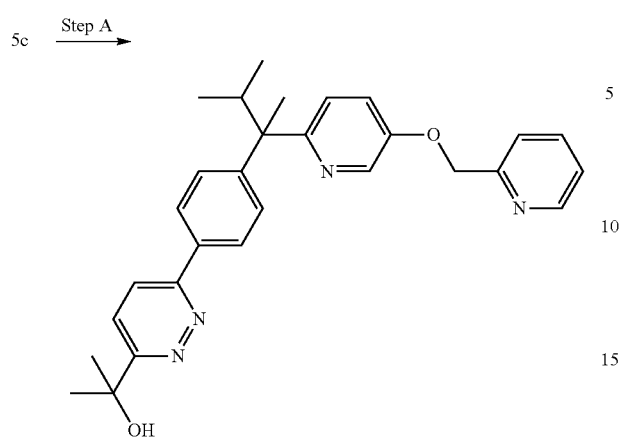

Step A: Preparation of 2-[6-(4-{1,2-dimethyl-1-[5-(pyridin-2-ylmethoxy)pyridin-2-yl]propyl}phenyl)pyridazin-3-yl]propan-2-ol (6a)

Methyl magnesium bromide (1.70 mL of a 1.4 M (75:25) toluene:THF solution) was added to a stirred solution of 5c (474 mg, 1.02 mmol) in THF (5.00 mL) at 0° C. After approximately 45 min, the reaction was quenched by addition of aqueous 1N HCl, and the resulting mixture was poured into saturated aqueous sodium bicarbonate and extracted three times with EtOAc. The combined organic extracts were washed with brine, dried (sodium sulfate) and concentrated in vacuo. The crude residue was purified by preparative reversed phase HPLC on YMC Pack Pro C18 stationary phase ($CH_3CN/H_2O$ as eluent, 0.05% TFA as modifier), followed by lyophilization of the purified fractions to afford the title compound 6a. m/z (ES) 469 (MH)$^+$. $^1$HNMR (500 MHz, $CD_3OD$): δ 8.97 (d, 1H, J=9.1 Hz), 8.94 (d, 1H, J=5.5 Hz), 8.68 (m, 3H), 8.40 (dd, 1H, J=3.0, 9.1 Hz), 8.25 (m, 1H), 8.24 (d, 2H, J=8.7 Hz), 8.20 (d, 1H, J=9.1 Hz), 8.10 (m, 1H), 7.67 (d, 2H, J=8.7 Hz), 5.81 (s, 2H), 3.10 (m, 1H, J=6.6 Hz), 1.92 (s, 3H), 1.74 (s, 6H), 1.01 (d, 3H, J=6.6 Hz), 0.96 (d, 3H, J=6.4 Hz).

Following procedures similar to that described for compound 6a, the following additional compounds 7d and 6b were prepared.

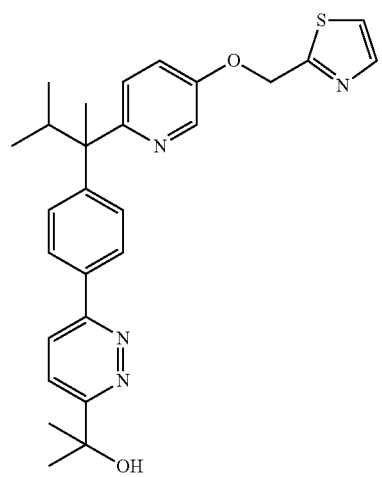

Parent Ion m/z (MH)$^+$ data for 2-[6-(4-{1,2-dimethyl-1-[5-(pyrimidin-2-ylmethoxy)pyridin-2-yl]propyl}phenyl)pyridazin-3-yl]propan-2-ol (7d): m/z (ES) 470 (MH)$^+$.

Parent Ion m/z (MH)$^+$ data for 2-[6-(4-{1,2-dimethyl-1-[5-(1,3-thiazol-2-ylmethoxy)pyridin-2-yl]propyl}phenyl)pyridazin-3-yl]propan-2-ol (6b): m/z (ES) 475 (MH)$^+$.

EXAMPLE 7

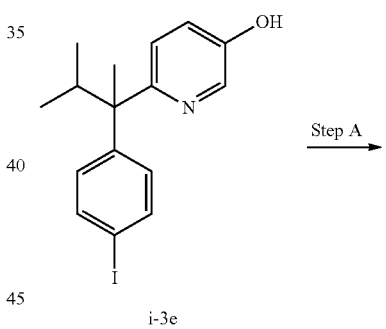

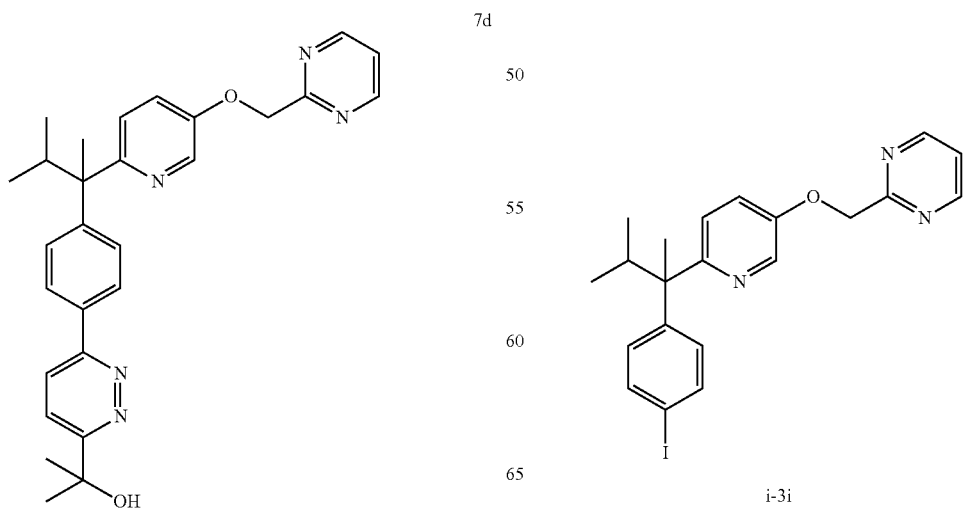

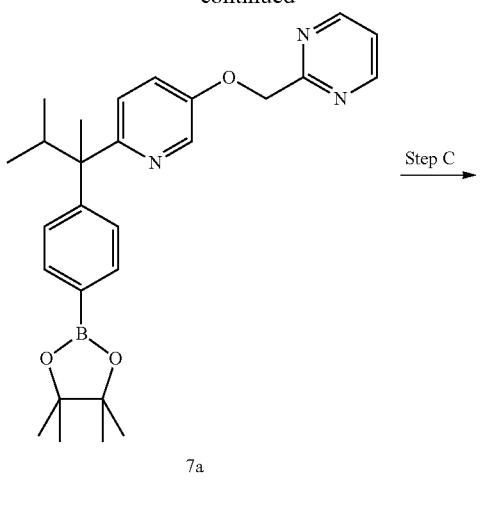

7a

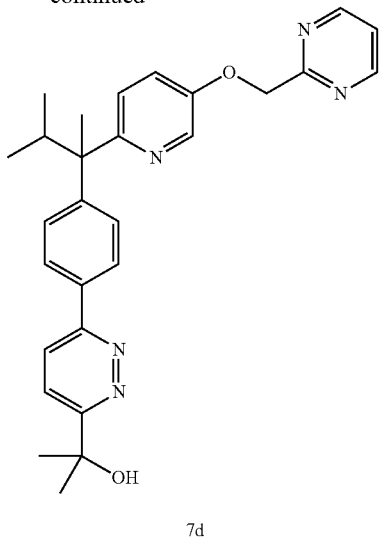

7d

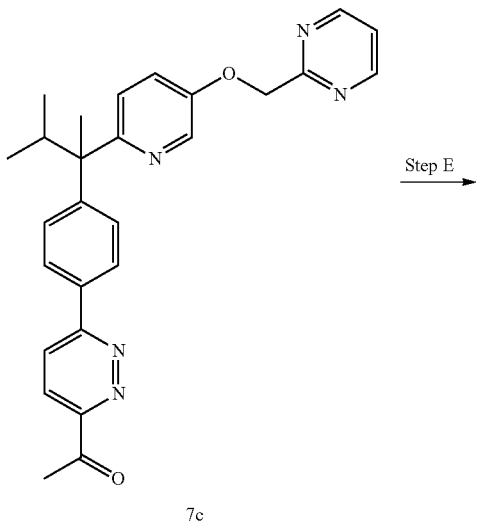

7b

Alternate Preparation of 7d

Step A: Preparation of 2-[({6-[1-(4-iodophenyl)-1,2-dimethylpropyl]pyridin-3-yl}oxy)methyl]pyrimidine (i-3i)

Cesium carbonate (20.6 g, 63.1 mmol), potassium iodide (7.48 g, 45.1 mmol), and i-2a (9.64 g, 51.8 mmol) were added to a stirred solution of i-3e (16.5 g, 45.1 mmol) in DMF (200 mL) at 0° C., and the resulting mixture was allowed to warm to rt. After approximately 12 h, the reaction mixture was poured into water and extracted three times with EtOAc. The combined organic extracts were washed with water twice, brine, dried (sodium sulfate) and concentrated in vacuo to afford the title compound i-3i. m/z (ES) 460 (MH)$^+$. $^1$HNMR (500 MHz, CDCl$_3$): δ 8.81 (d, 2H, J=5.0 Hz), 8.39 (d, 1H, J=3.0 Hz), 7.57 (d, 2H, J=8.4 Hz), 7.22 (dd, 1H, J=3.0, 8.9 Hz), 7.11 (m, 4H), 5.34 (s, 2H), 3.00 (m, 1H, J=6.7 Hz), 1.63 (s, 3H), 0.83 (d, 3H, J=6.6 Hz), 0.77 (d, 3H, J=6.6 Hz).

Step B: Preparation of 2-{[(6-{1,2-dimethyl-1-[4-(4,4,5,5-tetramethyl-1,3,2-dioxaborolan-2-yl)phenyl]propyl}pyridin-3-yl)oxy]methyl}pyrimidine (7a)

[1,1'-Bis(diphenylphosphino)ferrocene]dichloropalladium(II) (2.30 g, 3.15 mmol) was added to a stirred suspension of i-3i (20.6 g, 45.0 mmol), bis(pinacolato)diboron (12.0 g, 47.3 mmol) and potassium acetate (13.2 g, 135 mmol) in DMSO (200 mL) at rt. The resulting suspension was degassed and heated to 70° C. for approximately 1.5 h. After cooling to rt, the reaction mixture was diluted with EtOAc and filtered through a short column of CELITE®, eluting with EtOAc. The filtrate was washed with water twice, brine, dried (sodium sulfate) and concentrated in vacuo. The crude residue was purified by flash chromatography on silica gel (gradient elution; 10%-80% EtOAc/hexanes as eluent) to furnish the title compound 7a. $^1$HNMR (500 MHz, CDCl$_3$): δ 8.81 (d, 2H, J=4.8 Hz), 8.39 (d, 1H, J=3.0 Hz), 7.72 (d, 2H, J=8.2 Hz), 7.36 (d, 2H, J=8.3 Hz), 7.28 (m, 1H), 7.20 (dd, 1H, J=3.1, 8.8 Hz), 7.10 (d, 1H, J=8.9 Hz), 5.34 (s, 2H), 3.05 (m, 1H, J=6.7 Hz), 1.68 (s, 3H), 1.35 (s, 12H), 0.85 (d, 3H, J=6.6 Hz), 0.79 (d, 3H, J=6.6 Hz).

Step C: Preparation of 3-(1-butoxyvinyl)-6-(4-{1,2-dimethyl-1-[5-(pyrimidin-2-ylmethoxy)pyridin-2-yl]propyl}phenyl)pyridazine (7b)

[1,1'-Bis(diphenylphosphino)ferrocene]dichloropalladium(II) (3.05 g, 4.17 mmol) was added to a stirred solution of 7a (19.2 g, 41.7 mmol), i-5a (10.6 g, 50.1 mmol) and sodium carbonate (42.0 mL of a 2.0 M aqueous solution, 84.0 mmol) in EtOH:toluene (140 mL of an 80:20 mixture, respectively) at rt. The resulting solution was degassed and heated to 95° C. for approximately 3.5 h. After cooling to rt, the reaction mixture was partially concentrated in vacuo and diluted with EtOAc. The resulting mixture was filtered through a short column of CELITE®, eluting with EtOAc. The filtrate was washed with saturated aqueous sodium bicarbonate, brine, dried (sodium sulfate) and concentrated in vacuo. The crude residue was purified by flash chromatography on silica gel (gradient elution; 10%-50% EtOAc/hexanes as eluent) to furnish the title compound 7b. m/z (ES) 510 (MH)+. 1HNMR (500 MHz, CDCl3): δ 8.82 (d, 2H, J=5.0 Hz), 8.43 (d, 1H, J=3.0 Hz), 8.04 (d, 2H, J=8.5 Hz), 7.84 (m, 2H), 7.53 (d, 2H, J=8.7 Hz), 7.30 (m, 1H), 7.24 (dd, 1H, J=2.9, 8.8 Hz), 7.18 (d, 1H, J=8.9 Hz), 5.83 (d, 1H, J=2.3 Hz), 5.36 (s, 2H), 4.53 (d, 1H, J=2.3 Hz), 3.99 (t, 2H, J=6.4 Hz), 3.11 (p, 1H, J=6.7 Hz), 1.86 (m, 2H), 1.73 (s, 3H, 1.56 (m, 2H), 1.04 (t, 3H, J=7.3 Hz), 0.89 (d, 3H, J=6.6 Hz), 0.84 (d, 3H, J=6.7 Hz).

Step D: Preparation of 1-[6-(4-{1,2-dimethyl-1-[5-(pyrimidin-2-ylmethoxy)pyridin-2-yl]propyl}phenyl)pyridazin-3-yl]ethanone (7c)

Hydrochloric acid (100 mL of a 1.0 M solution in EtOH) was added to a stirred solution of 7b (15.8 g, 30.9 mmol) in EtOH (25.0 mL) at 0° C. After approximately 15 min, a second portion of hydrochloric acid (150 mL of a 2.0 M aqueous solution) was added, and after another 15 min, a third portion of hydrochloric acid (100 mL of a 6.0 M aqueous solution) was added. After an additional 10 min, the reaction was warmed to rt and aged for 30 min. The reaction was diluted with water, recooled to 0° C. and neutralized by the addition of solid sodium bicarbonate. The resulting mixture was saturated with solid sodium chloride and extracted twice with EtOAc. The combined organic extracts were washed with brine, dried (sodium sulfate) and concentrated in vacuo to afford the title compound 7c m/z (ES) 454 (MH)+. 1HNMR (500 MHz, CDCl3): δ 8.80 (d, 2H, J=4.8 Hz), 8.42 (d, 1H, J=3.0 Hz), 8.16 (d, 1H, J=8.7 Hz), 8.08 (d, 2H, J=8.5 Hz), 7.98 (d, 1H, J=8.9 Hz), 7.56 (d, 2H, J=8.5 Hz), 7.27 (m, 1H), 7.24 (dd, 1H, J=3.0, 8.7 Hz), 7.18 (d, 1H, J=8.9 Hz), 5.34 (s, 2H), 3.10 (m, 1H, J=6.7 Hz), 2.94 (s, 3H), 1.73 (s, 3H), 0.88 (d, 3H, J=6.7 Hz), 0.83 (d, 3H, J=6.8 Hz).

Step E: Preparation of 2-[6-(4-{1,2-dimethyl-1-[5-(pyrimidin-2-ylmethoxy)pyridin-2-yl]propyl}phenyl)pyridazin-3-yl]propan-2-ol (7d)

Methyl magnesium bromide (30.9 mL of a 1.4 M solution in THF:toluene (25:75)) was added to a stirred solution of 7c (14.0 g, 30.9 mmol) in a mixture of THF (130 mL) and diethyl ether (260 mL) at 0° C. After approximately 1 h at 0° C., the reaction was quenched by the addition of saturated aqueous ammonium chloride, and the resulting mixture stirred for 15 min. The organic phase was separated, and the aqueous phase was extracted with EtOAc. The combined organic extracts were washed with brine, dried (magnesium sulfate) and concentrated in vacuo. The crude residue was purified by flash chromatography on silica gel (gradient elution; 0%-100% acetone/DCM as eluent) to furnish the title compound 7d. m/z (ES) 470 (MH)+.

1HNMR (500 MHz, CDCl3): δ 9.01 (d, 1H, J=9.1 Hz), 8.88 (d, 2H, J=5.0 Hz), 8.73 (d, 1H, J=9.2 Hz), 8.52 (d, 1H, J=2.7 Hz), 8.34 (dd, 1H, J=3.0, 9.4 Hz), 8.25 (d, 2H, J=8.5 Hz), 8.17 (d, 1H, J=9.1 Hz), 7.65 (d, 2H, J=8.5 Hz), 7.53 (t, 1H, J=5.0 Hz), 5.62 (s, 2H), 3.05 (m, 1H, J=6.7 Hz), 1.91 (s, 3H), 1.75 (s, 6H), 1.00 (d, 3H, J=6.6 Hz), 0.96 (d, 3H, J=6.4 Hz).

EXAMPLE 8

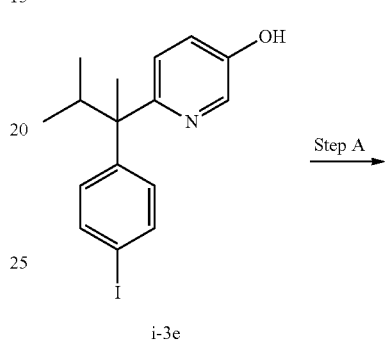

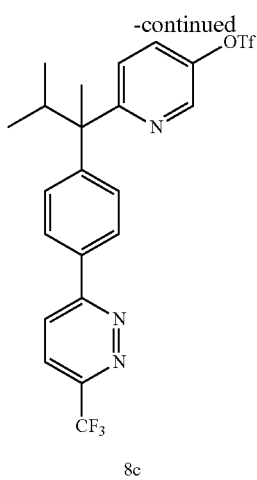

8c

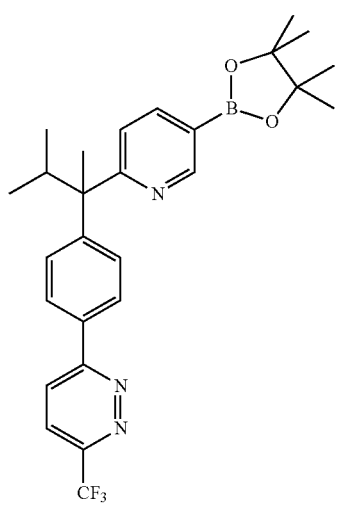

8d

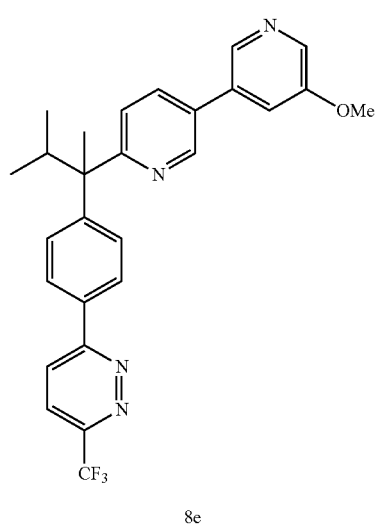

8e

Preparation of 8e and 8g

Step A: Preparation of 6-{1,2-dimethyl-1-[4-(4,4,5,5-tetramethyl-1,3,2-dioxaborolan-2-yl)phenyl]propyl}pyridin-3-ol (8a)

Compound 8a was prepared following procedures similar to those described for preparing compound 5a, substituting i-3e for i-3g. m/z (ES) 382 (MH)$^+$ Step B: Preparation of 6-(1,2-dimethyl-1-{4-[6-(trifluoromethyl)pyridazin-3-yl]phenyl}propyl)pyridin-3-ol (8b)

Compound 8b was prepared from 8a following procedures similar to those described for preparing compound 5b substituting compound 8a and 3-chloro-6-trifluoromethylpyridazine for compound 5a and 3,6-dichloropyridazine, respectively. m/z (ES) 402 (MH)$^+$ Step C: Preparation of 6-(1,2-dimethyl-1-{-4-[6-(trifluoromethyl)pyridazin-3-yl]phenyl}propyl)pyridin-3-1/1 trifluoromethanesulfonate (8c)

2-[N,N-Bis(trifluoromethansulfonyl)amino]pyridine (89.0 mg, 0.247 mmol) was added to a stirred solution of 8b (87.0 mg, 0.225 mmol), triethylamine (47.0 μL, 0.337 mmol) and DMAP (~2 mg) in DCM (2.00 mL) at rt. After approximately 1 h, the reaction mixture was concentrated in vacuo, and the crude residue was purified by flash chromatography on silica gel (gradient elution; 10%-20% EtOAc/hexanes as eluent) to afford the title compound 8c. m/z (ES) 520 (MH)$^+$.

Step D: Preparation of 3-(4-{1,2-dimethyl-1-[5-(4,4,5,5-tetramethyl-1,3,2-dioxaborolan-2-yl)pyridin-2-yl]propyl}phenyl)-6-(trifluoromethyl)pyridazine (8d)

[1,1'-Bis(diphenylphosphino)ferrocene]dichloropalladium(II) (21.0 mg, 0.0280 mmol) was added to a stirred suspension of 8c (98.0 mg, 0.189 mmol), bis(pinacolato)diboron (98.0 mg, 0.245 mmol) and potassium acetate (510 mg, 0.566 mmol) in DMSO (1.00 mL) at rt. The resulting suspension was heated to 80° C. for approximately 1.5 h.

After cooling to rt, the reaction mixture was diluted with EtOAc and filtered through a short column of CELITE®, eluting with EtOAc. The filtrate was washed with water, brine, dried (sodium sulfate) and concentrated in vacuo. The crude residue was purified by flash chromatography on silica gel (gradient elution; 10%-20% EtOAc/hexanes as eluent) to furnish the title compound 8d. m/z (ES) 416 (MH-C$_6$H$_{10}$)$^+$ Step E: Preparation of 6'-(1,2-dimethyl-1-{4-[6-(trifluoromethyl)pyridazin-3-yl]phenyl}propyl)-5-methoxy-3,3'-bipyridine (8e)

[1,1'-Bis(diphenylphosphino)ferrocene]dichloropalladium(II) (14.0 mg, 0.0190 mmol) was added to a stirred solution of 8d (47.0 mg, 0.0950 mmol), 3-bromo-5-methoxypyridine (23.0 mg, 4.43 mmol) and sodium carbonate (100 µL of a 2.0 M aqueous solution, 0.200 mmol) in EtOH:toluene (500 µL of an 80:20 mixture, respectively) at rt. The resulting solution was heated to 95° C. for approximately 5 h. After cooling to rt, the reaction mixture was filtered through a short column of CELITE®, eluting with EtOAc. The filtrate was washed with water, brine, dried (sodium sulfate) and concentrated in vacuo. The crude residue was purified by flash chromatography on silica gel (gradient elution; 20%-50% EtOAc/hexanes as eluent) to furnish the title compound 8e. m/z (ES) 479 (MH)$^+$.

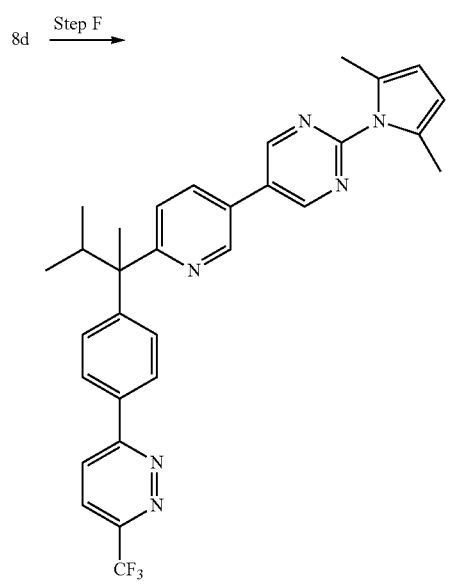

8d →Step F→ 8f →Step G→

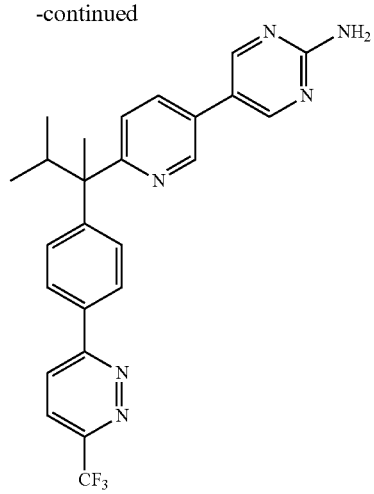

8g

Step F: Preparation of 3-[4-(1-{5-[2-(2,5-dimethyl-1H-pyrrol-1-yl)pyrimidin-5-yl]pyridin-2-yl}-1,2-dimethylpropyl)phenyl]-6-(trifluoromethyl)pyridazine (8f)

Compound 8f can be prepared from 8d following procedures similar to those described for compound 8e, substituting 5-bromo-2-(2,5-dimethyl-1H-pyrrol-1-yl)pyrimidine for 3-bromo-5-methoxypyridine.

Step G: Preparation of 5-[4-(1,2-dimethyl-1-{5-[6-(trifluoromethyl)pyridazin-3-yl]pyridin-2-yl}propyl)phenyl]pyrimidin-2-amine (8g)

Hydroxylamine hydrochloride (10.0 equiv.) is added to a stirred solution of 8e (1.00 equiv.) and triethylamine (0.50 equiv.) in EtOH/water (0.15M in a 2:1 mixture, respectively) at rt, and the resulting mixture is heated at 80° C. After the reaction is determined to be complete, the reaction mixture is cooled to rt, poured into saturated aqueous sodium bicarbonate and extracted three times with EtOAc. The combined organic extracts are washed with water and brine, dried (sodium sulfate) and concentrated in vacuo. The crude residue is purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 8g.

Following procedures similar to that described above in Examples 5-7 and 8, the following compounds can be prepared (Table 8):

TABLE 8

| Ex. #8A | Ex. #8B | Ex. #8C | R¹ |
|---|---|---|---|
| a | a | a | (t-butyl with OH) |
| — | b | b | (pyridazine-CF₃) |
| c | c | c | (pyridazine-C(CH₃)₂OH) |

Parent Ion m/z (MH)⁺ data for compounds 8Ac: 469.

FLAP Binding Assay

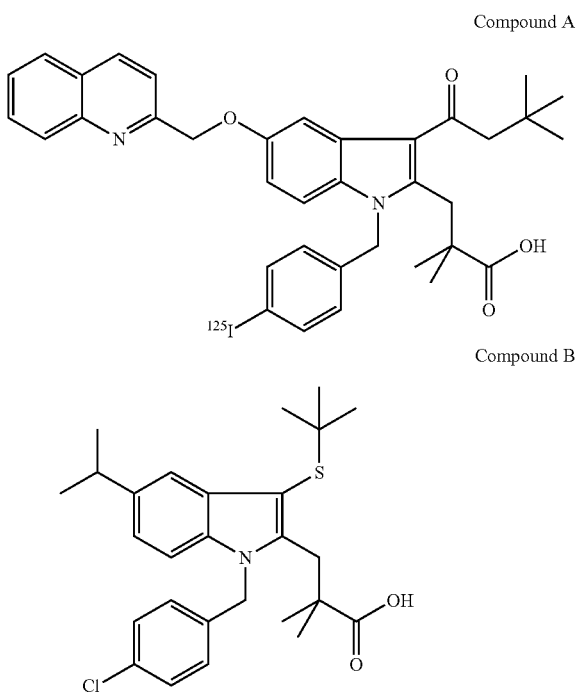

Compound A

Compound B

A 100,000×g pellet from human leukocyte 10,000×g supernatants (1) is the source of FLAP. The 100,000×g pellet membranes were resuspended in Tris-Tween assay buffer (100 mM Tris HCl pH 7.4, 140 mM NaCl, 2 mM EDTA, 0.5 mM dithiothreitol, 5% glycerol, 0.05% Tween 20) to yield a final protein concentration of 50 µg to 150 µg/ml. Aliquots (100 µl) of membrane suspension were added to 12 mm×75 mm polypropylene tubes containing 100 µl Tris-Tween assay buffer, 30,000 cpm of Compound A in 5 µl MeOH:assay buffer (1:1), and 2 µl dimethyl sulfoxide or competitor (i.e., the compound to be tested) in dimethyl sulfoxide. Compound B (10 µM final concentration) was used to determine non-specific binding. After a 20 minute incubation at room temperature, tube contents were diluted to 4 ml with cold 0.1 M Tris HCl pH 7.4, 0.05% Tween 20 wash buffer and the membranes were collected by filtration of GFB filters presoaked in the wash buffer. Tubes and filters were rinsed with 2×4 ml aliquots of cold wash buffer. Filters were transferred to 12 mm×3.5 mm polystyrene tubes for determination of radioactivity by gamma-scintillation counting.

Specific binding is defined as total binding minus non-specific binding. Total binding was Compound A bound to membranes in the absence of competitor; non-specific binding was Compound A bound in the presence of 10 uM Compound B. Preparation of Compound A is described in reference 1, below. The $IC_{50}$ values were obtained by computer analysis (see reference 2, below) of the experimental data. Representative tested compounds of the invention were determined to have $IC_{50}$'s less than 500 nM in the FLAP Binding Assay. Preferred representative tested compounds have an $IC_{50}$ that is 100 nM or less, and more preferable are those tested compounds having an $IC_{50}$ of 25 nM or less.

References

1. Charleson, S., Prasti, P., Leger, S., Gillard, J. W, Vickers, P. J., Mancini, J. A., Charleson, P., Guay, J., Ford-Hutchinson, A. W., and Evans, J. F. (1992) Characterization of a 5-lipoxygenase-activating protein binding assay: correlation of affinity for 5-lipoxygenase-activating protein with leukotriene synthesis inhibition. Mol Pharmacol 41:873-879.

2. Kinetic, EBDA, Ligand, Lowry: A collection of Radioligand Binding Analysis Programs by G. A. McPherson. Elsevier-BIOSOFT.

While the invention has been described with reference to certain particular embodiments thereof, numerous alternative embodiments will be apparent to those skilled in the art from the teachings described herein. Recitation of a specific compound in the claims (i.e., a species) without a chiral designation is intended to encompass the racemate, racemic mixtures, each individual enantiomer, a diastereoisomeric mixture and each individual diastereoisomer of the compound where such forms are possible due to the presence of one or more asymmetric centers. All patents, patent applications and publications cited herein are incorporated by reference in their entirety.

What is claimed is:

1. A compound represented by structural Formula II

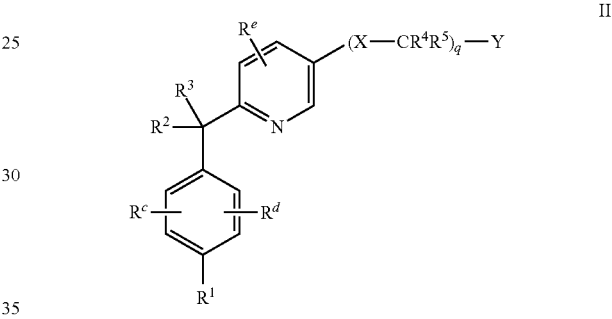

II and the pharmaceutically acceptable salts thereof wherein:

q is 0 (zero);

$R^1$ is selected from the group consisting of:
(a) a 5-membered aromatic or partially unsaturated heterocyclic ring containing 2 to 4 heteroatoms selected from N, S and O, wherein the heterocyclic ring is optionally substituted with $R^6$,
(b) a 6-membered aromatic or partially unsaturated heterocyclic ring containing 1 to 2 heteroatoms selected from N and O, wherein the heterocyclic ring is optionally substituted with $R^6$;
(c) an 8-membered aromatic or partially unsaturated ortho-fused bicyclic ring system containing 3-5 heteroatoms selected from one sulfur and 2-4 of nitrogen wherein one carbon in the ring is optionally substituted with a group selected from =O, =S, —SMe, —NH$_2$, —CF$_3$, —Cl, —C$_{1-4}$alkyl and C$_{1-4}$alkyl substituted with a group selected from —NH$_2$, —OH, —OC$_{1-4}$alkyl, —CN and 1-3 of fluoro,
(d) a 9-membered aromatic or partially unsaturated ortho-fused bicyclic ring system containing 3-4 nitrogen atoms, wherein one carbon in the ring is optionally substituted with a group selected from =O, =S, —SMe, —NH$_2$, —CF$_3$, —Cl, —C$_{1-4}$alkyl and —C$_{1-4}$ alkyl substituted with a group selected from —NH$_2$, —OH, —OC$_{1-4}$alkyl, —CN and 1-3 of fluoro;
(e) —C$_{1-6}$alkyl, —C$_{2-6}$alkenyl, and —C$_{2-6}$alkynyl, said alkyl, alkenyl and alkynyl groups being optionally substituted with $R^{12}$ and optionally substituted with $R^{13}$;

(f) —$C_{3-6}$ cycloalkyl optionally substituted with 1-3 substituents selected from the group consisting of fluoro, —$NH_2$, —OH and —$C_{1-3}$alkyl optionally substituted with 1-3 of fluoro;

(g) —O—$R^{6a}$; and (h) —H, —OH, —CN, —$CO_2R^4$, —C(O)$NR^7R^8$, —$NR^7R^8$, —$NR^bSO_pR^a$, —$NR^bC(O)R^a$, —$NR^bC(O)NR^aR^b$, —S(O)$_pR^a$, and —S(O)$_pNR^aR^b$;

p is an integer selected from 0, 1 and 2;

$R^2$ is selected from the group consisting of (a) —$C_{1-6}$alkyl optionally substituted with one or more substituents selected from the group consisting of —OH and fluoro (for example, 1-3 of fluoro), (b) —$C_{3-6}$ cycloalkyl optionally substituted with 1-3 of fluoro, and

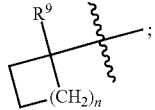 (c)

n is an integer selected from 0, 1, 2 and 3;

$R^3$ is selected from the group consisting of —H, —F, —OH, and —$C_{1-3}$alkyl optionally substituted with 1-5 fluoro (including for example —$CF_3$); or $R^2$ and $R^3$ are taken in combination and represent a mono- or bi-cyclic ring system containing 3 to 8 carbon atoms, said system being optionally substituted with 1-2 groups selected from: $C_{1-3}$alkyl, $OC_{1-3}$alkyl, F, OH, mono-, di- or tri-fluoro$C_{1-3}$alkyl and mono-, di- and tri-fluoro$C_{1-3}$ alkoxy;

$R^6$ is selected from the group consisting of (a) —$C_{1-6}$alkyl optionally substituted with one or more substituents selected from the group consisting of —OH, —$NH_2$, —CN, —O—$C_{1-4}$alkyl and fluoro (for example, 1-3 of fluoro), (b) —$C_{1-6}$alkyl-$R^{10}$, (c) —$OC_{1-6}$alkyl optionally substituted with one or more substituents selected from the group consisting of —OH, —$NH_2$ and fluoro, (d) —$C_{3-6}$ cycloalkyl optionally substituted with one or more substituents selected from the group consisting of methyl, —OH, —$NH_2$, —$CF_3$ and fluoro, (e) —$NR^7R^8$, (f) —$SO_2C_{1-3}$alkyl, (g) —$CO_2$—$R^8$, (h) —OH, (i) =O (oxo), (j) —SH, (k) =S, (l) —SMe, (m) —Cl, (n) —$CF_3$, (o) —CN and (p) $R^{10}$;

$R^{6a}$ is selected from the group consisting of (1) —$C_{1-6}$alkyl optionally substituted with one or more substituents selected from the group consisting of $R^{12}$ and $R^{13}$, (2) —$C_{1-6}$alkyl-$R^{10}$ and (3) —$C_{3-6}$ cycloalkyl optionally substituted with one or more substituents selected from the group consisting of $R^{12}$ and $R^{13}$;

$R^7$ is selected from the group consisting of (a) —H, (b) —$C_{1-6}$alkyl optionally substituted with one or more substituents selected from the group consisting of —F, —$NH_2$ and —OH, (c) —$C_{3-6}$ cycloalkyl optionally substituted with one or more substituents selected from the group consisting of methyl, —$CF_3$, —F, —$NH_2$ and —OH, (d) —$COC_{1-6}$alkyl optionally substituted with one or more substituents selected from the group consisting of —F and —OH, (e) —$COC_{3-6}$cycloalkyl optionally substituted with one or more substituents selected from the group consisting of methyl, —$CF_3$, —F, —$NH_2$ and —OH, and (f) a 4-6 membered saturated heterocyclic ring containing one N, wherein the ring is bonded to the nitrogen in —$NR^7R^8$ through a carbon atom in the ring, and wherein the ring is optionally substituted with one or more substituents selected from the group consisting of methyl, —$CF_3$, —F, —$NH_2$ and —OH;

$R^8$ is selected from the group consisting of (a) —H, (b) —$C_{1-6}$alkyl optionally substituted with one or more substituents selected from the group consisting of —F, —$NH_2$ and —OH, and (c) —$C_{3-6}$cycloalkyl optionally substituted with one or more substituents selected from the group consisting of methyl, —$CF_3$, —F, —$NH_2$ and —OH;

or $R^7$ and $R^8$ together represent —$(CH_2)_{3-5}$— which is bonded with the nitrogen to which $R^7$ and $R^8$ are attached to form a 4-6 membered ring, wherein the ring is optionally substituted with a substituent selected form the group consisting of —$CH_3$, —$CF_3$, —F and —OH;

$R^9$ is selected from the group consisting of —H, —OH, —$C_{1-3}$alkyl and —F;

$R^{10}$ is a heterocyclic ring selected from the group consisting of (a) azetidinyl optionally substituted with one or more of methyl, —F and —OH, (b) pyrrolidinyl optionally substituted with one or more of methyl, —F and —OH, (c) piperidinyl optionally substituted with one or more of methyl, —F and —OH and (d) morpholinyl optionally substituted with one or more of methyl, —F and —OH;

Y is selected from the group consisting of (a) a 5-membered aromatic or partially unsaturated heterocyclic ring containing 1 to 4 heteroatoms selected from 1 to 4 of N and zero to 1 of S, wherein the heterocyclic ring is optionally substituted with $R^{11}$, (b) a 6-membered aromatic or partially unsaturated heterocyclic ring containing 1 to 4 N heteroatoms, wherein the heterocyclic ring is optionally substituted with $R^{11}$, (c) a 9-membered bicyclic aromatic or partially unsaturated heterocyclic ring containing 1 to 4 N heteroatoms, wherein the heterocyclic ring is optionally substituted with $R^{11}$ and (d) a 10-membered bicyclic aromatic or partially unsaturated heterocyclic ring containing 1 to 4 N heteroatoms, wherein the heterocyclic ring is optionally substituted with $R^{11}$; and $R^{11}$ is selected from the group consisting of —F, —$NH_2$, —OH, —$OC_{3-4}$cycloalkyl, —$C_{1-3}$alkyl optionally substituted with 1-3 fluoro, and —$OC_{1-3}$alkyl optionally substituted with phenyl or 1-3 fluoro;

$R^{12}$ is selected from the group consisting of: —$CO_2R^4$, —C(O)$NR^7R^8$, —N($R^a$)$_2$, —$NR^bSO_pR^a$, —$NR^bC(O)R^a$, —$NR^bC(O)NR^aR^b$, —S(O)$_pNR^aR^b$, —S(O)$_pR^a$, —F, —$CF_3$, phenyl, Hetcy and $Z^1$, $R^{13}$ is selected from the group consisting of —OH, —$NH_2$ and —F;

each $R^a$ is independently selected from the group consisting of a) —H, b) —$C_{1-4}$alkyl, —$C_{2-4}$alkenyl and —$C_{2-4}$alkynyl, wherein each is optionally substituted with 1-2 substituents selected from the group consisting of: —OH, —$OC_{1-4}$alkyl, —CN, —$NH_2$, —$NHC_{1-4}$alkyl, and —N($C_{1-4}$alkyl)$_2$, and —$CF_3$, and optionally with 1-3 of fluoro, c) Hetcy and Hetcy-$C_{1-4}$alkyl-, the Hetcy moieties being optionally substituted on carbon with 1-2 substituents selected from the group consisting of —F, —OH, —$CO_2H$, —$C_{1-4}$alkyl, —$CO_2C_{1-4}$alkyl, —$OC_{1-4}$alkyl, —$NH_2$, —$NHC_{1-4}$alkyl, —N($C_{1-4}$alkyl)$_2$, —NHC(O)$C_{1-4}$alkyl, oxo, —C(O)$NHC_{1-4}$alkyl and —C(O)N($C_{1-4}$alkyl)$_2$; and optionally substituted on nitrogen when present with a group selected from —$C_{1-4}$alkyl and —$C_{1-4}$acyl; and the alkyl portion of Hetcy-$C_{1-4}$alkyl- being optionally substituted with a member selected from the group consisting of —OH, —CN, —$OC_{1-4}$alkyl, —$NH_2$, —$NHC_{1-4}$alkyl, —$N(C_{1-4}$alkyl$)_2$ and 1-3 of fluoro, d) $Z^2$ and $Z^2$-$C_{1-4}$alkyl-, the alkyl portion of $Z^2$-$C_{1-4}$alkyl - being optionally substituted with a substituent selected from the group consisting of —OH, —CN, —$OC_{1-4}$alkyl, —$NH_2$, —$NHC_{1-4}$alkyl, —$N(C_{1-4}$alkyl$)_2$ and 1-3 of fluoro;

each $R^b$ is independently selected from the group consisting of —H and —$C_{1-3}$alkyl optionally substituted with 1-2 members selected from the group consisting of $NH_2$, —OH, —F, —CN and —$CF_3$;

$R^c$, $R^d$, and $R^e$ are each independently selected from —H, —F, —Cl, —OH, —CN, —$C_{1-4}$alkyl optionally substituted with 1-3 of fluoro, and —$OC_{1-4}$alkyl optionally substituted with 1-3 of fluoro;

Hetcy is selected from the group consisting of azetidinyl, pyrrolidinyl, piperidinyl, piperazinyl, morpholinyl, tetrahydrofuranyl and β-lactamyl, δ-lactamyl, γ-lactamyl and tetrahydropyranyl;

$Z^1$ is selected from the group consisting of:
a) $Z^2$,
b) an 8-membered aromatic or partially unsaturated ortho-fused bicyclic ring system containing 3-5 heteroatoms selected from one sulfur and 2-4 of nitrogen wherein one carbon in the ring is optionally substituted with a group selected from =O, =S, —SMe, —$NH_2$, —$CF_3$, —Cl, —$C_{1-4}$alkyl and $C_{1-4}$alkyl substituted with a group selected from —$NH_2$, —OH, —$OC_{1-4}$alkyl, —CN and 1-3 of fluoro, and
c) a 9-membered aromatic or partially unsaturated ortho-fused bicyclic ring system containing 3-4 nitrogen atoms, wherein one carbon in the ring is optionally substituted with a group selected from =O, =S, —SMe, —$NH_2$, —$CF_3$, —Cl, —$C_{1-4}$alkyl and —$C_{1-4}$ alkyl substituted with a group selected from —$NH_2$, —OH, —$OC_{1-4}$alkyl, —CN and 1-3 of fluoro; and $Z^2$ is selected from the group consisting of:
a) a 5-membered aromatic or partially unsaturated heterocyclic ring containing 2-4 nitrogen atoms, wherein one nitrogen in the ring is optionally substituted with a group selected from —$C_{1-4}$alkyl and —$C_{1-4}$alkyl substituted with a group selected from —$NH_2$, —OH, —CN and 1-3 of fluoro, and one carbon in the ring is optionally substituted with a group selected from =O, =S, —SMe, —$NH_2$, —$CF_3$, —Cl, —$C_{1-4}$alkyl and —$C_{1-4}$alkyl substituted with a group selected from —$NH_2$, —OH, —$OC_{1-4}$alkyl, —CN and 1-3 of fluoro,
b) a 5-membered aromatic or partially unsaturated heterocyclic ring containing 2-3 heteroatoms selected from one oxygen or one sulfur and 1-2 of nitrogen, wherein one nitrogen in the ring is optionally substituted with a group selected from —$C_{1-4}$alkyl and —$C_{1-4}$alkyl substituted with a group selected from —$NH_2$, —OH, —CN and 1-3 of fluoro, and one carbon in the ring is optionally substituted with a group selected from =O, =S, —SMe, —$NH_2$, —$CF_3$, —Cl, and $C_{1-4}$alkyl optionally substituted with a group selected from —$NH_2$, —OH, —O $C_{1-4}$alkyl, —CN and 1-3 of fluoro, and
c) a 6-membered aromatic or partially unsaturated heterocyclic ring containing 1-2 nitrogen atoms, wherein one nitrogen in the ring is optionally substituted with a group selected from —$C_{1-4}$alkyl and —$C_{1-4}$alkyl substituted with a group selected from —$NH_2$, —OH, —CN and 1-3 of fluoro, and one carbon in the ring is optionally substituted with a group selected from =O, =S, —SMe, —$NH_2$, —$CF_3$, —Cl, —$C_{1-4}$alkyl and —$C_{1-4}$alkyl substituted with a group selected from —$NH_2$, —OH, —$OC_{1-4}$alkyl, —CN and 1-3 of fluoro.

2. The compound of claim 1 wherein $R^2$ is selected from the group consisting of i-propyl, t-butyl, cyclopropyl, cyclobutyl,

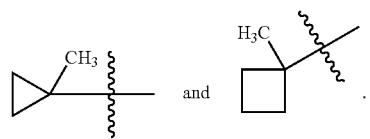

3. The compound of claim 2 wherein $R^3$ is selected from the group consisting of —H and —$CH_3$.

4. The compound of claim 3 wherein Y is a 6-membered aromatic or partially unsaturated heterocyclic ring containing 1 to 2 N heteroatoms, wherein the heterocyclic ring is optionally substituted with $R^{11}$.

5. The compound of claim 4 wherein $R^{11}$ is —$NH_2$ or $OC_{1-3}$alkyl optionally substituted with phenyl or 1-3 flouro.

6. The compound of claim 5 wherein Y is selected from:

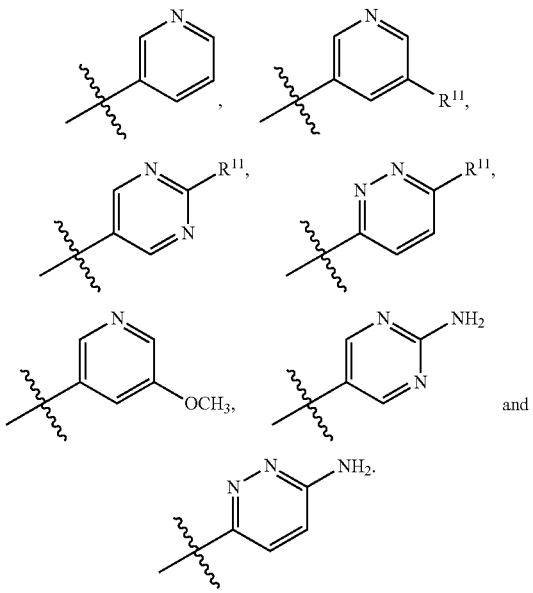

7. The compound of claim 6 wherein $R^1$ is selected from (a) a 5-membered aromatic or partially unsaturated heterocyclic ring containing a total of 2 to 4 heteroatoms selected from two to four of N, zero to one of O, and zero to one of S, wherein the heterocyclic ring is optionally substituted with $R^6$, and (b) a 6-membered aromatic or partially unsaturated heterocyclic ring containing 1 to 2 heteroatoms selected from N and O, wherein the heterocyclic ring is optionally substituted with $R^6$.

8. A compound represented by structural Formula II

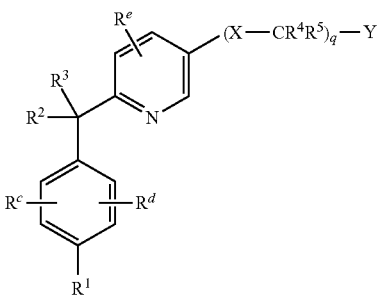

and the pharmaceutically acceptable salts thereof wherein:
q is 0 (zero);
$R^1$ is selected from the group consisting of:
  (a) a 5-membered aromatic or partially unsaturated heterocyclic ring containing 2 to 4 heteroatoms selected from N, S and O, wherein the heterocylic ring is optionally substituted with $R^6$,
  (b) a 6-membered aromatic or partially unsaturated heterocyclic ring containing 1 to 2 heteroatoms selected from N and O, wherein the heterocyclic ring is optionally substituted with $R^6$;
  (c) an 8-membered aromatic or partially unsaturated ortho-fused bicyclic ring system containing 3-5 heteroatoms selected from one sulfur and 2-4 of nitrogen wherein one carbon in the ring is optionally substituted with a group selected from =O, =S, —SMe, —$NH_2$, —$CF_3$, —Cl, —$C_{1-4}$alkyl and $C_{1-4}$alkyl substituted with a group selected from —$NH_2$, —OH, —$OC_{1-4}$alkyl, —CN and 1-3 of fluoro,
  (d) a 9-membered aromatic or partially unsaturated ortho-fused bicyclic ring system containing 3-4 nitrogen atoms, wherein one carbon in the ring is optionally substituted with a group selected from =O, =S, —SMe, —$NH_2$, —$CF_3$, —Cl, —$C_{1-4}$alkyl and —$C_{1-4}$ alkyl substituted with a group selected from —$NH_2$, —OH, —$OC_{1-4}$alkyl, —CN and 1-3 of fluoro;
  (e) —$C_{1-6}$alkyl, —$C_{2-6}$alkenyl, and —$C_{2-6}$alkynyl, said alkyl, alkenyl and alkynyl groups being optionally substituted with $R^{12}$ and optionally substituted with $R^{13}$;
  (f) —$C_{3-6}$ cycloalkyl optionally substituted with 1-3 substituents selected from the group consisting of fluoro, —$NH_2$, —OH and —$C_{1-3}$alkyl optionally substituted with 1-3 of fluoro:
  (g) —O—$R^{6a}$; and
  (h) —H, —OH, —CN, —$CO_2R^4$, —C(O)$NR^7R^8$, —$NR^7R^8$, —$NR^bSO_pR^a$, —$NR^bC(O)R^a$, —$NR^bC(O)NR^aR^b$, —S(O)$_pR^a$, and —S(O)$_pNR^aR^b$;
p is an integer selected from 0, 1 and 2;
$R^2$ is selected from the group consisting of i-propyl, t-butyl, cyclopropyl, cyclobutyl,

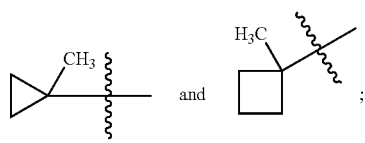

n is an integer selected from 0, 1, 2 and 3;

$R^3$ is selected from the group consisting of —H and —$CH_3$; or
$R^2$ and $R^3$ are taken in combination and represent a mono- or bi-cyclic ring system containing 3 to 8 carbon atoms, said system being optionally substituted with 1-2 groups selected from: $C_{1-3}$alkyl, $OC_{1-3}$alkyl, F, OH, mono-, di- or tri-fluoro$C_{1-3}$alkyl and mono-, di- and tri-fluoro$C_{1-3}$ alkoxy;
$R^6$, when present, is selected from the group consisting of:
  (a) —$CR^aR^bR^c$ wherein $R^a$ is selected from —H, —$C_{1-3}$alkyl and —F, $R^b$ is selected from —H, —$C_{1-3}$alkyl and —F, and $R^c$ is selected from —H, —$C_{1-3}$alkyl, —F, —$NH_2$ and —OH; or $R^a$ and $R^b$ are joined together with the carbon to which they are attached to form a cyclopropyl ring; (b) —$CH_2$—$R^{10}$, (c) —$OCH_3$ optionally substituted with 1-3 fluoro, (d) —$NR^7R^8$, (e) —$SO_2CH_3$ and (f) oxo.
$R^{6a}$ is selected from the group consisting of (1) —$C_{1-6}$alkyl optionally substituted with one or more substituents selected from the group consisting of $R^{12}$ and $R^{13}$, (2) —$C_{1-6}$alkyl-$R^{10}$ and (3) —$C_{3-6}$ cycloalkyl optionally substituted with one or more substituents selected from the group consisting of $R^{12}$ and $R^{13}$;
$R^7$ is selected from the group consisting of (a) —H, (b) —$C_{1-6}$alkyl optionally substituted with one or more substituents selected from the group consisting of —F, —$NH_2$ and —OH, (c) —$C_{3-6}$ cycloalkyl optionally substituted with one or more substituents selected from the group consisting of methyl, —$CF_3$, —F, —$NH_2$ and —OH, (d) —$COC_{1-6}$alkyl optionally substituted with one or more substituents selected from the group consisting of —F and —OH, (e) —$COC_{3-6}$cycloalkyl optionally substituted with one or more substituents selected from the group consisting of methyl, —$CF_3$, —F, —$NH_2$ and —OH, and (f) a 4-6 membered saturated heterocyclic ring containing one N, wherein the ring is bonded to the nitrogen in —$NR^7R^8$ through a carbon atom in the ring, and wherein the ring is optionally substituted with one or more substituents selected from the group consisting of methyl, —$CF_3$, —F, —$NH_2$ and —OH;
$R^8$ is selected from the group consisting of (a) —H, (b) —$C_{1-6}$alkyl optionally substituted with one or more substituents selected from the group consisting of —F, —$NH_2$ and —OH, and (c) —$C_{3-6}$cycloalkyl optionally substituted with one or more substituents selected from the group consisting of methyl, —$CF_3$, —F, —$NH_2$ and —OH;
or $R^7$ and $R^8$ together represent —$(CH_2)_{3-5}$— which is bonded with the nitrogen to which $R^7$ and $R^8$ are attached to form a 4-6 membered ring, wherein the ring is optionally substituted with a substituent selected form the group consisting of —$CH_3$, —$CF_3$, —F and —OH;
$R^9$ is selected from the group consisting of —H, —OH, —$C_{1-3}$alkyl and —F;
$R^{10}$ is a heterocyclic ring selected from the group consisting of (a) azetidinyl optionally substituted with one or more of methyl, —F and —OH, (b) pyrrolidinyl optionally substituted with one or more of methyl, —F and —OH, (c) piperidinyl optionally substituted with one or more of methyl, —F and —OH and (d) morpholinyl optionally substituted with one or more of methyl, —F and —OH;

Y is selected from:

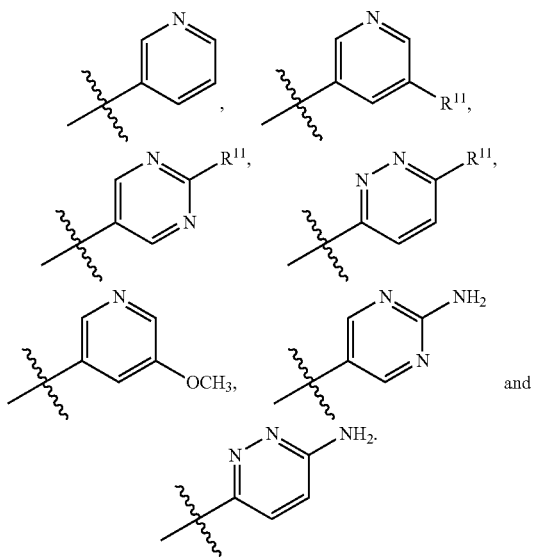

$R^{11}$ is —$NH_2$ —$C_{1-3}$alkyl optionally substituted with 1-3 fluoro, and —$OC_{1-3}$alkyl optionally substituted with phenyl or 1-3 fluoro;

$R^{12}$ is selected from the group consisting of: —$CO_2R^4$, —$C(O)NR^7R^8$, —$N(R^a)_2$, —$NR^bSO_pR^a$, —$NR^bC(O)R^a$, —$NR^bC(O)NR^aR^b$, —$S(O)_pNR^aR^b$, —$S(O)_pR^a$, —F, —$CF_3$, phenyl, Hetcy and $Z^1$, $R^{13}$ is selected from the group consisting of —OH, —$NH_2$ and —F;

each $R^a$ is independently selected from the group consisting of
 a) —H,
 b) —$C_{1-4}$alkyl, —$C_{2-4}$alkenyl and —$C_{2-4}$alkynyl, wherein each is optionally substituted with 1-2 substituents selected from the group consisting of: —OH, —$OC_{1-4}$, —CN, —$NH_2$, —$NHC_{1-4}$alkyl, and —$N(C_{1-4}$alkyl$)_2$, and —$CF_3$, and optionally with 1-3 of fluoro,
 c) Hetcy and Hetcy-$C_{1-4}$alkyl-, the Hetcy moieties being optionally substituted on carbon with 1-2 substituents selected from the group consisting of —F, —OH, —$CO_2H$, —$C_{1-4}$alkyl, —$CO_2C_{1-4}$alkyl, —$OC_{1-4}$alkyl, —$NH_2$, —$NHC_{1-4}$alkyl, —$N(C_{1-4}$alkyl$)_2$, —$NHC(O)C_{1-4}$alkyl, oxo, —$C(O)NHC_{1-4}$alkyl and —$C(O)N(C_{1-4}$alkyl$)_2$; and optionally substituted on nitrogen when present with a group selected from —$C_{1-4}$alkyl and —$C_{1-4}$acyl; and the alkyl portion of Hetcy-$C_{1-4}$alkyl- being optionally substituted with a member selected from the group consisting of —OH, —CN, —$OC_{1-4}$alkyl, —$NH_2$, —$NHC_{1-4}$alkyl, —$N(C_{1-4}$alkyl$)_2$ and 1-3 of fluoro,
 d) $Z^2$ and $Z^2$—$C_{1-4}$alkyl-, the alkyl portion of $Z^2$—$C_{1-4}$alkyl- being optionally substituted with a substituent selected from the group consisting of —OH, —CN, —$OC_{1-4}$alkyl, —$NH_2$, —$NHC_{1-4}$alkyl, —$N(C_{1-4}$alkyl$)_2$ and 1-3 of fluoro;

each $R^b$ is independently selected from the group consisting of —H and —$C_{1-3}$alkyl optionally substituted with 1-2 members selected from the group consisting of $NH_2$, —OH, —F, —CN and —$CF_3$;

$R^c$, $R^d$, and $R^e$ are each independently selected from —H, —F, —Cl, —OH, —CN, —$C_{1-4}$alkyl optionally substituted with 1-3 of fluoro, and —$OC_{1-4}$alkyl optionally substituted with 1-3 of fluoro;

Hetcy is selected from the group consisting of azetidinyl, pyrrolidinyl, piperidinyl, piperazinyl, morpholinyl, tetrahydrofuranyl and β-lactamyl, δ-lactamyl, γ-lactamyl and tetrahydropyranyl;

$Z^1$ is selected from the group consisting of:
 a) $Z^2$,
 b) an 8-membered aromatic or partially unsaturated ortho-fused bicyclic ring system containing 3-5 heteroatoms selected from one sulfur and 2-4 of nitrogen wherein one carbon in the ring is optionally substituted with a group selected from =O, =S, —SMe, —$NH_2$, —$CF_3$, —Cl, —$C_{1-4}$alkyl and $C_{1-4}$alkyl substituted with a group selected from —$NH_2$, —OH, —$OC_{1-4}$alkyl, —CN and 1-3 of fluoro, and
 c) a 9-membered aromatic or partially unsaturated ortho-fused bicyclic ring system containing 3-4 nitrogen atoms, wherein one carbon in the ring is optionally substituted with a group selected from =O, =S, —SMe, —$NH_2$, —$CF_3$, —Cl, —$C_{1-4}$alkyl and —$C_{1-4}$alkyl substituted with a group selected from —$NH_2$, —OH, —$OC_{1-4}$alkyl, —CN and 1-3 of fluoro; and $Z^2$ is selected from the group consisting of:
 a) a 5-membered aromatic or partially unsaturated heterocyclic ring containing 2-4 nitrogen atoms, wherein one nitrogen in the ring is optionally substituted with a group selected from —$C_{1-4}$alkyl and —$C_{1-4}$alkyl substituted with a group selected from —$NH_2$, —OH, —CN and 1-3 of fluoro, and one carbon in the ring is optionally substituted with a group selected from =O, =S, —SMe, —$NH_2$, —$CF_3$, —Cl, —$C_{1-4}$alkyl and —$C_{1-4}$alkyl substituted with a group selected from —$NH_2$, —OH, —$OC_{1-4}$alkyl, —CN and 1-3 of fluoro,
 b) a 5-membered aromatic or partially unsaturated heterocyclic ring containing 2-3 heteroatoms selected from one oxygen or one sulfur and 1-2 of nitrogen, wherein one nitrogen in the ring is optionally substituted with a group selected from —$C_{1-4}$alkyl and —$C_{1-4}$alkyl substituted with a group selected from —$NH_2$, —OH, —CN and 1-3 of fluoro, and one carbon in the ring is optionally substituted with a group selected from =O, =S, —SMe, —$NH_2$, —$CF_3$, —Cl, and $C_{1-4}$alkyl optionally substituted with a group selected from —$NH_2$, —OH, —$OC_{1-4}$alkyl, —CN and 1-3 of fluoro, and
 c) a 6-membered aromatic or partially unsaturated heterocyclic ring containing 1-2 nitrogen atoms, wherein one nitrogen in the ring is optionally substituted with a group selected from —$C_{1-4}$alkyl and —$C_{1-4}$alkyl substituted with a group selected from —$NH_2$, —OH, —CN and 1-3 of fluoro, and one carbon in the ring is optionally substituted with a group selected from =O, =S, —SMe, —$NH_2$, —$CF_3$, —Cl, —$C_{1-4}$alkyl and —$C_{1-4}$alkyl substituted with a group selected from —$NH_2$, —OH, —$OC_{1-4}$alkyl, —CN and 1-3 of fluoro.

9. The compound of claim 8 wherein $R^6$ is selected from the group consisting of —C(CH$_3$)$_2$OH,

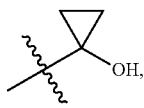

—CH$_3$, —CF$_3$ and —CH$_2$—R$^{10}$.

10. The compound of claim 9 wherein $R^{10}$ is selected from

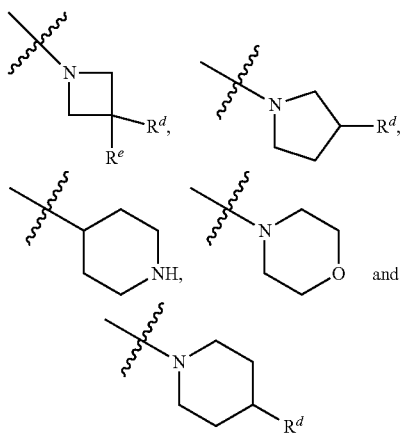

wherein R$^d$ is selected from —F and —OH, and R$^e$ is selected from —H, —F, and —OH.

11. The compound of claim 1 having structural Formula IIa

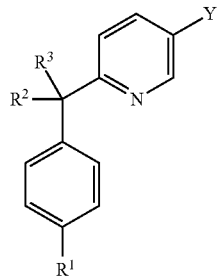

and the pharmaceutically acceptable salts thereof.

12. The compound of claim 11 wherein R$^1$ is selected from the group consisting of:

(a) a 5-membered aromatic or partially unsaturated heterocyclic ring containing a total of 2 to 4 heteroatoms selected from two to four of N, zero to one of O, and zero to one of S, wherein the heterocyclic ring is optionally substituted with R$^6$, (b) a 6-membered aromatic or partially unsaturated heterocyclic ring containing 1 to 2 heteroatoms selected from N and O, wherein the heterocyclic ring is optionally substituted with R$^6$, (c) —C$_{1-4}$alkyl optionally substituted with R$^{12}$, and optionally substituted with R$^{13}$, (d) —OR$^{6a}$ wherein R$^{6a}$ is —C$_{1-4}$alkyl optionally substituted with R$^{13}$, (e) —CO$_2$C$_{1-6}$alkyl, (f) —C(O)NR$^7$R$^8$, (g) —CN, and (h) —C$_{3-6}$ cycloalkyl optionally substituted with R$^{12}$, and optionally substituted with R$^{13}$; and Y is a 6-membered aromatic heterocyclic ring containing 1 to 2 N heteroatoms wherein the heterocyclic ring is optionally substituted with R$^{11}$.

13. A pharmaceutical composition comprised of a therapeutically effective amount of a compound of claim 1 and a pharmaceutically acceptable carrier.

14. A method of treating atherosclerosis comprising administering a therapeutically effective amount of a compound of claim 1 to a patient in need of such treatment.

15. A method for the treatment of asthma or COPD comprising administering a therapeutically effective amount of a compound of claim 1 to a patient in need of such treatment.

16. A method of inhibiting the synthesis, the action, or the release of leukotrienes in a mammal which comprises administering to said mammal an effective amount of a compound of claim 1.

17. The compound of claim 1 selected from the group consisting of:

6'-(1,2-dimethyl-1-{4-[6-(trifluoromethyl)pyridazin-3-yl]phenyl}propyl)-5-methoxy-3,3'-bipyridine;

3-[4-(1-{5-[2-(2,5-dimethyl-1H-pyrrol-1-yl)pyrimidin-5-yl]pyridin-2-yl}-1,2-dimethylpropyl)phenyl]-6-(trifluoromethyl)pyridazine; and 5-[4-(1,2-dimethyl-1-{5-[6-(trifluoromethyl)pyridazin-3-yl]pyridin-2-yl}propyl)phenyl]pyrimidin-2-amine.

* * * * *